US00RE49093E

(19) United States
(12) Reissued Patent
Nagao et al.

(10) Patent Number: US RE49,093 E
(45) Date of Reissued Patent: Jun. 7, 2022

(54) LIGHT-EMITTING APPARATUS INCLUDING PHOTOLUMINESCENT LAYER

(71) Applicant: Panasonic Intellectual Property Management Co., Ltd., Osaka (JP)

(72) Inventors: Nobuaki Nagao, Gifu (JP); Taku Hirasawa, Kyoto (JP); Yasuhisa Inada, Osaka (JP); Mitsuru Nitta, Osaka (JP); Akira Hashiya, Osaka (JP); Yasuhiko Adachi, Hyogo (JP)

(73) Assignee: PANASONIC INTELLECTUAL PROPERTY MANAGEMENT CO., LTD., Osaka (JP)

(21) Appl. No.: 17/152,753

(22) Filed: Jan. 19, 2021

Related U.S. Patent Documents

Reissue of:
(64) Patent No.: 10,182,702
Issued: Jan. 22, 2019
Appl. No.: 15/060,574
Filed: Mar. 3, 2016

(30) Foreign Application Priority Data

Mar. 13, 2015 (JP) ..... 2015-050681
Aug. 28, 2015 (JP) ..... 2015-169024

(51) Int. Cl.
*A61B 1/06* (2006.01)
*A61B 1/00* (2006.01)
(Continued)

(52) U.S. Cl.
CPC ..... *A61B 1/00096* (2013.01); *A61B 1/0684* (2013.01); *G02B 6/0038* (2013.01); *H04N 5/2256* (2013.01)

(58) Field of Classification Search
CPC ..... A61B 1/00096; A61B 1/0684; G02B 6/0038; H04N 5/2256
See application file for complete search history.

(56) References Cited

U.S. PATENT DOCUMENTS 5,517,039 A 5/1996 Holonyak, Jr. et al.
5,732,102 A 3/1998 Bouadma
(Continued)

FOREIGN PATENT DOCUMENTS

JP 9-073807 3/1997
JP 11-283751 10/1999
(Continued)

OTHER PUBLICATIONS

Non-Final Office Action issued in U.S. Appl. No. 15/060,574, dated Jan. 16, 2018.
(Continued)

*Primary Examiner* — Deandra M Hughes
(74) *Attorney, Agent, or Firm* — McDemott Will & Emery LLP

(57) ABSTRACT

A light-emitting apparatus includes; a light-emitting device including a photoluminescent layer that receives excitation light and emits light including first light having a wavelength $\lambda_a$ in air, and a light-transmissive layer located on or near the photoluminescent layer; and an optical fiber that receives the light from the photoluminescent layer at one end of the optical fiber and emits the received light from the other end thereof. A surface structure is defined on at least one of the photoluminescent layer and the light-transmissive layer, and the surface structure has projections or recesses or both and limits a directional angle of the first light having the wavelength $\lambda_a$ in air.

51 Claims, 55 Drawing Sheets

(51) Int. Cl.
*F21V 8/00* (2006.01)
*H04N 5/225* (2006.01)

(56) References Cited

U.S. PATENT DOCUMENTS

| | | | | |
|---|---|---|---|---|
| 6,483,096 | B1 | 11/2002 | Kunz et al. | |
| 6,728,034 | B1 | 4/2004 | Nakanishi et al. | |
| 7,619,357 | B2 | 11/2009 | Onishi et al. | |
| 7,699,482 | B2 | 4/2010 | Noguchi | |
| 8,227,966 | B2 | 7/2012 | Wakabayashi et al. | |
| 8,619,363 | B1 | 12/2013 | Coleman | |
| 9,158,215 | B2 | 10/2015 | Yu | |
| 9,515,239 | B2 | 12/2016 | Inada et al. | H01L 33/58 |
| 9,518,215 | B2 | 12/2016 | Hirasawa et al. | H05B 33/14 |
| 9,618,697 | B2 | 4/2017 | Inada et al. | |
| 9,880,336 | B2 | 1/2018 | Inada et al. | |
| 9,882,100 | B2 * | 1/2018 | Hashiya | H01L 33/505 |
| 9,890,912 | B2 | 2/2018 | Hashiya et al. | F21K 9/64 |
| 10,012,780 | B2 | 7/2018 | Inada et al. | |
| 10,031,276 | B2 * | 7/2018 | Hirasawa | G02B 6/005 |
| 10,094,522 | B2 * | 10/2018 | Hirasawa | H01L 33/58 |
| 10,113,712 | B2 * | 10/2018 | Inada | F21V 13/14 |
| 10,359,155 | B2 * | 7/2019 | Hirasawa | F21V 9/40 |
| 2002/0180348 | A1 | 12/2002 | Oda et al. | |
| 2003/0021314 | A1 | 1/2003 | Yoshida et al. | |
| 2003/0169792 | A1 | 9/2003 | Kim | |
| 2004/0141108 | A1 | 7/2004 | Tanaka et al. | |
| 2004/0233534 | A1 | 11/2004 | Nakanishi et al. | |
| 2006/0039433 | A1 | 2/2006 | Simpson | |
| 2006/0088066 | A1 | 4/2006 | He | |
| 2007/0031097 | A1 | 2/2007 | Heikenfeld et al. | |
| 2007/0103931 | A1 | 5/2007 | Lee et al. | |
| 2007/0138479 | A1 | 6/2007 | Yamazaki et al. | |
| 2007/0153860 | A1 | 7/2007 | Chang-Hasnain et al. | |
| 2008/0069497 | A1 | 3/2008 | Tissot et al. | |
| 2008/0089089 | A1 * | 4/2008 | Hama | A61B 1/0653 362/574 |
| 2008/0149916 | A1 | 6/2008 | Baba et al. | |
| 2008/0258160 | A1 | 10/2008 | Do | |
| 2008/0303419 | A1 | 12/2008 | Fukuda | |
| 2009/0021153 | A1 | 1/2009 | Lee et al. | |
| 2009/0040598 | A1 * | 2/2009 | Ito | A61B 1/0638 359/332 |
| 2009/0040745 | A1 | 2/2009 | Nemchuk | |
| 2009/0066241 | A1 | 3/2009 | Yokoyama | |
| 2009/0129115 | A1 | 5/2009 | Fine et al. | |
| 2009/0190068 | A1 | 7/2009 | Kawamura | |
| 2009/0206325 | A1 | 8/2009 | Biwa et al. | |
| 2009/0267092 | A1 | 10/2009 | Fukshima et al. | |
| 2009/0286337 | A1 | 11/2009 | Lee et al. | |
| 2010/0074284 | A1 | 3/2010 | Aizawa et al. | |
| 2010/0142189 | A1 | 6/2010 | Hong et al. | |
| 2010/0164365 | A1 | 7/2010 | Yoshino et al. | |
| 2010/0176751 | A1 | 7/2010 | Oshio et al. | |
| 2010/0246210 | A1 | 9/2010 | Yashiro | |
| 2010/0277887 | A1 | 11/2010 | Su et al. | |
| 2011/0101359 | A1 | 5/2011 | Kim et al. | |
| 2011/0198563 | A1 | 8/2011 | Kim et al. | |
| 2011/0198645 | A1 | 8/2011 | Jo et al. | |
| 2012/0018705 | A1 | 1/2012 | Takazoe et al. | |
| 2012/0106127 | A1 | 5/2012 | Hattori et al. | |
| 2012/0119638 | A1 | 5/2012 | Sato et al. | |
| 2012/0176766 | A1 | 7/2012 | Natsumeda | |
| 2012/0224378 | A1 | 9/2012 | Koike et al. | |
| 2012/0286258 | A1 | 11/2012 | Naraoka et al. | |
| 2012/0292652 | A1 | 11/2012 | Yamae et al. | |
| 2013/0069046 | A1 | 3/2013 | Ishizuya | |
| 2013/0181195 | A1 | 7/2013 | Cho et al. | |
| 2013/0208327 | A1 | 8/2013 | Bolle et al. | |
| 2013/0277703 | A1 | 10/2013 | Matsuzaki | |
| 2013/0308102 | A1 | 11/2013 | Natsumeda et al. | |
| 2014/0022818 | A1 | 1/2014 | Natsumeda et al. | |
| 2014/0071683 | A1 | 3/2014 | Hamada et al. | |
| 2014/0092620 | A1 | 4/2014 | Tissot | |
| 2014/0185316 | A1 | 7/2014 | Kim et al. | |
| 2014/0306176 | A1 | 10/2014 | Chiu et al. | |
| 2014/0362604 | A1 | 12/2014 | Masuda | |
| 2015/0085469 | A1 * | 3/2015 | Kamee | A61B 1/0653 362/84 |
| 2015/0249183 | A1 | 9/2015 | Hirasawa et al. | |
| 2015/0249186 | A1 | 9/2015 | Inada et al. | |
| 2015/0249187 | A1 | 9/2015 | Inada et al. | |
| 2015/0252964 | A1 * | 9/2015 | Takahashi | F21K 9/60 362/84 |
| 2016/0265746 | A1 | 9/2016 | Hirasawa et al. | |
| 2016/0265747 | A1 | 9/2016 | Nagao et al. | |
| 2016/0265749 | A1 | 9/2016 | Inada | |
| 2016/0327706 | A1 | 11/2016 | Hirasawa et al. | |
| 2016/0327715 | A1 | 11/2016 | Inada et al. | |
| 2016/0327716 | A1 | 11/2016 | Inada et al. | |
| 2016/0327717 | A1 | 11/2016 | Hashiya et al. | |
| 2016/0327739 | A1 | 11/2016 | Nakamura et al. | |
| 2017/0012232 | A1 | 1/2017 | Kataishi et al. | |
| 2017/0075169 | A1 | 3/2017 | Hayama | |

FOREIGN PATENT DOCUMENTS

| | | | |
|---|---|---|---|
| JP | 2001-059905 | | 3/2001 |
| JP | 2001-155520 | | 6/2001 |
| JP | 2006-269294 | A | 10/2006 |
| JP | 2007-103901 | | 4/2007 |
| JP | 2007-240641 | | 9/2007 |
| JP | 2008-130279 | | 6/2008 |
| JP | 2008-521211 | | 6/2008 |
| JP | 2008-227458 | | 9/2008 |
| JP | 2009-140894 | | 6/2009 |
| JP | 2010-015874 | | 1/2010 |
| JP | 2010-033772 | | 2/2010 |
| JP | 2010-035922 | A | 2/2010 |
| JP | 2010-097178 | A | 4/2010 |
| JP | 2010-199357 | | 9/2010 |
| JP | 2010-210824 | | 9/2010 |
| JP | 2010-231941 | | 10/2010 |
| JP | 2010-237311 | A | 10/2010 |
| JP | 2011-166148 | | 8/2011 |
| JP | 2012-093454 | | 5/2012 |
| JP | 2012-109334 | | 6/2012 |
| JP | 2012-109400 | | 6/2012 |
| JP | 2012-182376 | | 9/2012 |
| JP | 2013-183020 | | 9/2013 |
| JP | 2014-075584 | | 4/2014 |
| JP | 2014-082401 | | 5/2014 |
| JP | 2014-092645 | | 5/2014 |
| JP | 2014-523603 | | 9/2014 |
| WO | 2007/034827 | | 3/2007 |
| WO | 2007/091687 | | 8/2007 |
| WO | 2009/005311 | | 1/2009 |
| WO | 2009/099211 | | 8/2009 |
| WO | 2011/040528 | | 4/2011 |
| WO | 2012/049905 | | 4/2012 |
| WO | 2012/108384 | | 8/2012 |
| WO | 2012/137583 | A1 | 10/2012 |
| WO | 2012/137584 | | 10/2012 |
| WO | 2013/084442 | | 6/2013 |
| WO | 2013/125567 | | 8/2013 |
| WO | 2013/172025 | | 11/2013 |
| WO | 2014/024218 | | 2/2014 |
| WO | 2014/119783 | | 8/2014 |
| WO | 2015/045886 | | 4/2015 |

OTHER PUBLICATIONS

Notice of Allowance issued in U.S. Appl. No. 15/060,574 dated Sep. 12, 2018.

English translation of Search Report for Chinese application No. 201610261401.1, dated Dec. 29, 2018.

English translation of Search Report for Chinese application No. 201610256719.0, dated Dec. 29, 2018.

The Extended European Search Report dated Dec. 16, 2016 for the related European Patent Application No. 14883764.4.

Specification of U.S. Appl. No. 15/446,453, filed Mar. 1, 2017.

Non-Final Office Action issued in U.S. Appl. No. 15/216,669, dated Apr. 14, 2017.

(56) References Cited

OTHER PUBLICATIONS

Non-Final Office Action issued in U.S. Appl. No. 15/169,771, dated Aug. 16, 2017.
Non-Final Office Action issued in U.S. Appl. No. 15/214,803, dated Aug. 8, 2017.
Non-Final Office Action issued in U.S. Appl. No. 15/214,837, dated Sep. 12, 2017.
Non-Final Office Action issued in U.S. Appl. No. 15/215,595, dated Jul. 28, 2017.
Notice of Allowance issued in U.S. Appl. No. 15/215,595, dated Sep. 22, 2017.
Non-Final Office Action issued in U.S. Appl. No. 15/215,599, dated Aug. 25, 2017.
Non-Final Office Action issued in U.S. Appl. No. 15/219,462, dated Sep. 26, 2017.
Notice of Allowance issued in U.S. Appl. No. 15/169,771, dated Oct. 24, 2017.
Non-final Office Action issued in U.S. Appl. No. 14/618,591, dated Nov. 9, 2015.
Final Office Action issued in U.S. Appl. No. 14/618,591, dated May 19, 2016.
Non-final Office Action issued in U.S. Appl. No. 14/618,254, dated Feb. 3, 2016.
Non-Final Office Action issued in U.S. Appl. No. 14/621,729, dated Mar. 9, 2016.
Final Office Action issued in U.S. Appl. No. 14/621,729, dated Sep. 28, 2016.
International Search Report of PCT application No. PCT/JP2015/000810 dated Apr. 7, 2015.
International Search Report of PCT application No. PCT/JP2015/000811 dated Apr. 7, 2015.
International Search Report of PCT application No. PCT/JP2015/000812 dated Apr. 7, 2015.
International Search Report of PCT application No. PCT/JP2015/000813 dated May 19, 2015.
International Search Report of PCT application No. PCT/JP2015/000814 dated May 26, 2015.
International Search Report of PCT application No. PCT/JP2015/000815 dated Apr. 7, 2015.
International Search Report of PCT application No. PCT/JP2014/004324 dated Nov. 25, 2014; with English translation.
Specification of U.S. Appl. No. 15/166,123, filed May 26, 2016.
Specification of U.S. Appl. No. 15/169,771, filed Jun. 1, 2016.
Specification of U.S. Appl. No. 15/206,273, filed Jul. 10, 2016.
Specification of U.S. Appl. No. 15/214,523, filed Jul. 20, 2016.
Specification of U.S. Appl. No. 15/214,803, filed Jul. 20, 2016.
Specification of U.S. Appl. No. 15/214,837, filed Jul. 20, 2016.
Specification of U.S. Appl. No. 15/215,592, filed Jul. 21, 2016.
Specification of U.S. Appl. No. 15/215,595, filed Jul. 21, 2016.
Specification of U.S. Appl. No. 15/215,599, filed Jul. 21, 2016.
Specification of U.S. Appl. No. 15/216,669, filed Jul. 21, 2016.
Specification of U.S. Appl. No. 15/216,686, filed Jul. 21, 2016.
Specification of U.S. Appl. No. 15/219,462, filed Jul. 26, 2016.
Notice of Allowance issued in U.S. Appl. No. 15/060,564, dated Mar. 21, 2018.
Notice of Allowance issued in U.S. Appl. No. 15/216,686, dated Mar. 26, 2018.
Final Office Action issued in U.S. Appl. No. 15/215,592, dated Apr. 9, 2018.
Non-Final Office Action issued in U.S. Appl. No. 15/219,462, dated Feb. 28, 2018.
Final Office Action issued in U.S. Appl. No. 15/214,803, dated Feb. 5, 2018.
Notice of Allowance issued in related U.S. Appl. No. 15/214,523 dated Aug. 10, 2018.

* cited by examiner

LIGHT-EMITTING APPARATUS INCLUDING PHOTOLUMINESCENT LAYER

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*RELATED APPLICATIONS*

*This application is a reissue application of U.S. Pat. No. 10,182,702 issued on Jan. 22, 2019 issued from U.S. patent application Ser. No. 15/060,574 filed on Mar. 3, 2016, which claims the benefit of Japanese Patent Application No. 2015-050681 filed on Mar. 13, 2015 and Japanese Patent Application No. 2015-169024 filed on Aug. 28, 2015.*

BACKGROUND

1. Technical Field

The present disclosure relates to a light-emitting apparatus and an endoscope each including a light-emitting device having a photoluminescent layer.

2. Description of the Related Art

Optical devices, such as lighting fixtures, displays, and projectors, that output light in the necessary direction are required for many applications. Photoluminescent materials, such as those used for fluorescent lamps and white light-emitting diodes (LEDs), emit light in all directions. Thus, those materials are used in combination with optical elements such as reflectors and lenses to output light only in a particular direction. For example, Japanese Unexamined Patent Application Publication No. 2010-231941 discloses an illumination system including a light distributor and an auxiliary reflector to provide sufficient directionality.

SUMMARY

In one general aspect, the techniques disclosed here feature a light-emitting apparatus that includes; a light-emitting device including a photoluminescent layer that receives excitation light and emits light including first light having a wavelength $\lambda_a$ in air, and a light-transmissive layer located on or near the photoluminescent layer; and an optical fiber that receives the light from the photoluminescent layer at one end of the optical fiber and emits the received light from the other end thereof. A surface structure is defined on at least one of the photoluminescent layer and the light-transmissive layer, and the surface structure has projections or recesses or both and limits a directional angle of the first light having the wavelength $\lambda_a$ in air.

General or specific embodiments may be implemented as a device, an apparatus, a system, a method, or any selective combination thereof.

Additional benefits and advantages of the disclosed embodiments will become apparent from the specification and drawings. The benefits and/or advantages may be individually obtained by the various embodiments and features of the specification and drawings; which need not all be provided in order to obtain one or more of such benefits and/or advantages.

BRIEF DESCRIPTION OF THE DRAWINGS

FIG. 63 is a schematic view of light-emitting units used as headlights, taillights, and door lights;

FIG. 64 is a schematic view illustrating a navigation image displayed on a projection plane, such as a road surface, using a light-emitting unit in combination with a navigation system;

FIG. 65A is a schematic view of an automobile that includes an optical fiber sensor;

FIG. 65B is a schematic view of an airplane that includes an optical fiber sensor;

FIG. 66 is an explanatory view of the structure and the principle of operation of an optical fiber sensor;

FIG. 67 is a diagram of a drive signal and a light-responsive signal as a function of time;

FIG. 68 is a schematic view of the structure of a transparent display unit that includes a light-emitting device according to the present disclosure as a screen; and FIG. 69 is a schematic cross-sectional view of a surface structure having projections or recesses or both.

DETAILED DESCRIPTION

Figure 1A:
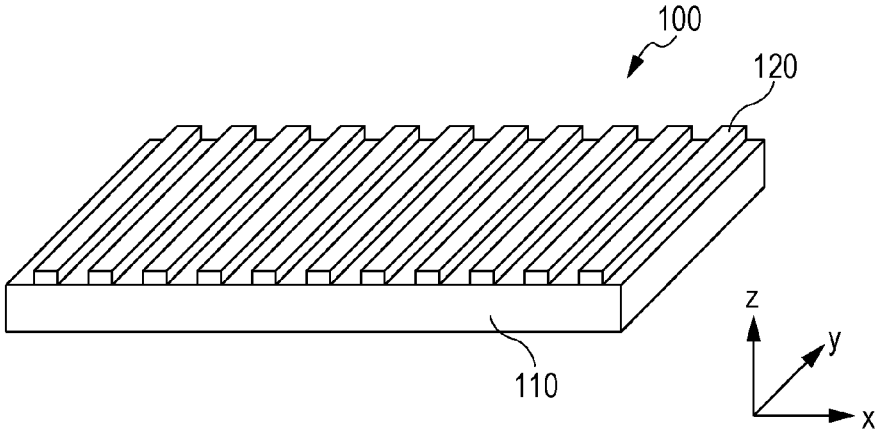
FIG. 1A is a perspective view showing the structure of a light-emitting device according to an embodiment.

1. Outline of Embodiments of Present Disclosure

The present disclosure includes the following light-emitting devices, light-emitting apparatuses, endoscopes, endoscope system, optical fiber lighting apparatuses, and optical fiber sensors.

[Item 1]A light-emitting device includes a photoluminescent layer, a light-transmissive layer located on or near the photoluminescent layer, and a submicron structure that is formed on at least one of the photoluminescent layer and the light-transmissive layer and extends in a plane of the photoluminescent layer or the light-transmissive layer, wherein the submicron structure has projections or recesses, light from the photoluminescent layer includes first light having a wavelength $\lambda_a$ in air, and a distance $D_{int}$ between adjacent projections or recesses and a refractive index $n_{wav\text{-}a}$ of the photoluminescent layer for the first light satisfy $\lambda_a/n_{wav\text{-}a}<D_{int}<\lambda_a$.

[Item 2] In Item 1, the submicron structure may include at least one periodic structure defined by at least the projections or recesses, and the at least one periodic structure may include a first periodic structure satisfying the following relationship: $\lambda_a/n_{wav\text{-}a}<p_a<\lambda_a$ where $p_a$ is a period of the first periodic structure.

[Item 3] In Item 1 or 2, a refractive index $n_{wav\text{-}a}$ of the light-transmissive layer for the first light may be lower than the refractive index $n_{wav\text{-}a}$ of the photoluminescent layer for the first light.

[Item 4] In any one of Items 1 to 3, the first light may have the maximum intensity in a first direction determined in advance by the submicron structure.

[Item 5] In Item 4, the first direction may be normal to the photoluminescent layer.

[Item 6] In Item 4 or 5, the first light output in the first direction may be linearly polarized light.

[Item 7] In any one of Items 4 to 6, a directional angle of the first light with respect to the first direction may be less than 15 degrees.

[Item 8] In any one of Items 4 to 7, second light having a wavelength $\lambda_b$ different from the wavelength $\lambda_a$ of the first light may have the maximum intensity in a second direction different from the first direction.

[Item 9] In any one of Items 1 to 8, the light-transmissive layer may have the submicron structure.

[Item 10] In any one of Items 1 to 9, the photoluminescent layer may have the submicron structure.

[Item 11] In any one of Items 1 to 8, the photoluminescent layer may have a flat main surface, and the light-transmissive layer may be located on the flat main surface of the photoluminescent layer and may have the submicron structure.

[Item 12] In Item 11, the light-emitting device may further include a transparent substrate that supports the photoluminescent layer.

[Item 13] In any one of Items 1 to 8, the light-transmissive layer may be a transparent substrate having the submicron structure on a main surface thereof, and the photoluminescent layer may be located on the submicron structure.

[Item 14] In Item 1 or 2, a refractive index $n_{t\text{-}a}$ of the light-transmissive layer for the first light may be higher than or equal to the refractive index $n_{wav\text{-}a}$ of the photoluminescent layer for the first light, and each of the projections or recesses in the submicron structure may have a height or depth of 150 nm or less.

[Item 15] In any one of Items 1 and 3 to 14, the submicron structure may include at least one periodic structure defined by at least the projections or recesses, and the at least one periodic structure may include a first periodic structure satisfying the following relationship: $\lambda_a/n_{wav\text{-}a}<p_a<\lambda_a$ where $p_a$ is a period of the first periodic structure.

The first periodic structure may be a one-dimensional periodic structure.

[Item 16] In Item 15, the light emitted from the photoluminescent layer may contain second light having a wavelength $\lambda_b$ different from the wavelength $\lambda_a$ in air, and the at least one periodic structure may further include a second periodic structure satisfying the following relationship: a $\lambda_b/n_{wav\text{-}b}<p_b<\lambda_b$ where $n_{wav\text{-}b}$ is a refractive index of the photoluminescent layer for the second light, and $p_b$ is a period of the second periodic structure.

The second periodic structure may be a one-dimensional periodic structure.

[Item 17] In any one of Items 1 and 3 to 14, the submicron structure may include at least two periodic structures defined by at least the projections or recesses, and the at least two periodic structures may include a two-dimensional periodic structure having periodicity in different directions.

[Item 18] In any one of Items 1 and 3 to 14, the submicron structure may include periodic structures defined by at least the projections or recesses, and the periodic structures may include periodic structures arranged in a matrix.

[Item 19] In any one of Items 1 and 3 to 14, the submicron structure may include periodic structures defined by at least the projections or recesses, and the periodic structures may include a periodic structure satisfying the following relationship: $\lambda_{ex}/n_{wav\text{-}ex}<p_{ax}<\lambda_{ex}$ where $p_{ex}$ is a period of the periodic structure, $\lambda_{ex}$ is a wavelength, in air, of excitation light for a photoluminescent material contained in the photoluminescent layer, and $n_{wax\text{-}ex}$ is a refractive index of the photoluminescent layer for the excitation light.

[Item 20]A light-emitting device includes photoluminescent layers and light-transmissive layers.

At least two of the photoluminescent layers are each independently the photoluminescent layer according to any one of Items 1 to 19, and at least two of the light-transmissive layers are each independently the light-transmissive layer according to any one of Items 1 to 19.

[Item 21] In Item 20, the photoluminescent layers and the light-transmissive layers may be stacked on top of each other.

[Item 22]A light-emitting device includes a photoluminescent layer, a light-transmissive layer located on or near the photoluminescent layer, and a submicron structure that is formed on at least one of the photoluminescent layer and the light-transmissive layer and extends in a plane of the photoluminescent layer or the light-transmissive layer.

Light is emitted to form a quasi-guided mode in the photoluminescent layer and the light-transmissive layer.

[Item 23]A light-emitting device includes a waveguide layer capable of guiding light and a periodic structure located on or near the waveguide layer.

The waveguide layer contains a photoluminescent material.

The waveguide layer forms a quasi-guided mode in which light emitted from the photoluminescent material is guided while interacting with the periodic structure.

[Item 24]A light-emitting device includes a photoluminescent layer, a light-transmissive layer located on or near the photoluminescent layer, and a submicron structure that is formed on at least one of the photoluminescent layer and the light-transmissive layer and extends in a plane of the photoluminescent layer or the light-transmissive layer.

The submicron structure has projections or recesses or both and satisfies the following relationship: $\lambda_{ex}/n_{wav\text{-}ex}<D_{int}<\lambda_{ex}$ where $D_{int}$ is a distance between adjacent projections or recesses, $\lambda_{ex}$ is a wavelength, in air, of excitation light for a photoluminescent material contained in the photoluminescent layer, and $n_{wav\text{-}ex}$ is a refractive index, for the excitation light, of a medium having the highest refractive index of media present in an optical path to the photoluminescent layer or the light-transmissive layer.

[Item 25] In Item 24, the submicron structure may include at least one periodic structure defined by at least the projections or recesses, and the at least one periodic structure may include a first periodic structure satisfying the following relationship: $\lambda_{ex}/n_{wav\text{-}ex}<p_{ex}<\lambda_{ex}$ where $p_{ax}$ is a period of the first periodic structure.

[Item 26]A light-emitting device includes a light-transmissive layer, a submicron structure that is formed in the light-transmissive layer and extends in a plane of the light-transmissive layer, and a photoluminescent layer located on or near the submicron structure, wherein the submicron structure has projections or recesses, light from the photoluminescent layer includes first light having a wavelength $\lambda_a$ in air, the submicron structure includes at least one periodic structure defined by at least the projections or recesses, and a refractive index $n_{wav\text{-}a}$ of the photoluminescent layer for the first light and a period $p_a$ of the at least one periodic structure satisfy $\lambda_a/n_{wav\text{-}a}<p_a<\lambda_a$.

[Item 27]A light-emitting device includes a photoluminescent layer, a light-transmissive layer having a higher refractive index than the photoluminescent layer, and a submicron structure that is formed in the light-transmissive layer and extends in a plane of the light-transmissive layer, wherein the submicron structure has projections or recesses, light from the photoluminescent layer includes first light having a wavelength $\lambda_a$ in air, the submicron structure includes at least one periodic structure defined by at least the projections or recesses, and a refractive index $n_{wav\text{-}a}$ of the photoluminescent layer for the first light and a period $p_a$ of the at least one periodic structure satisfy $\lambda_a/n_{wav\text{-}a}<p_a<\lambda_a$.

[Item 28]A light-emitting device includes a photoluminescent layer, and a submicron structure that is formed in the photoluminescent layer and extends in a plane of the photoluminescent layer, wherein the submicron structure has projections or recesses, light from the photoluminescent layer includes first light having a wavelength $\lambda_a$ in air, the submicron structure includes at least one periodic structure defined by at least the projections or recesses, and a refractive index $n_{wav\text{-}a}$ of the photoluminescent layer for the first light and a period $p_a$ of the at least one periodic structure satisfy $\lambda_a/n_{wav\text{-}a}<p_a<\lambda_a$.

[Item 29] The light-emitting device according to any one of Items 1 to 21 and 24 to 28, wherein the submicron structure has both the projections and the recesses.

[Item 30] The light-emitting device according to any one of Items 1 to 22 and 24 to 27, wherein the photoluminescent layer is in contact with the light-transmissive layer.

[Item 31] The light-emitting device according to Item 23, wherein the waveguide layer is in contact with the periodic structure.

[Item 32]A light-emitting apparatus includes the light-emitting device according to any one of Items 1 to 31, and an excitation light source for irradiating the photoluminescent layer with excitation light.

[Item 33]A light-emitting apparatus includes a light-emitting device, and an optical fiber for absorbing light from the light-emitting device at one end of the optical fiber and emitting the light from the other end thereof, wherein the light-emitting device includes a photoluminescent layer for emitting light including first light in response to excitation light, the first light having a wavelength $\lambda_a$ in air, a light-transmissive layer located on or near the photoluminescent layer, and a surface structure on a surface of at least one of the photoluminescent layer and the light-transmissive layer, and the surface structure has projections or recesses or both and limits a directional angle of the first light having the wavelength $\lambda_a$ in air.

[Item 34]A light-emitting apparatus includes an excitation light source, a light-emitting device, and an optical fiber for absorbing excitation light from the excitation light source at one end of the optical fiber and emitting the light from the other end thereof toward the light-emitting device, wherein the light-emitting device includes a photoluminescent layer for emitting light including first light in response to the excitation light, the first light having a wavelength $\lambda_a$ in air, a light-transmissive layer located on or near the photoluminescent layer, and a surface structure on a surface of at least one of the photoluminescent layer and the light-transmissive layer, and the surface structure has projections or recesses or both and limits a directional angle of the first light having the wavelength $\lambda_a$ in air.

[Item 35] The light-emitting apparatus according to Item 33 or 34, wherein the light-emitting device includes a first emission region for emitting light in a green wavelength band in a direction perpendicular to the photoluminescent layer and a second emission region for emitting light in a blue wavelength band in a direction perpendicular to the photoluminescent layer.

[Item 36] The light-emitting apparatus according to Item 35, wherein the first emission region includes the photoluminescent layer, the light-transmissive layer, and the surface structure, the wavelength $\lambda_a$ is in the green wavelength band, and the second emission region includes another photoluminescent layer for emitting light including second light in response to the excitation light, the second light having a wavelength $\lambda_b$ in air, another light-transmissive layer located on or near the other photoluminescent layer, and another surface structure on a surface of at least one of the other photoluminescent layer and the other light-transmissive layer, and the wavelength $\lambda_b$ is in a blue wavelength band, and the other surface structure has projections or recesses or both and limits a directional angle of the second light having the wavelength $\lambda_b$ in air.

[Item 37] The light-emitting apparatus according to Item 35 or 36, wherein the first emission region and the second emission region are arranged in a direction perpendicular to the photoluminescent layer.

[Item 38] The light-emitting apparatus according to Item 33 or 34, wherein the light-emitting device includes an emission region for emitting light in a green wavelength band in a direction perpendicular to the photoluminescent layer, and the excitation light is light in a blue wavelength band, and part of the excitation light passes perpendicularly through the photoluminescent layer.

[Item 39] The light-emitting apparatus according to Item 38, wherein the emission region includes the photoluminescent layer, the light-transmissive layer, and the surface structure, and the wavelength $\lambda_a$ is in the green wavelength band.

[Item 40] The light-emitting apparatus according to any one of Items 35 to 39, wherein the blue wavelength band ranges from 430 to 470 nm, and the green wavelength band ranges from 500 to 570 nm.

[Item 41]A light-emitting apparatus includes a light-emitting device, and at least one of a first optical fiber for absorbing light from the light-emitting device at one end of the first optical fiber and emitting the light from the other end thereof and a second optical fiber for absorbing excitation light from an excitation light source at one end of the second optical fiber and emitting the light from the other end thereof toward the light-emitting device, wherein the light-emitting device includes a light-transmissive layer, a surface structure on a surface of the light-transmissive layer, and a photoluminescent layer that is located on or near the surface structure and can emit light including first light in response to excitation light, the first light having a wavelength $\lambda_a$ in air, and the surface structure has projections or recesses or both and limits a directional angle of the first light having the wavelength $\lambda_a$ in air.

[Item 42]A light-emitting apparatus includes a light-emitting device, and at least one of a first optical fiber for absorbing light from the light-emitting device at one end of the first optical fiber and emitting the light from the other end thereof and a second optical fiber for absorbing excitation light from an excitation light source at one end of the second optical fiber and emitting the light from the other end thereof toward the light-emitting device, wherein the light-emitting device includes a photoluminescent layer for emitting light including first light in response to the excitation light, the first light having a wavelength $\lambda_a$ in air, a light-transmissive layer having a higher refractive index than the photoluminescent layer, and a surface structure on a surface of the light-transmissive layer, and the surface structure has projections or recesses or both and limits a directional angle of the first light having the wavelength $\lambda_a$ in air.

[Item 43] The light-emitting apparatus according to any one of Items 33 to 42, wherein the photoluminescent layer is in contact with the light-transmissive layer.

[Item 44]A light-emitting apparatus includes a light-emitting device, and at least one of a first optical fiber for absorbing light from the light-emitting device at one end of the first optical fiber and emitting the light from the other end thereof and a second optical fiber for absorbing excitation light from an excitation light source at one end of the second optical fiber and emitting the light from the other end thereof toward the light-emitting device, wherein the light-emitting device includes a photoluminescent layer for emitting light including first light in response to the excitation light, the first light having a wavelength $\lambda_a$ in air, and a surface structure on a surface of the photoluminescent layer, and the surface structure has projections or recesses or both and limits a directional angle of the first light having the wavelength $\lambda_a$ in air.

[Item 45] The light-emitting apparatus according to any one of Items 33 to 44, wherein a center-to-center distance $D_{int}$ between two adjacent projections or recesses in the surface structure and a refractive index $n_{wav\text{-}a}$ of the photoluminescent layer for the first light satisfy $\lambda_a/n_{wav\text{-}a}<D_{int}<\lambda_a$.

[Item 46] The light-emitting apparatus according to any one of Items 33 to 45, wherein the surface structure includes at least one periodic structure, and a period $p_a$ of the periodic structure and a refractive index $n_{wav\text{-}a}$ of the photoluminescent layer for the first light satisfy $\lambda_a/n_{wav\text{-}a}<p_a<\lambda_a$.

[Item 47] An endoscope includes the light-emitting apparatus according to any one of Items 33 to 46, and an imaging device for outputting an electric signal depending on the amount of light received, in response to light emitted from the light-emitting device in the light-emitting apparatus and reflected from an object.

[Item 48] The endoscope according to Item 47, further includes a long insert, wherein the insert includes the light-emitting device and the imaging device.

[Item 49] The endoscope according to Item 47 or 48, further includes an optical system that faces an imaging plane of the imaging device and can converge light reflected from the object onto the imaging plane.

[Item 50] An endoscope system includes the endoscope according to any one of Items 47 to 49, a processing apparatus that is electrically connected to the imaging device in the endoscope and can output an image signal based on the electric signal, and a display unit that is electrically connected to the processing apparatus and can display an image based on the image signal.

[Item 51] An optical fiber lighting apparatus includes a light source apparatus, an optical fiber coupled to the light source apparatus, and an illumination unit coupled to the optical fiber and placed in water, wherein the light source apparatus includes an excitation light source, a photoluminescent layer for emitting light including first light in response to the excitation light, the first light having a wavelength $\lambda_a$ in air, a light-transmissive layer located on or near the photoluminescent layer, and a surface structure on a surface of at least one of the photoluminescent layer and the light-transmissive layer, and the surface structure has projections or recesses or both and limits a directional angle of the first light having the wavelength $\lambda_a$ in air, the optical fiber absorbs light including the first light emitted from the photoluminescent layer at one end of the optical fiber and emits the light into the illumination unit from the other end thereof, and the illumination unit emits the light from the optical fiber into water.

[Item 52] An optical fiber lighting apparatus includes a light source apparatus, an optical fiber coupled to the light source apparatus, and an illumination unit coupled to the optical fiber and placed in space, wherein the light source apparatus includes an excitation light source, a photoluminescent layer for emitting light including first light in response to the excitation light, the first light having a wavelength $\lambda_a$ in air, a light-transmissive layer located on or near the photoluminescent layer, and a surface structure on a surface of at least one of the photoluminescent layer and the light-transmissive layer, and the surface structure has projections or recesses or both and limits a directional angle of the first light having the wavelength $\lambda_a$ in air, the optical fiber absorbs light including the first light emitted from the photoluminescent layer at one end of the optical fiber and emits the light into the illumination unit from the other end thereof, and the illumination unit emits the light from the optical fiber into space.

[Item 53] An optical fiber lighting apparatus includes a light source apparatus, an optical fiber coupled to the light source apparatus, and an illumination unit coupled to the optical fiber and placed higher than the light source apparatus, wherein the light source apparatus includes an excitation light source, a photoluminescent layer for emitting light including first light in response to the excitation light, the first light having a wavelength $\lambda_a$ in air, a light-transmissive layer located on or near the photoluminescent layer, and a surface structure on a surface of at least one of the photoluminescent layer and the light-transmissive layer, and the surface structure has projections or recesses or both and limits a directional angle of the first light having the wavelength $\lambda_a$ in air, the optical fiber absorbs light including the first light emitted from the photoluminescent layer at one end of the optical fiber and emits the light into the illumination unit from the other end thereof, and the illumination unit emits the light from the optical fiber to the outside.

[Item 54] The optical fiber lighting apparatus according to any one of Items 51 to 53, wherein the optical fiber includes a connector and is coupled to the light source apparatus and the illumination unit via the connector.

[Item 55] The optical fiber lighting apparatus according to any one of Items 51 to 54, wherein the optical fiber includes optical fiber cables and an optical divider for coupling the optical fiber cables.

[Item 56] An optical fiber sensor includes an excitation light source for emitting excitation light, a light-emitting device that is disposed on an optical path of the excitation light and can emit light in response to the excitation light, an optical shutter that is disposed on an optical path of light emitted from the light-emitting device and can switch between the light-transmitting state and the light-shielding state in response to an input drive signal, a beam splitter disposed on an optical path of the light passing through the optical shutter, an optical fiber for absorbing the light passing through the beam splitter at one end of the optical fiber, a photoreceptor for outputting a light-responsive signal depending on the intensity of light received, in response to light reflected from a deformed portion in the optical fiber and further reflected from the beam splitter, and a control circuit for inputting the drive signal into the optical shutter, wherein the control circuit determines the position of the deformed portion in the optical fiber on the basis of the delay time of the light-responsive signal relative to the drive signal, the light-emitting device includes a photoluminescent layer for emitting light including first light in response to the excitation light, the first light having a wavelength $\lambda_a$ in air, a light-transmissive layer located on or near the photoluminescent layer, and a surface structure on a surface of at least one of the photoluminescent layer and the light-transmissive layer, and the surface structure has projections or recesses or both and limits a directional angle of the first light having the wavelength $\lambda_a$ in air.

[Item 57] An optical fiber sensor includes an excitation light source for emitting excitation light, a light-emitting device that is disposed on an optical path of the excitation light and can emit light in response to the excitation light, a beam splitter disposed on an optical path of the light passing through the light-emitting device, an optical fiber for absorbing the light passing through the beam splitter at one end of the optical fiber, a photoreceptor for outputting a light-responsive signal depending on the intensity of light received, in response to light reflected from a deformed portion in the optical fiber and further reflected from the beam splitter, and a control circuit for inputting a drive signal into the excitation light source, the drive signal switching between emission and stop of the excitation light, wherein the control circuit determines the position of the deformed portion in the optical fiber on the basis of the delay time of the light-responsive signal relative to the drive signal, the light-emitting device includes a photoluminescent layer for emitting light including first light in response to the excitation light, the first light having a wavelength $\lambda_a$ in air, a light-transmissive layer located on or near the photoluminescent layer, and a surface structure on a surface of at least one of the photoluminescent layer and the light-transmissive layer, and the surface structure has projections or recesses or both and limits a directional angle of the first light having the wavelength $\lambda_a$ in air.

A light-emitting device according to an embodiment of the present disclosure includes a photoluminescent layer for emitting light having a wavelength $\lambda_a$ in air in response to the excitation light, a light-transmissive layer located on or near the photoluminescent layer, and a surface structure formed on a surface of at least one of the photoluminescent layer and the light-transmissive layer and including projections or recesses or both, wherein the surface structure limits the directional angle of the light having the wavelength $\lambda_a$ in air emitted from the photoluminescent layer. The wavelength $\lambda_a$ is, for example, within the visible wavelength range (e.g., 380 to 780 nm). When infrared light is used, the wavelength $\lambda_a$ may be more than 780 nm. When ultraviolet light is used, the wavelength $\lambda_a$ may be less than 380 nm. In the present disclosure, all electromagnetic waves, including infrared light and ultraviolet light, are referred to as "light" for convenience.

The photoluminescent layer contains a photoluminescent material. The term "photoluminescent material" refers to a material that emits light in response to excitation light. The term "photoluminescent material" encompasses fluorescent materials and phosphorescent materials in a narrow sense, encompasses inorganic materials and organic materials (e.g., dyes), and encompasses quantum dots (i.e., tiny semiconductor particles). The photoluminescent layer may contain a matrix material (host material) in addition to the photoluminescent material. Examples of matrix materials include resins and inorganic materials such as glasses and oxides.

The light-transmissive layer located on or near the photoluminescent layer is made of a material with high transmittance to the light emitted from the photoluminescent layer, for example, inorganic materials or resins. For example, the light-transmissive layer may be made of a dielectric (particularly, an insulator with low light absorption). For example, the light-transmissive layer may be a substrate that supports the photoluminescent layer. If the surface of the photoluminescent layer facing air has the submicron structure, the air layer can serve as the light-transmissive layer.

A surface structure having projections or recesses or both is formed on a surface of at least one of the photoluminescent layer and the light-transmissive layer. The term "surface", as used herein, refers to a portion in contact with another substance (i.e., an interface). If the light-transmissive layer is a gas layer, such as air, the interface between the gas layer and another substance (e.g., the photoluminescent layer) is a surface of the light-transmissive layer. This surface structure can also be referred to as a "texture". The surface structure typically has projections or recesses periodically arranged in one or two dimension. Such a surface structure can be referred to as a "periodic structure". The projections and recesses are formed at the boundary between two adjoining members (or media) having different refractive indexes. Thus, the "periodic structure" has a refractive index that varies periodically in a certain direction. The term "periodically" refers not only to periodically in the strict sense but also to approximately periodically. In the present specification, the distance between any two adjacent centers (hereinafter also referred to as the "center distance") of continuous projections or recesses in a periodic structure having a period p varies within ±15% of p.

Figure 69:
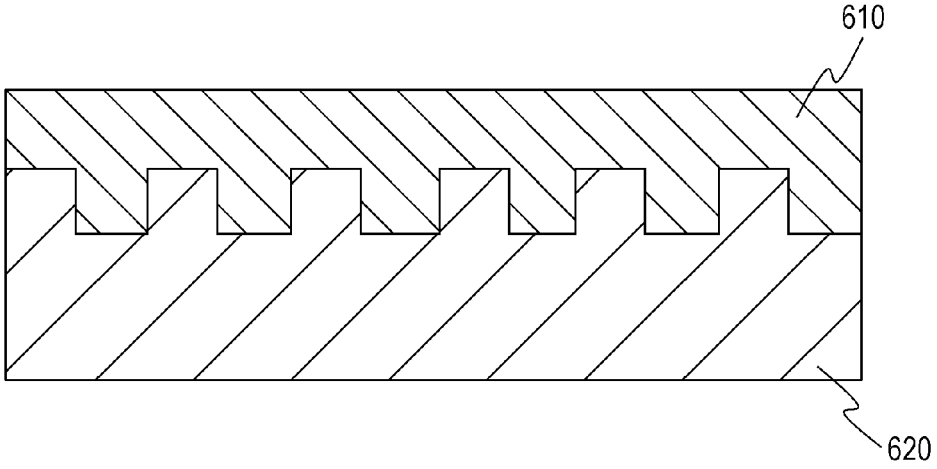

The term "projection", as used herein, refers to a raised portion higher than the reference height. The term "recess", as used herein, refers to a recessed portion lower than the reference height. When projections and recesses have a particular shape, size, or distribution, it may be difficult to distinguish between projections and recesses. For example, in a cross-sectional view of FIG. 69, a member 610 has recesses, and a member 620 has projections, or alternatively the member 610 has projections, and the member 620 has recesses. In either case, each of the member 610 and the member 620 has projections or recesses or both.

The distance between the centers of two adjacent projections or recesses in the surface structure (the period p in the case of a periodic structure) is typically shorter than the wavelength $\lambda_a$ in air of light emitted from the photoluminescent layer. The distance is submicron if light emitted from the photoluminescent layer is visible light, near-infrared light having a short wavelength, or ultraviolet light. Thus, such a surface structure is sometimes referred to as a "submicron structure". The "submicron structure" may partly have a center distance or period of more than 1 micrometer (μm). In the following description, it is assumed that the photoluminescent layer principally emits visible light, and the surface structure is principally a "submicron structure". However, the following description can also be applied to a surface structure having a micrometer structure (e.g., a micrometer structure used in combination with infrared light).

In a light-emitting device according to an embodiment of the present disclosure, a unique electric field distribution is formed inside the photoluminescent layer and the light-transmissive layer, as described in detail later with reference to the results of calculations and experiments. Such an electric field distribution is formed by an interaction between guided light and a submicron structure (i.e., a surface structure). Such an electric field distribution is formed in an optical mode referred to as a "quasi-guided mode". The quasi-guided mode can be utilized to improve the luminous efficiency, directionality, and polarization selectivity of photoluminescence, as described later. The term "quasi-guided mode" may be used in the following description to describe novel structures and/or mechanisms contemplated by the inventors. Such a description is for illustrative purposes only and is not intended to limit the present disclosure in any way.

For example, the submicron structure has projections and satisfies the relationship $\lambda_a/n_{wav\text{-}a}<D_{int}<\lambda_a$, where $D_{int}$ is the center-to-center distance between adjacent projections. Instead of the projections, the submicron structure may have recesses. For simplicity, the following description will be directed to a submicron structure having projections. The symbol $\lambda$ is the wavelength of light, and the symbol $\lambda_a$ is the wavelength of light in air. The symbol $n_{wav}$ is the refractive index of the photoluminescent layer. If the photoluminescent layer is a medium containing materials, the refractive index $n_{wav}$ is the average refractive index of the materials weighted by their respective volume fractions. Although it is desirable to use the symbol $n_{wav\text{-}a}$ to refer to the refractive index of the photoluminescent layer for light of the wavelength $\lambda_a$ because the refractive index n generally depends on the wavelength, it may be abbreviated for simplicity. The symbol $n_{wav}$ is basically the refractive index of the photoluminescent layer; however, if a layer having a higher refractive index than the photoluminescent layer is adjacent to the photoluminescent layer, the refractive index $n_{wav}$ is the average refractive index of the layer having a higher refractive index and the photoluminescent layer weighted by their respective volume fractions. This is optically equivalent to a photoluminescent layer composed of layers of different materials.

The effective refractive index $n_{eff}$ of the medium for light in the quasi-guided mode satisfies $n_a<n_{eff}<n_{wav}$, where $n_a$ is the refractive index of air. If light in the quasi-guided mode is assumed to be light propagating through the photoluminescent layer while being totally reflected at an angle of incidence $\theta$, the effective refractive index $n_{eff}$ can be written as $n_{eff}=n_{wav}\sin\theta$. The effective refractive index $n_{eff}$ is determined by the refractive index of the medium present in the region where the electric field of the quasi-guided mode is distributed. For example, if the submicron structure is formed in the light-transmissive layer, the effective refractive index $n_{eff}$ depends not only on the refractive index of the photoluminescent layer, but also on the refractive index of the light-transmissive layer. Because the electric field distribution also varies depending on the polarization direction of the quasi-guided mode (i.e., the TE mode or the TM mode), the effective refractive index $n_{eff}$ can differ between the TE mode and the TM mode.

The submicron structure is defined on at least one of the photoluminescent layer and the light-transmissive layer. If the photoluminescent layer and the light-transmissive layer are in contact with each other, the submicron structure may be defined on the interface between the photoluminescent layer and the light-transmissive layer. In this case, the photoluminescent layer and the light-transmissive layer have the submicron structure. The photoluminescent layer may have no submicron structure. In this case, a light-transmissive layer having a submicron structure is located on or near the photoluminescent layer. When the light-transmissive layer (or its submicron structure) is said to be on or near the photoluminescent layer, the distance therebetween is typically half the wavelength $\lambda_a$ or less. This allows the electric field of a guided mode to reach the submicron structure, thus forming a quasi-guided mode. However, the distance between the submicron structure of the light-transmissive layer and the photoluminescent layer may exceed half the wavelength $\lambda_a$ if the light-transmissive layer has a higher refractive index than the photoluminescent layer. If the light-transmissive layer has a higher refractive index than the photoluminescent layer, light reaches the light-transmissive layer even if the above relationship is not satisfied. In the present specification, if the photoluminescent layer and the light-transmissive layer have a positional relationship that allows the electric field of a guided mode to reach the submicron structure and form a quasi-guided mode, they may be associated with each other.

The submicron structure that satisfies $\lambda_a/n_{wav\text{-}a}<D_{int}<\lambda_a$ as described above is characterized by a submicron size in applications utilizing visible light. The submicron structure can include at least one periodic structure, as in the light-emitting devices according to the embodiments described in detail later. The at least one periodic structure satisfies the relationship $\lambda_a/n_{wav\text{-}a}\lambda_a<p_a<\lambda_a$, where $p_a$ is the period of the at least one periodic structure. That is, the submicron structure can include a periodic structure in which the center-to-center distance $D_{int}$ between adjacent projections is constant at $p_a$. If the submicron structure includes such a periodic structure, light in the quasi-guided mode propagates while repeatedly interacting with the periodic structure so that the light is diffracted by the submicron structure. Unlike the phenomenon in which light propagating through free space is diffracted by a periodic structure, this is the phenomenon in which light is guided (i.e., repeatedly totally reflected) while interacting with the periodic structure. This efficiently diffracts the light even if the periodic structure causes a small phase shift (i.e., even if the periodic structure has a small height).

The above mechanism can be utilized to improve the luminous efficiency of photoluminescence by the enhancement of the electric field due to the quasi-guided mode and also to couple the emitted light into the quasi-guided mode. The angle of travel of the light in the quasi-guided mode is varied by the angle of diffraction determined by the periodic structure. This can be utilized to output light of a particular wavelength in a particular direction. This can significantly improve directionality as compared with submicron structures including no periodic structure. Furthermore, high polarization selectivity can be simultaneously achieved because the effective refractive index $n_{eff}$ ($=n_{wav}\sin\theta$) differs between the TE mode and the TM mode. For example, as demonstrated by the experimental examples below, a light-emitting device can be provided that outputs intense linearly polarized light (e.g., the TM mode) of a particular wavelength (e.g., 610 nm) in the front direction. The directional angle of the light output in the front direction is, for example, less than 15 degrees. The term "directional angle", as used herein, refers to the angle between the direction of maximum intensity and the direction of 50% of the maximum intensity of linearly polarized light having a particular wavelength to be emitted. In other words, the term "directional angle" refers to the angle of one side with respect to the direction of maximum intensity, which is assumed to be 0 degrees. Thus, the periodic structure (i.e., surface structure) in an embodiment of the present disclosure limits the directional angle of light having a particular wavelength $\lambda_a$. In other words, the distribution of light having the wavelength $\lambda_a$ is narrowed as compared with submicron structures including no periodic structure. Such a light distribution in which the directional angle is narrowed as compared with submicron structures including no periodic structure is sometimes referred to as a "narrow-angle light distribution". Although the periodic structure in an embodiment of the present disclosure limits the directional angle of light having the wavelength $\lambda_a$, the periodic structure does not emit the entire light having the wavelength $\lambda_a$ at narrow angles. For example, in an embodiment described later in FIG. 29, light having the wavelength $\lambda_a$ is slightly emitted in a direction (e.g., at an angle in the range of 20 to 70 degrees) away from the direction of maximum intensity. However, as a whole, output light having the wavelength $\lambda_a$ mostly has an angle in the range of 0 to 20 degrees and has limited angles of directionality.

Unlike general diffraction gratings, the periodic structure in a typical embodiment of the present disclosure has a shorter period than the light wavelength $\lambda_a$. General diffraction gratings have a sufficiently longer period than the light wavelength $\lambda_a$, and consequently light having a particular wavelength is divided into diffracted light emissions, such as zero-order light (i.e., transmitted light) and ±1-order diffracted light. In such diffraction gratings, higher-order diffracted light is generated on both sides of zero-order light. Higher-order diffracted light generated on both sides of zero-order light in diffraction grating makes it difficult to provide a narrow-angle light distribution. In other words, known diffraction gratings do not have the effect of limiting the directional angle of light to a predetermined angle (e.g., approximately 15 degrees), which is a characteristic effect of an embodiment of the present disclosure. In this regard, the periodic structure according to an embodiment of the present disclosure is significantly different from known diffraction gratings.

A submicron structure having a lower periodicity results in a lower directionality, luminous efficiency, polarization, and wavelength selectivity. The periodicity of the submicron structure may be adjusted depending on the need. The periodic structure may be a one-dimensional periodic structure, which has a higher polarization selectivity, or a two-dimensional periodic structure, which allows for a lower polarization.

The submicron structure may include periodic structures. For example, these periodic structures may have different periods or different periodic directions (i.e. axes). The periodic structures may be defined on the same plane or may be stacked on top of each other. The light-emitting device may include photoluminescent layers and light-transmissive layers, and they may have submicron structures.

The submicron structure can be used not only to control the light emitted from the photoluminescent layer, but also to efficiently guide excitation light into the photoluminescent layer. That is, the excitation light can be diffracted and coupled into the quasi-guided mode to guide light in the photoluminescent layer and the light-transmissive layer by the submicron structure to efficiently excite the photoluminescent layer. A submicron structure may be used that satisfies the relationship $\lambda_{ex}/n_{wav\text{-}ex}<D_{int}<\lambda_{ex}$, where $\lambda_{ex}$ is the wavelength, in air, of the light that excites the photoluminescent material, and $n_{wav\text{-}ex}$ is the refractive index of the photoluminescent layer for the excitation light. The symbol $n_{wav\text{-}ex}$ is the refractive index of the photoluminescent layer for the emission wavelength of the photoluminescent material. Alternatively, a submicron structure may be used that includes a periodic structure satisfying the relationship $\lambda_{ex}/n_{wav\text{-}ex}<p_{ex}<\lambda_{ex}$, where $p_{ex}$ is the period of the periodic structure. The excitation light has a wavelength $\lambda_{ex}$ of, for example, 450 nm, although it may have a shorter wavelength than visible light. If the excitation light has a wavelength within the visible range, it may be output together with the light emitted from the photoluminescent layer.

2. Underlying Knowledge Forming Basis of the Present Disclosure

The underlying knowledge forming the basis for the present disclosure will be described before describing specific embodiments of the present disclosure. As described above, photoluminescent materials such as those used for fluorescent lamps and white LEDs emit light in all directions and thus require optical elements such as reflectors and lenses to emit light in a particular direction. These optical elements, however, can be eliminated (or the size thereof can be reduced) if the photoluminescent layer itself emits directional light. This results in a significant reduction in the size of optical devices and equipment. With this idea in mind, the inventors have conducted a detailed study on the photoluminescent layer to achieve directional light emission.

The inventors have investigated the possibility of inducing light emission with particular directionality so that the light emitted from the photoluminescent layer is localized in a particular direction. Based on Fermi's golden rule, the emission rate Γ, which is a measure characterizing light emission, is represented by equation (1):

$$\Gamma(r) = \frac{2\pi}{\hbar}\langle(d \cdot E(r))\rangle^2 \rho(\lambda) \tag{1}$$

In equation (1), r is the vector indicating the position, λ is the wavelength of light, d is the dipole vector, E is the electric field vector, and p is the density of states. For many substances other than some crystalline substances, the dipole vector d is randomly oriented. The magnitude of the electric field E is substantially constant irrespective of the direction if the size and thickness of the photoluminescent layer are sufficiently larger than the wavelength of light. Hence, in most cases, the value of $<(d \cdot E(r))>^2$ does not depend on the direction. Accordingly, the emission rate Γ is constant irrespective of the direction. Thus, in most cases, the photoluminescent layer emits light in all directions.

As can be seen from equation (1), to achieve anisotropic light emission, it is necessary to align the dipole vector d in a particular direction or to enhance the component of the electric field vector in a particular direction. One of these approaches can be employed to achieve directional light emission. In the present disclosure, the results of a detailed study and analysis on structures for utilizing a quasi-guided mode in which the electric field component in a particular direction is enhanced by the confinement of light in the photoluminescent layer will be described below.

3. Structure for Enhancing Only Electric Field in Particular Direction

The inventors have investigated the possibility of controlling light emission using a guided mode with an intense electric field. Light can be coupled into a guided mode using a waveguide structure that itself contains a photoluminescent material. However, a waveguide structure simply formed using a photoluminescent material outputs little or no light in the front direction because the emitted light is coupled into a guided mode. Accordingly, the inventors have investigated the possibility of combining a waveguide containing a photoluminescent material with a periodic structure. When the electric field of light is guided in a waveguide while overlapping with a periodic structure located on or near the waveguide, a quasi-guided mode is formed by the effect of the periodic structure. That is, the quasi-guided mode is a guided mode restricted by the periodic structure and is characterized in that the antinodes of the amplitude of the electric field have the same period as the periodic structure. Light in this mode is confined in the waveguide structure to enhance the electric field in a particular direction. This mode also interacts with the periodic structure to undergo diffraction so that the light in this mode is converted into light propagating in a particular direction and can thus be output from the waveguide. The electric field of light other than the quasi-guided mode is not enhanced because little or no such light is confined in the waveguide. Thus, most light is coupled into a quasi-guided mode with a large electric field component.

That is, the inventors have investigated the possibility of using a photoluminescent layer containing a photoluminescent material as a waveguide (or a waveguide layer including a photoluminescent layer) in combination with a periodic structure located on or near the waveguide to couple light into a quasi-guided mode in which the light is converted into light propagating in a particular direction, thereby providing a directional light source.

Figure 30:
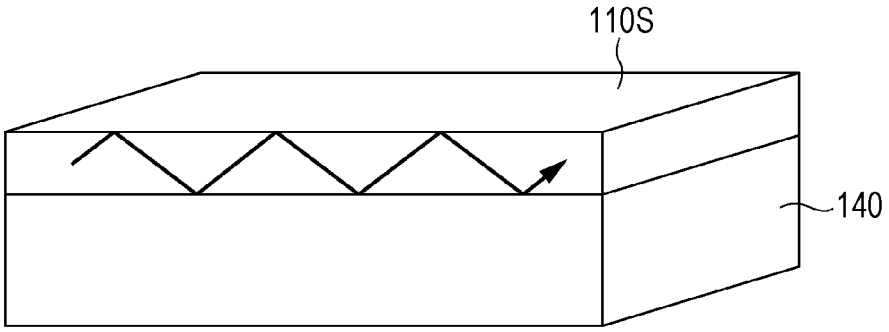
FIG. 30 is a schematic perspective view of an example slab waveguide.

As a simple waveguide structure, the inventors have studied slab waveguides. A slab waveguide has a planar structure in which light is guided. FIG. 30 is a schematic perspective view of an example slab waveguide 110S. There is a mode of light propagating through the waveguide 110S if the waveguide 110S has a higher refractive index than a transparent substrate 140 that supports the waveguide 110S. If such a slab waveguide includes a photoluminescent layer, the electric field of light emitted from an emission point overlaps largely with the electric field of a guided mode. This allows most of the light emitted from the photoluminescent layer to be coupled into the guided mode. If the photoluminescent layer has a thickness close to the wavelength of the light, a situation can be created where there is only a guided mode with a large electric field amplitude.

If a periodic structure is located on or near the photoluminescent layer, the electric field of the guided mode interacts with the periodic structure to form a quasi-guided mode. Even if the photoluminescent layer is composed of layers, a quasi-guided mode is formed as long as the electric field of the guided mode reaches the periodic structure. Not all parts of the photoluminescent layer needs to be made of a photoluminescent material; it may be a layer including at least a region that functions to emit light.

If the periodic structure is made of a metal, a mode due to the guided mode and plasmon resonance is formed. This mode has different properties from the quasi-guided mode described above and is less effective in enhancing emission because a large loss occurs due to high absorption by the metal. Thus, it is desirable to form the periodic structure using a dielectric with low absorption.

Figure 1B:
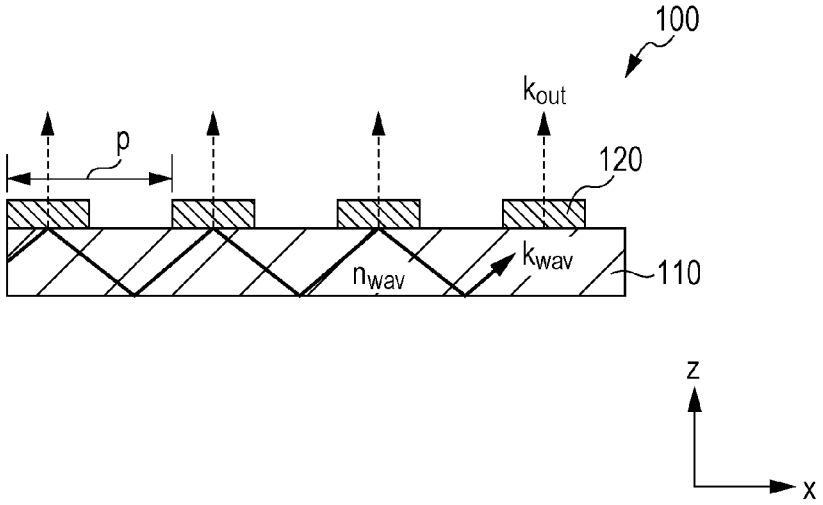
FIG. 1B is a partial sectional view of the light-emitting device shown in FIG. 1A.

The inventors have studied the coupling of light into a quasi-guided mode that can be output as light propagating in a particular angular direction using a periodic structure formed on a waveguide. FIG. 1A is a schematic perspective view of an example light-emitting device 100 including a waveguide (e.g., photoluminescent layer) 110 and a periodic structure (e.g., part of light-transmissive layer) 120. The light-transmissive layer 120 may be hereinafter referred to as "periodic structure 120" if the light-transmissive layer 120 forms a periodic structure (i.e., if a submicron structure is defined on the light-transmissive layer 120). In this example, the periodic structure 120 is a one-dimensional periodic structure in which stripe-shaped projections extending in the y direction are arranged at regular intervals in the x direction. FIG. 1B is a sectional view of the light-emitting device 100 taken along a plane parallel to the xz plane. If a periodic structure 120 having a period p is provided in contact with the waveguide 110, a quasi-guided mode having a wave number $k_{wav}$ in the in-plane direction is converted into light propagating outside the waveguide 110. The wave number $k_{out}$ of the light can be represented by equation (2):

$$k_{out} = k_{wav} - m\frac{2\pi}{p} \tag{2}$$

where m is an integer indicating the diffraction order.

For simplicity, the light guided in the waveguide 110 is assumed to be a ray of light propagating at an angle $\theta_{wav}$. This approximation gives equations (3) and (4):

$$\frac{k_{wav}\lambda_0}{2\pi} = n_{wav}\sin\theta_{wav} \tag{3}$$

$$\frac{k_{out}\lambda_0}{2\pi} = n_{out}\sin\theta_{out} \tag{4}$$

In these equations, $\lambda_0$ is the wavelength of the light in air, $n_{wav}$ is the refractive index of the waveguide 110, $n_{out}$ is the refractive index of the medium from which the light is output, and $\theta_{out}$ is the angle at which the light is output from the waveguide 110 to a substrate or air. From equations (2) to (4), the output angle $\theta_{out}$ can be represented by equation (5):

$$n_{out}\sin\theta_{out} = n_{wav}\sin\theta_{wav} - m\lambda_0/p \tag{5}$$

If $n_{wav}\sin\theta_{wav} = m\lambda_0/p$ in equation (5), $\theta_{out}=0$, meaning that the light can be output in the direction perpendicular to the plane of the waveguide 110 (i.e., in the front direction).

Based on this principle, light can be coupled into a particular quasi-guided mode and be converted into light having a particular output angle using the periodic structure to output intense light in that direction.

There are some constraints to achieving the above situation. To form a quasi-guided mode, the light propagating through the waveguide 110 has to be totally reflected. The conditions therefor are represented by inequality (6):

$$n_{out} < n_{wav}\sin\theta_{wav} \tag{6}$$

To diffract the quasi-guided mode using the periodic structure and thereby output the light from the waveguide 110, $-1<\sin\theta_{out}<1$ has to be satisfied in equation (5). Hence, inequality (7) has to be satisfied:

$$-1 < \frac{n_{wav}}{n_{out}}\sin\theta_{wav} - \frac{m\lambda_0}{n_{out}p} < 1 \tag{7}$$

Taking into account inequality (6), inequality (8) may be satisfied:

$$\frac{m\lambda_0}{2n_{out}} < p \tag{8}$$

To output the light from the waveguide 110 in the front direction (i.e., $\theta_{out}=0$), as can be seen from equation (5), equation (9) has to be satisfied:

$$p=m\lambda_0/(n_{wav}\sin\theta_{wav}) \tag{9}$$

As can be seen from equation (9) and inequality (6), the required conditions are represented by inequality (10):

$$\frac{m\lambda_0}{n_{wav}} < p < \frac{m\lambda_0}{n_{out}} \tag{10}$$

If the periodic structure 120 as shown in FIGS. 1A and 1B is provided, it may be designed based on first-order diffracted light (i.e., m=1) because higher-order diffracted light (i.e., m≥2) has low diffraction efficiency. In this embodiment, the period p of the periodic structure 120 is determined so as to satisfy inequality (11), which is given by substituting m=1 into inequality (10):

$$\frac{\lambda_0}{n_{wav}} < p < \frac{\lambda_0}{n_{out}} \tag{11}$$

If the waveguide (photoluminescent layer) 110 is not in contact with a transparent substrate, as shown in FIGS. 1A and 1B, $n_{out}$ is equal to the refractive index of air (i.e., about 1.0). Thus, the period p may be determined so as to satisfy inequality (12):

$$\frac{\lambda_0}{n_{wav}} < p < \lambda_0 \tag{12}$$

Figure 1C:
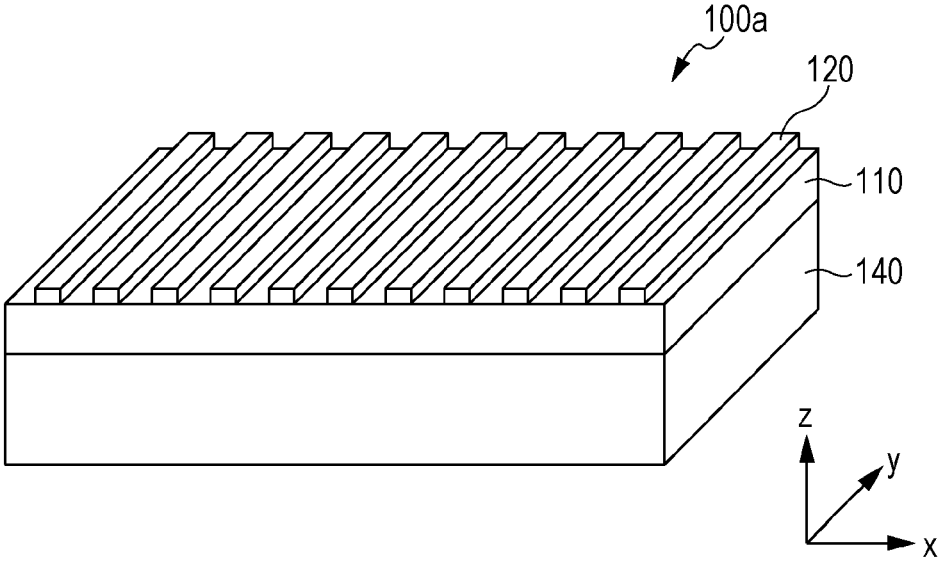
FIG. 1C is a perspective view showing the structure of a light-emitting device according to another embodiment.
Figure 1D:
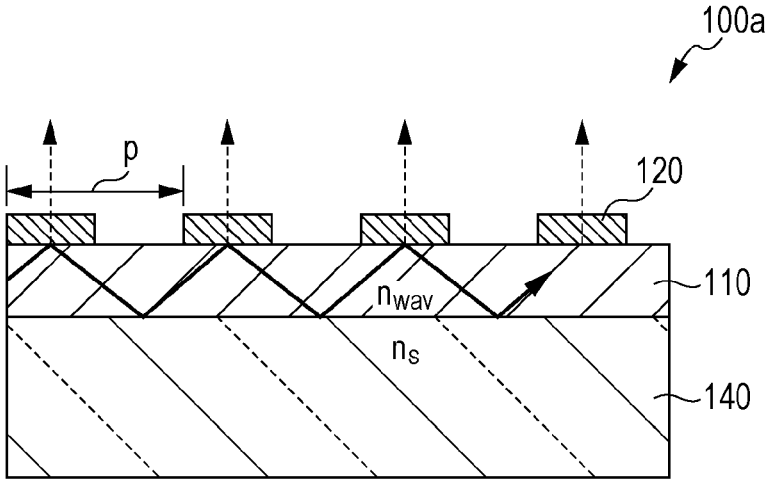
FIG. 1D is a partial sectional view of the light-emitting device shown in FIG. 1C.

Alternatively, a structure as illustrated in FIGS. 1C and 1D may be employed in which the photoluminescent layer 110 and the periodic structure 120 are formed on a transparent substrate 140. The refractive index $n_s$ of the transparent substrate 140 is higher than the refractive index of air. Thus, the period p may be determined so as to satisfy inequality (13), which is given by substituting $n_{out}=n_s$ into inequality (11):

$$\frac{\lambda_0}{n_{wav}} < p < \frac{\lambda_0}{n_s} \tag{13}$$

Although m=1 is assumed in inequality (10) to give inequalities (12) and (13), m≥2 may be assumed. That is, if both surfaces of the light-emitting device 100 are in contact with air layers, as shown in FIGS. 1A and 1B, the period p may be determined so as to satisfy inequality (14): where m is an integer of 1 or more.

$$\frac{m\lambda_0}{n_{wav}} < p < m\lambda_0 \tag{14}$$

Similarly, if the photoluminescent layer 110 is formed on the transparent substrate 140, as in the light-emitting device 100a shown in FIGS. 1C and 1D, the period p may be determined so as to satisfy inequality (15):

$$\frac{m\lambda_0}{n_{wav}} < p < \frac{m\lambda_0}{n_s} \tag{15}$$

By determining the period p of the periodic structure so as to satisfy the above inequalities, the light emitted from the photoluminescent layer 110 can be output in the front direction, thus providing a directional light-emitting device.

4. Verification by Calculations 4-1. Period and Wavelength Dependence

The inventors verified, by optical analysis, whether the output of light in a particular direction as described above is actually possible. The optical analysis was performed by calculations using DiffractMOD available from Cybernet Systems Co., Ltd. In these calculations, the change in the absorption of external light incident perpendicular to a light-emitting device by a photoluminescent layer was calculated to determine the enhancement of light output perpendicular to the light-emitting device. The calculation of the process by which external incident light is coupled into a quasi-guided mode and is absorbed by the photoluminescent layer corresponds to the calculation of a process opposite to the process by which light emitted from the photoluminescent layer is coupled into a quasi-guided mode and is converted into propagating light output perpendicular to the light-emitting device. Similarly, the electric field distribution of a quasi-guided mode was calculated from the electric field of external incident light.

Figure 2:
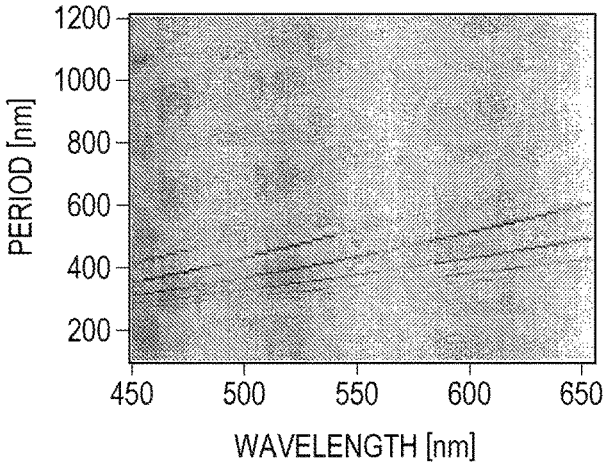
FIG. 2 is a graph showing the results of calculations of the enhancement of light output in the front direction with varying emission wavelengths and varying periods of a periodic structure.

FIG. 2 shows the results of calculations of the enhancement of light output in the front direction with varying emission wavelengths and varying periods of the periodic structure, where the photoluminescent layer was assumed to have a thickness of 1 μm and a refractive index $n_{wav}$ of 1.8, and the periodic structure was assumed to have a height of 50 nm and a refractive index of 1.5. In these calculations, the periodic structure was assumed to be a one-dimensional periodic structure uniform in the y direction, as shown in FIG. 1A, and the polarization of the light was assumed to be the TM mode, which has an electric field component parallel to the y direction. The results in FIG. 2 show that there are enhancement peaks at certain combinations of wavelength and period. In FIG. 2, the magnitude of the enhancement is expressed by different shades of color; a darker color (e.g. black) indicates a higher enhancement, whereas a lighter color (e.g. white) indicates a lower enhancement.

Figure 3:
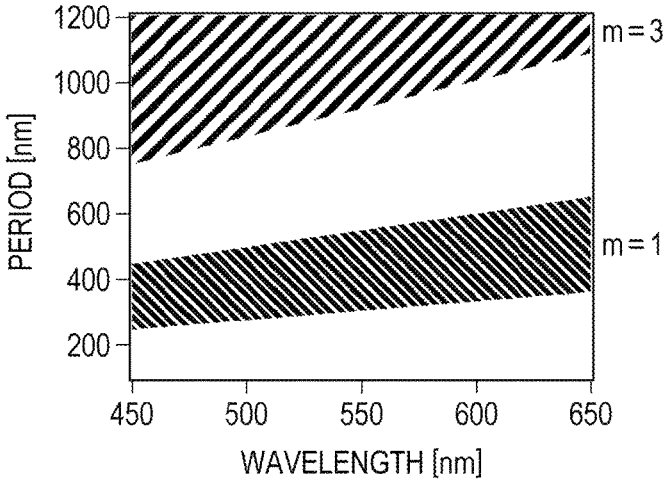
FIG. 3 is a graph illustrating the conditions for m=1 and m=3 in inequality (10)

In the above calculations, the periodic structure was assumed to have a rectangular cross section as shown in FIG. 1B. FIG. 3 is a graph illustrating the conditions for m=1 and m=3 in inequality (10). A comparison between FIGS. 2 and 3 shows that the peaks in FIG. 2 are located within the regions corresponding to m=1 and m=3. The intensity is higher for m=1 because first-order diffracted light has a higher diffraction efficiency than third- or higher-order diffracted light. There is no peak for m=2 because of low diffraction efficiency in the periodic structure.

In FIG. 2, lines are observed in each of the regions corresponding to m=1 and m=3 in FIG. 3. This indicates the presence of quasi-guided modes.

4-2. Thickness Dependence

Figure 4:
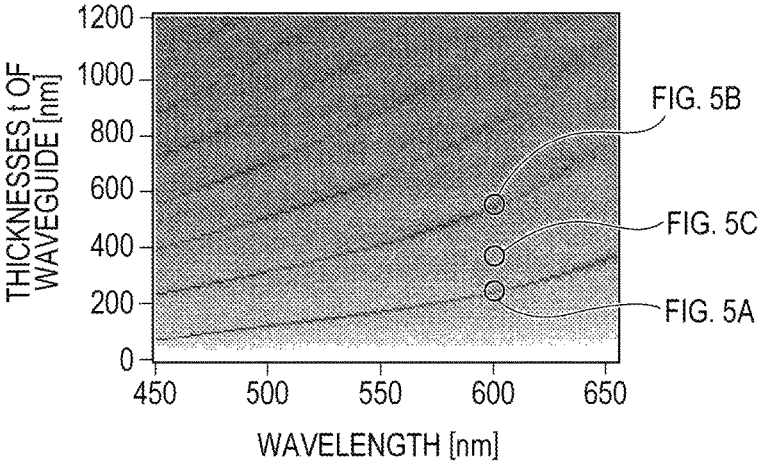
FIG. 4 is a graph showing the results of calculations of the enhancement of light output in the front direction with varying emission wavelengths and varying thicknesses t of a photoluminescent layer.

FIG. 4 is a graph showing the results of calculations of the enhancement of light output in the front direction with varying emission wavelengths and varying thicknesses t of the photoluminescent layer, where the photoluminescent layer was assumed to have a refractive index $n_{wav}$ of 1.8, and the periodic structure was assumed to have a period of 400 nm, a height of 50 nm, and a refractive index of 1.5. FIG. 4 shows that the enhancement of the light peaks at a particular thickness t of the photoluminescent layer.

Figure 5A:
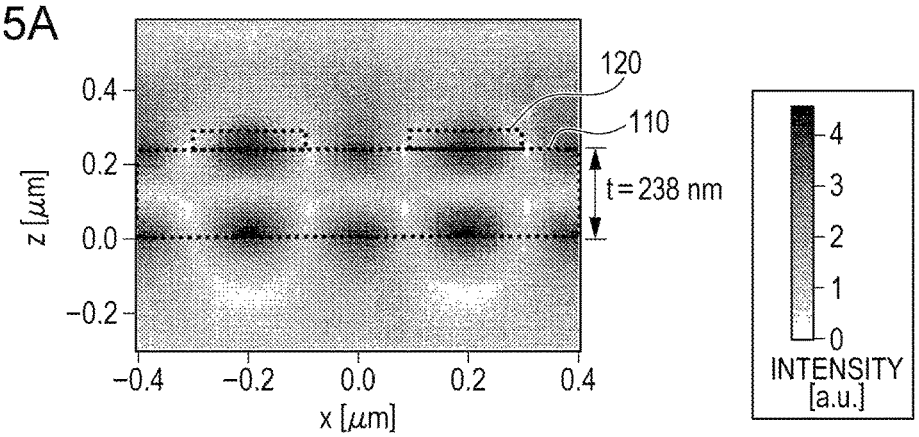
FIG. 5A is a graph showing the results of calculations of the electric field distribution of a mode to guide light in the x direction for a thickness t of 238 nm.
Figure 5B:
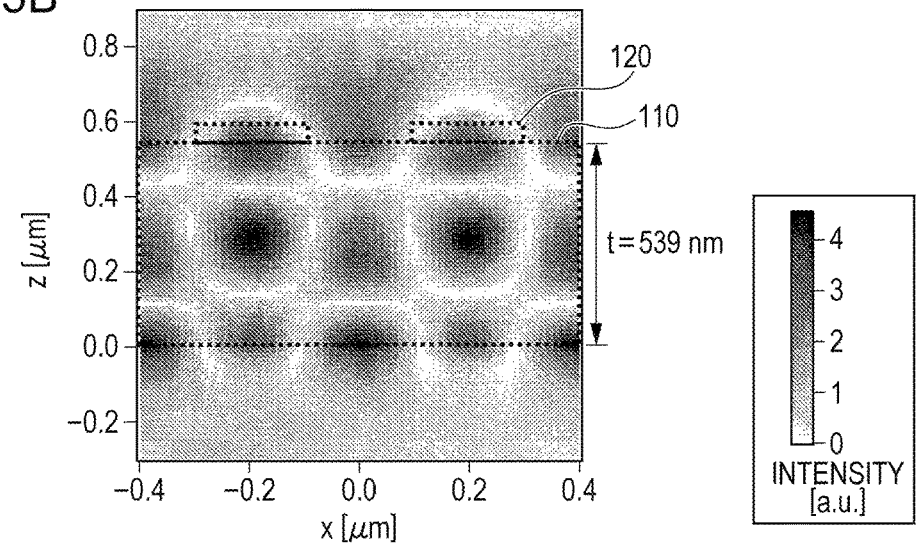
FIG. 5B is a graph showing the results of calculations of the electric field distribution of a mode to guide light in the x direction for a thickness t of 539 nm.
Figure 5C:
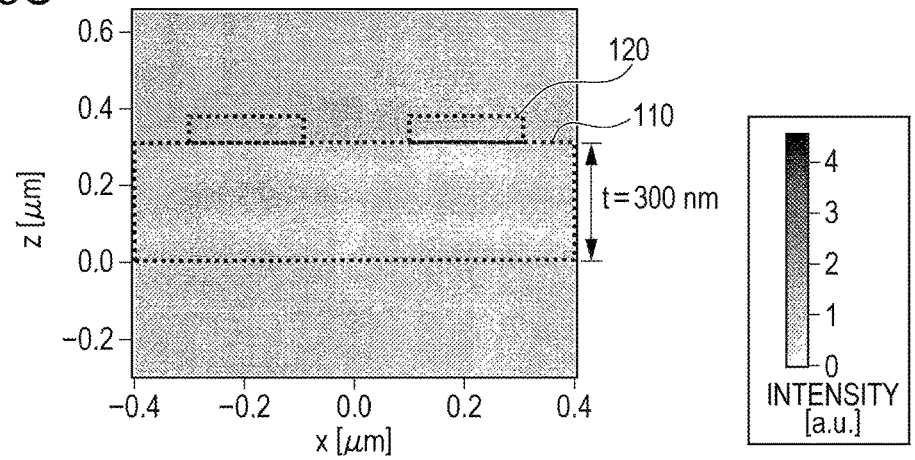
FIG. 5C is a graph showing the results of calculations of the electric field distribution of a mode to guide light in the x direction for a thickness t of 300 nm.

FIGS. 5A and 5B show the results of calculations of the electric field distributions of a mode to guide light in the x direction for a wavelength of 600 nm and thicknesses t of 238 nm and 539 nm, respectively, at which there are peaks in FIG. 4. For comparison, FIG. 5C shows the results of similar calculations for a thickness t of 300 nm, at which there is no peak. In these calculations, as in the above calculations, the periodic structure was a one-dimensional periodic structure uniform in the y direction. In each figure, a black region indicates a higher electric field intensity, whereas a white region indicates a lower electric field intensity. Whereas the results for t=238 nm and t=539 nm show high electric field intensity, the results for t=300 nm shows low electric field intensity as a whole. This is because there are guided modes for t=238 nm and t=539 nm so that light is strongly confined. Furthermore, regions with the highest electric field intensity (i.e., antinodes) are necessarily present in or directly below the projections, indicating the correlation between the electric field and the periodic structure 120. Thus, the resulting guided mode depends on the arrangement of the periodic structure 120. A comparison between the results for t=238 nm and t=539 nm shows that these modes differ in the number of nodes (white regions) of the electric field in the z direction by one.

4-3. Polarization Dependence

Figure 6:
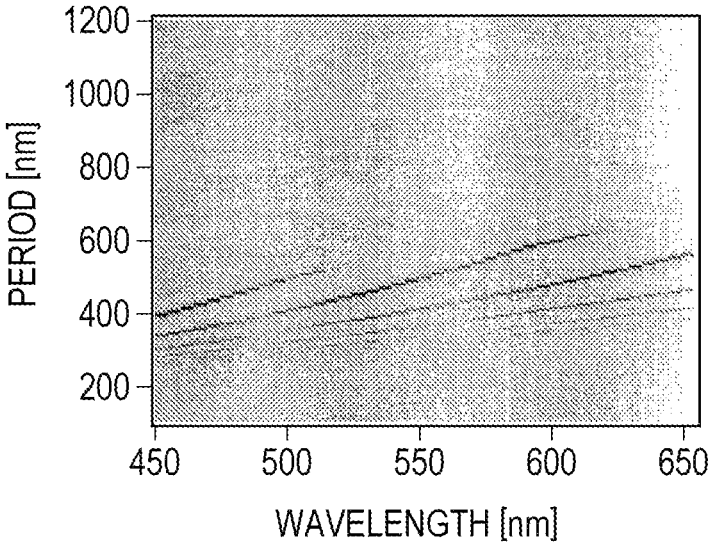
FIG. 6 is a graph showing the results of calculations of the enhancement of light performed under the same conditions as in FIG. 2 except that the polarization of the light was assumed to be the TE mode, which has an electric field component perpendicular to the y direction.

To examine the polarization dependence, the enhancement of light was calculated under the same conditions as in FIG. 2 except that the polarization of the light was assumed to be the TE mode, which has an electric field component perpendicular to the y direction. FIG. 6 shows the results of these calculations. Although the peaks in FIG. 6 differ slightly in position from the peaks for the TM mode (FIG. 2), they are located within the regions shown in FIG. 3. This demonstrates that the structure according to this embodiment is effective for both of the TM mode and the TE mode.

4-4. Two-Dimensional Periodic Structure

Figure 7A:
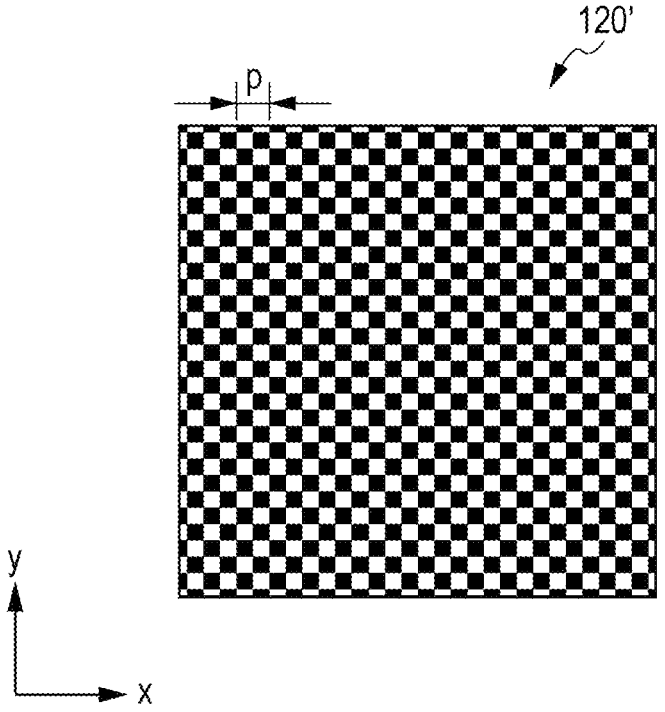
FIG. 7A is a plan view of an example two-dimensional periodic structure.
Figure 7B:
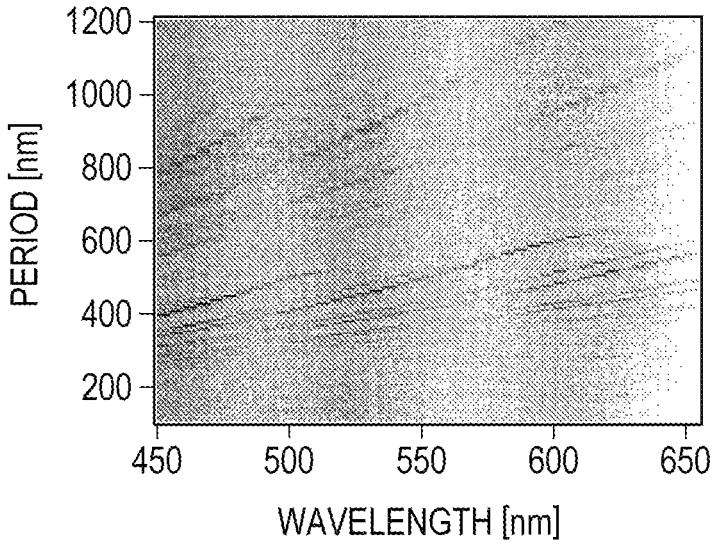
FIG. 7B is a graph showing the results of calculations performed as in FIG. 2 for the two-dimensional periodic structure.

The effect of a two-dimensional periodic structure was also studied. FIG. 7A is a partial plan view of a two-dimensional periodic structure 120' including recesses and projections arranged in both of the x direction and the y direction. In FIG. 7A, the black regions indicate the projections, and the white regions indicate the recesses. For a two-dimensional periodic structure, both of the diffraction in the x direction and the diffraction in the y direction have to be taken into account. Although the diffraction in only the x direction or the y direction is similar to that in a one-dimensional periodic structure, a two-dimensional periodic structure can be expected to give different results from a one-dimensional periodic structure because diffraction also occurs in a direction containing both of an x component and a y component (e.g., a direction inclined at 45 degrees). FIG. 7B shows the results of calculations of the enhancement of light for the two-dimensional periodic structure. The calculations were performed under the same conditions as in FIG. 2 except for the type of periodic structure. As shown in FIG. 7B, peaks matching the peaks for the TE mode in FIG. 6 were observed in addition to peaks matching the peaks for the TM mode in FIG. 2. These results demonstrate that the two-dimensional periodic structure also converts and outputs the TE mode by diffraction. For a two-dimensional periodic structure, the diffraction that simultaneously satisfies the first-order diffraction conditions in both of the x direction and the y direction also has to be taken into account. Such diffracted light is output in the direction at the angle corresponding to $\sqrt{2}$ times (i.e., $2^{1/2}$ times) the period p. Thus, peaks will occur at $\sqrt{2}$ times the period p in addition to peaks that occur in a one-dimensional periodic structure. Such peaks are observed in FIG. 7B.

Figure 18A:
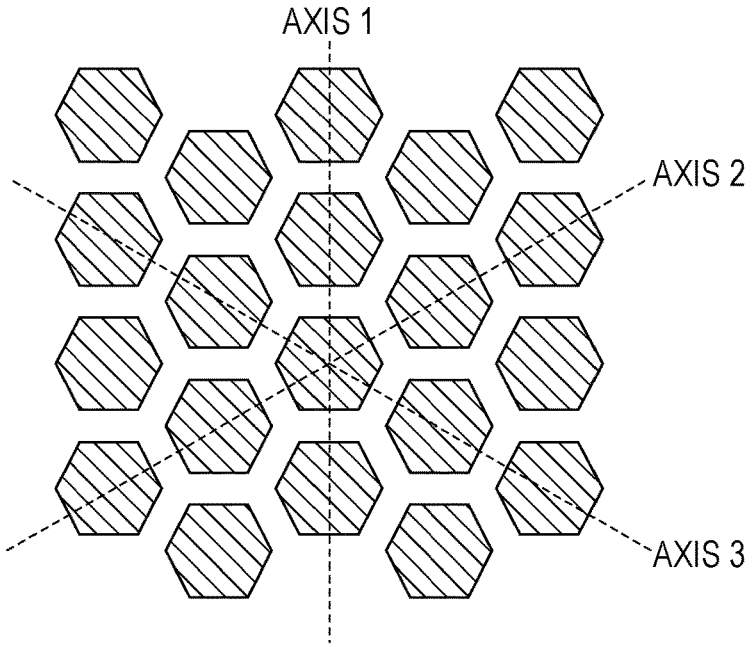
FIG. 18A is a schematic view of an example two-dimensional periodic structure.
Figure 18B:
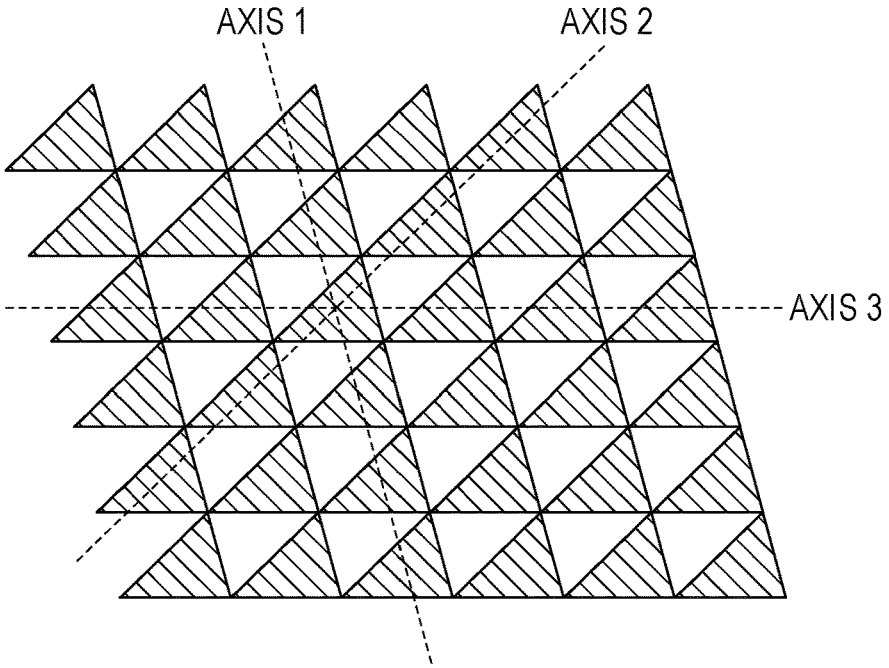
FIG. 18B is a schematic view of another example two-dimensional periodic structure.

The two-dimensional periodic structure does not have to be a square grid structure having equal periods in the x direction and the y direction, as shown in FIG. 7A, but may be a hexagonal grid structure, as shown in FIG. 18A, or a triangular grid structure, as shown in FIG. 18B. The two-dimensional periodic structure may have different periods in different directions (e.g., in the x direction and the y direction for a square grid structure).

In this embodiment, as demonstrated above, light in a characteristic quasi-guided mode formed by the periodic structure and the photoluminescent layer can be selectively output only in the front direction through diffraction by the periodic structure. With this structure, the photoluminescent layer can be excited with excitation light such as ultraviolet light or blue light to output directional light.

5. Study on Constructions of Periodic Structure and Photoluminescent Layer

The effects of changes in various conditions such as the constructions and refractive indices of the periodic structure and the photoluminescent layer will now be described.

5-1. Refractive Index of Periodic Structure

Figure 8:
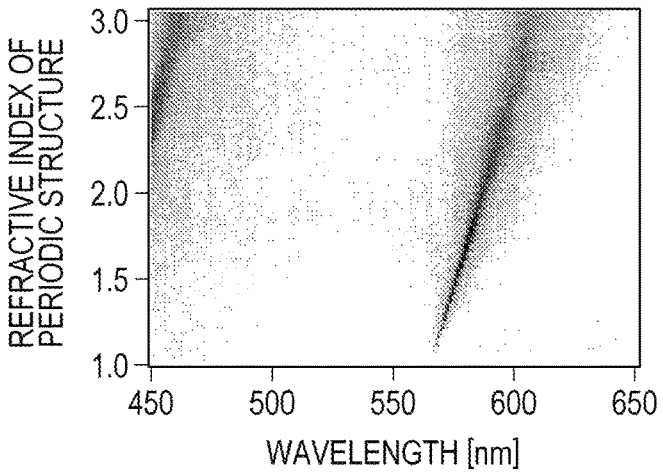
FIG. 8 is a graph showing the results of calculations of the enhancement of light output in the front direction with varying emission wavelengths and varying refractive indices of the periodic structure.
Figure 9:
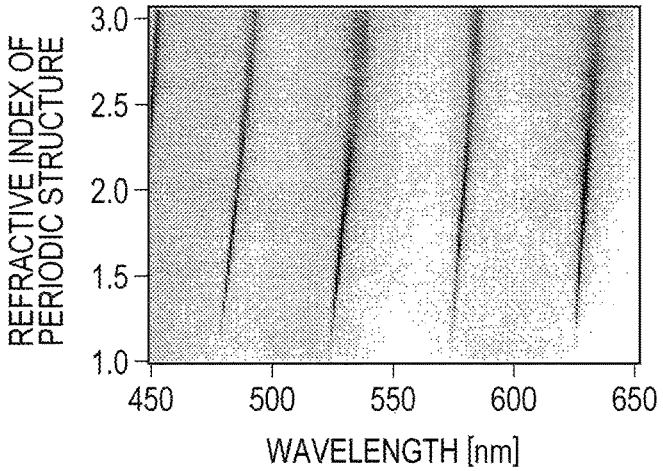
FIG. 9 is a graph showing the results obtained under the same conditions as in FIG. 8 except that the photoluminescent layer was assumed to have a thickness of 1; 000 nm.

The refractive index of the periodic structure was studied. In the calculations performed herein, the photoluminescent layer was assumed to have a thickness of 200 nm and a refractive index $n_{wav}$ of 1.8, the periodic structure was assumed to be a one-dimensional periodic structure uniform in the y direction, as shown in FIG. 1A, having a height of 50 nm and a period of 400 nm, and the polarization of the light was assumed to be the TM mode, which has an electric field component parallel to the y direction. FIG. 8 shows the results of calculations of the enhancement of light output in the front direction with varying emission wavelengths and varying refractive indices of the periodic structure. FIG. 9 shows the results obtained under the same conditions except that the photoluminescent layer was assumed to have a thickness of 1,000 nm.

The results show that a photoluminescent layer with a thickness of 1,000 nm (FIG. 9) results in a smaller shift in the wavelength at which the light intensity peaks (i.e., peak wavelength) with the change in the refractive index of the periodic structure than a photoluminescent layer with a thickness of 200 nm (FIG. 8). This is because the quasi-guided mode is more affected by the refractive index of the periodic structure as the photoluminescent layer is thinner. Specifically, a periodic structure with a higher refractive index increases the effective refractive index and thus shifts the peak wavelength toward longer wavelengths, and this effect is more noticeable as the photoluminescent layer is thinner. The effective refractive index is determined by the refractive index of the medium present in the region where the electric field of the quasi-guided mode is distributed.

The results also show that a periodic structure with a higher refractive index results in a broader peak and a lower intensity. This is because a periodic structure with a higher refractive index outputs light in the quasi-guided mode at a higher rate and is therefore less effective in confining the light, i.e., has a lower Q value. To maintain a high peak intensity, a structure may be employed in which light is moderately output using a quasi-guided mode that is effective in confining the light (i.e., has a high Q value). This means that it is undesirable to use a periodic structure made of a material having a much higher refractive index than the photoluminescent layer. Thus, to achieve a high peak intensity and Q value, the periodic structure (i.e., the light-transmissive layer) may be made of a dielectric having a refractive index lower than or similar to that of the photoluminescent layer. This is also true if the photoluminescent layer contains materials other than photoluminescent materials.

5-2. Height of Periodic Structure

Figure 10:
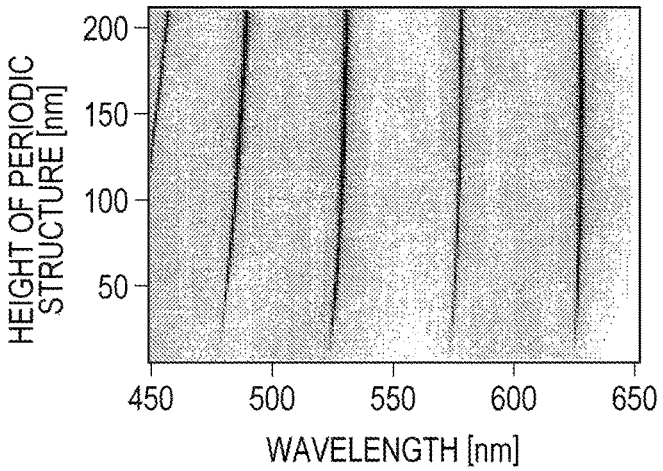
FIG. 10 is a graph showing the results of calculations of the enhancement of light output in the front direction with varying emission wavelengths and varying heights of the periodic structure.
Figure 11:
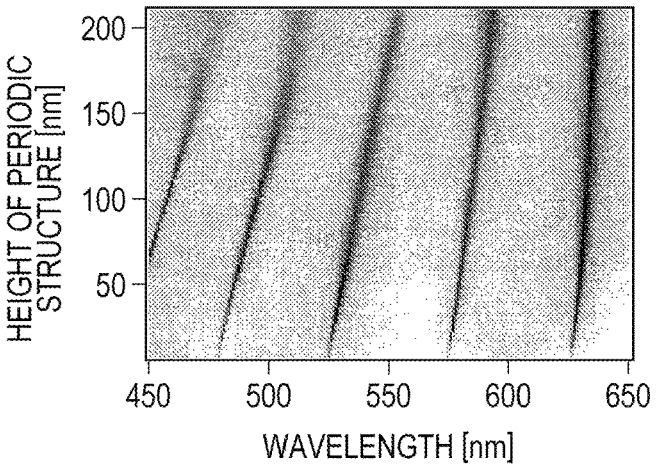
FIG. 11 is a graph showing the results of calculations performed under the same conditions as in FIG. 10 except that the periodic structure was assumed to have a refractive index $n_p$ of 2.0.

The height of the periodic structure was then studied. In the calculations performed herein, the photoluminescent layer was assumed to have a thickness of 1,000 nm and a refractive index $n_{wav}$ of 1.8, the periodic structure was assumed to be a one-dimensional periodic structure uniform in the y direction, as shown in FIG. 1A, having a refractive index $n_p$ of 1.5 and a period of 400 nm, and the polarization of the light was assumed to be the TM mode, which has an electric field component parallel to the y direction. FIG. 10 shows the results of calculations of the enhancement of light output in the front direction with varying emission wavelengths and varying heights of the periodic structure. FIG. 11 shows the results of calculations performed under the same conditions except that the periodic structure was assumed to have a refractive index $n_p$ of 2.0. Whereas the results in FIG. 10 show that the peak intensity and the Q value (i.e., the peak line width) do not change above a certain height of the periodic structure, the results in FIG. 11 show that the peak intensity and the Q value decrease with increasing height of the periodic structure. If the refractive index $n_{wav}$ of the photoluminescent layer is higher than the refractive index $n_p$ of the periodic structure (FIG. 10), the light is totally reflected, and only a leaking (i.e., evanescent) portion of the electric field of the quasi-guided mode interacts with the periodic structure. If the periodic structure has a sufficiently large height, the influence of the interaction between the evanescent portion of the electric field and the periodic structure remains constant irrespective of the height. In contrast, if the refractive index $n_{wav}$ of the photoluminescent layer is lower than the refractive index $n_p$ of the periodic structure (FIG. 11), the light reaches the surface of the periodic structure without being totally reflected and is therefore more influenced by a periodic structure with a larger height. As shown in FIG. 11, a height of about 100 nm is sufficient, and the peak intensity and the Q value decrease above a height of 150 nm. Thus, if the refractive index $n_{wav}$ of the photoluminescent layer is lower than the refractive index $n_p$ of the periodic structure, the periodic structure may have a height of 150 nm or less to achieve a high peak intensity and Q value.

5-3. Polarization Direction

Figure 12:
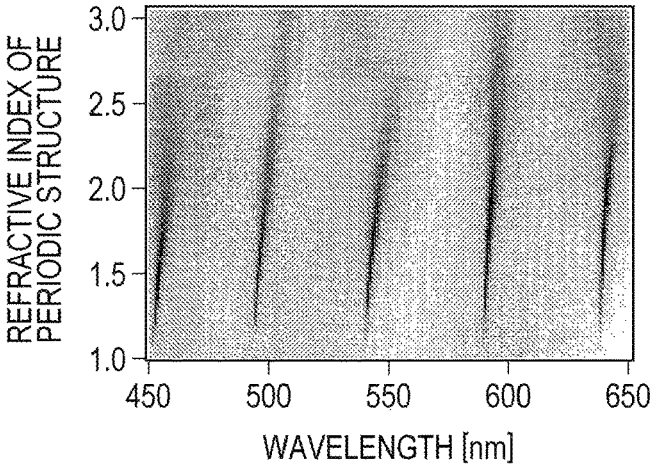
FIG. 12 is a graph showing the results of calculations performed under the same conditions as in FIG. 9 except that the polarization of the light was assumed to be the TE mode; which has an electric field component perpendicular to the y direction.

The polarization direction was then studied. FIG. 12 shows the results of calculations performed under the same conditions as in FIG. 9 except that the polarization of the light was assumed to be the TE mode, which has an electric field component perpendicular to the y direction. The TE mode is more influenced by the periodic structure than the TM mode because the electric field of the quasi-guided mode leaks more largely for the TE mode than for the TM mode. Thus, the peak intensity and the Q value decrease more significantly for the TE mode than for the TM mode if the refractive index $n_p$ of the periodic structure is higher than the refractive index $n_{wav}$ of the photoluminescent layer.

5-4. Refractive Index of Photoluminescent Layer

Figure 13:
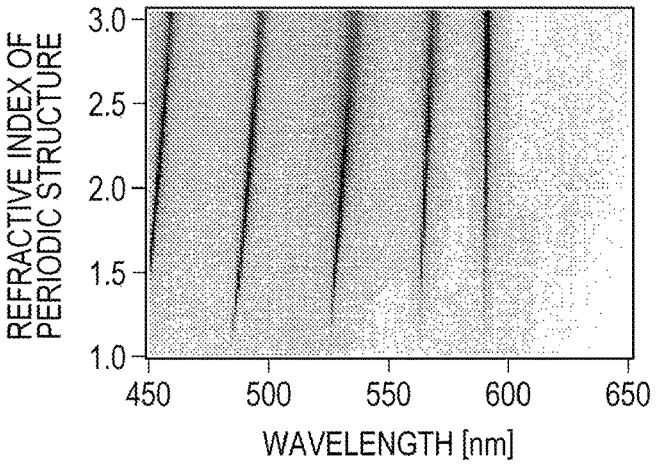
FIG. 13 is a graph showing the results of calculations performed under the same conditions as in FIG. 9 except that the photoluminescent layer was assumed to have a refractive index $n_{wav}$ of 1.5.

The refractive index of the photoluminescent layer was then studied. FIG. 13 shows the results of calculations performed under the same conditions as in FIG. 9 except that the photoluminescent layer was assumed to have a refractive index $n_{wav}$ of 1.5. The results for the photoluminescent layer having a refractive index $n_{wav}$ of 1.5 are similar to the results in FIG. 9. However, light of a wavelength of 600 nm or more was not output in the front direction. This is because, from inequality (10), $\lambda_0 < n_{wav} \times p/m = 1.5 \times 400\ nm/1 = 600\ nm$.

The above analysis demonstrates that a high peak intensity and Q value can be achieved if the periodic structure has a refractive index lower than or similar to the refractive index of the photoluminescent layer or if the periodic structure has a higher refractive index than the photoluminescent layer and a height of 150 nm or less.

6. Modifications

Modifications of this embodiment will now be described.

6-1. Structure Including Substrate

As described above, the light-emitting device may have a structure in which the photoluminescent layer 110 and the periodic structure 120 are formed on the transparent substrate 140, as shown in FIGS. 1C and 1D. Such a light-emitting device 100a may be produced by forming a thin film of the photoluminescent material for the photoluminescent layer 110 (optionally containing a matrix material; the same applies hereinafter) on the transparent substrate 140 and then forming the periodic structure 120 thereon. In this structure, the refractive index $n_5$ of the transparent substrate 140 has to be lower than or equal to the refractive index $n_{wav}$ of the photoluminescent layer 110 so that the photoluminescent layer 110 and the periodic structure 120 function to output light in a particular direction. If the transparent substrate 140 is provided in contact with the photoluminescent layer 110, the period p has to be set so as to satisfy inequality (15), which is given by replacing the refractive index $n_{out}$ of the output medium in inequality (10) by $n_s$.

Figure 14:
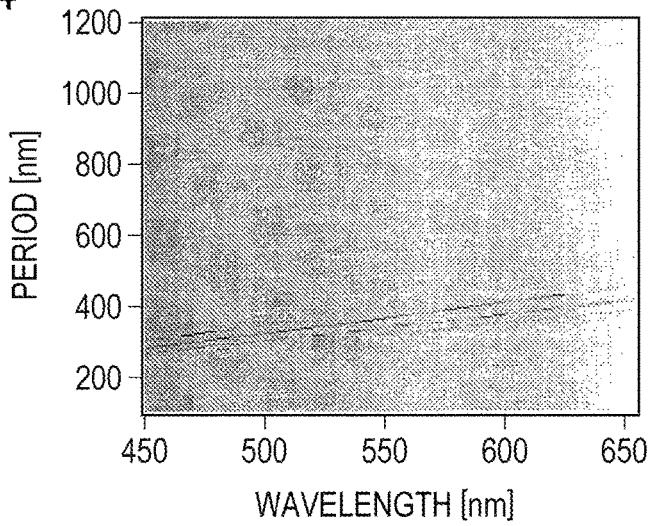
FIG. 14 is a graph showing the results of calculations performed under the same conditions as in FIG. 2 except that the photoluminescent layer and the periodic structure were assumed to be located on a transparent substrate having a refractive index of 1.5.
Figure 15:
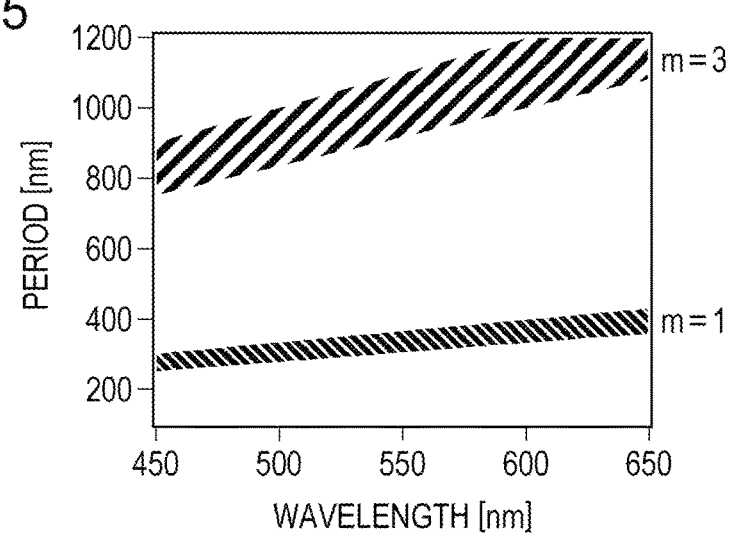
FIG. 15 is a graph illustrating the conditions represented by inequality (15)

To demonstrate this, calculations were performed under the same conditions as in FIG. 2 except that the photoluminescent layer 110 and the periodic structure 120 were assumed to be located on a transparent substrate 140 having a refractive index of 1.5. FIG. 14 shows the results of these calculations. As in the results in FIG. 2, light intensity peaks are observed at particular periods for each wavelength, although the ranges of periods where peaks appear differ from those in FIG. 2. FIG. 15 is a graph illustrating the conditions represented by inequality (15), which is given by substituting $n_{out}=n_s$ into inequality (10). In FIG. 14, light intensity peaks are observed in the regions corresponding to the ranges shown in FIG. 15.

Thus, for the light-emitting device 100a, in which the photoluminescent layer 110 and the periodic structure 120 are located on the transparent substrate 140, a period p that satisfies inequality (15) is effective, and a period p that satisfies inequality (13) is significantly effective.

6-2. Light-Emitting Apparatus Including Excitation Light Source

Figure 16:
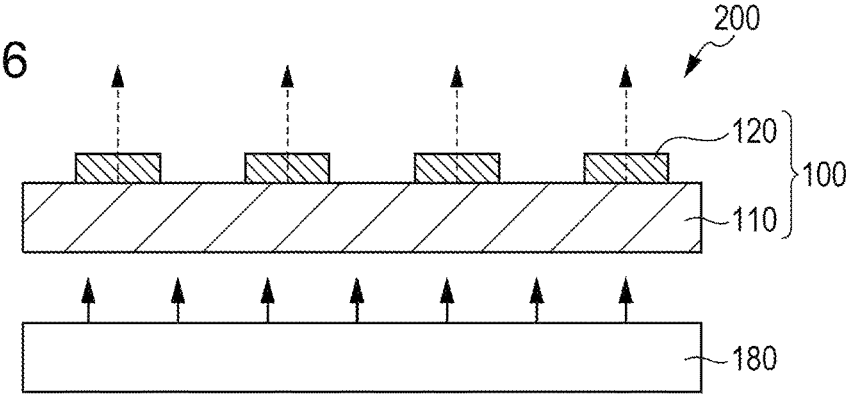
FIG. 16 is a schematic view of an example light-emitting apparatus including the light-emitting device shown in FIGS. 1A and 1B and a light source that directs excitation light into the photoluminescent layer.

FIG. 16 is a schematic view of an example light-emitting apparatus 200 including the light-emitting device 100 shown in FIGS. 1A and 1B and a light source 180 that directs excitation light into the photoluminescent layer 110. In this embodiment, as described above, the photoluminescent layer can be excited with excitation light such as ultraviolet light or blue light to output directional light. The light source 180 can be configured to emit such excitation light to provide a directional light-emitting apparatus 200. Although the wavelength of the excitation light emitted from the light source 180 is typically within the ultraviolet or blue range, it is not necessarily within these ranges, but may be determined depending on the photoluminescent material for the photoluminescent layer 110. Although the light source 180 illustrated in FIG. 16 is configured to direct excitation light into the bottom surface of the photoluminescent layer 110, it may be configured otherwise, for example, to direct excitation light into the top surface of the photoluminescent layer 110. Excitation light may be directed at an angle (i.e., obliquely) with respect to a direction perpendicular to a main surface (the top surface or the bottom surface) of the photoluminescent layer 110. Excitation light directed obliquely so as to be totally reflected in the photoluminescent layer 110 can more efficiently induce light emission.

Figure 17A:
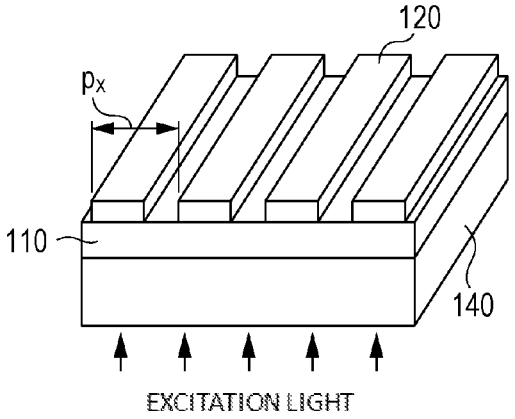
FIG. 17A is a schematic view of a one-dimensional periodic structure having a period $p_x$ in the x direction.
Figure 17B:
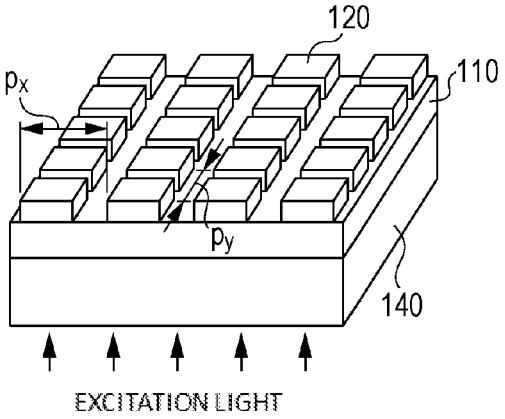
FIG. 17B is a schematic view of a two-dimensional periodic structure having a period $p_x$ in the x direction and a period $p_y$ in the y direction.

The excitation light may be coupled into a quasi-guided mode to efficiently output light. This method is illustrated in FIGS. 17A to 17D. In this example, as in the structure shown in FIGS. 1C and 1D, the photoluminescent layer 110 and the periodic structure 120 are formed on the transparent substrate 140. As shown in FIG. 17A, the period $p_x$ in the x direction is first determined so as to enhance light emission. As shown in FIG. 17B, the period $p_y$ in they direction is then determined so as to couple the excitation light into a quasi-guided mode. The period $p_x$ is determined so as to satisfy the conditions given by replacing p in inequality (10) by $p_x$. The period $p_y$ is determined so as to satisfy inequality (16): where m is an integer of 1 or more, $\lambda_{ex}$ is the wavelength of the excitation light, and $n_{out}$ is the refractive index of the medium having the highest refractive index of the media in contact with the photoluminescent layer 110 except the periodic structure 120.

$$\frac{m\lambda_{ex}}{n_{wav}} < p_y < \frac{m\lambda_{ex}}{\lambda} \tag{16}$$

In the example in FIG. 17B, $n_{out}$ is the refractive index $n_s$ of the transparent substrate 140. For a structure including no transparent substrate 140, as illustrated in FIG. 16, $n_{out}$ is the refractive index of air (i.e., about 1.0).

In particular, the excitation light can be more effectively converted into a quasi-guided mode if m=1, i.e., if the period $p_y$ is determined so as to satisfy inequality (17):

$$\frac{\lambda_{ex}}{n_{wav}} < p_y < \frac{\lambda_{ex}}{n_{out}} \tag{17}$$

Thus, the excitation light can be converted into a quasi-guided mode if the period $p_y$ is set so as to satisfy the conditions represented by inequality (16) (particularly, the conditions represented by inequality (17)). As a result, the photoluminescent layer 110 can efficiently absorb the excitation light of the wavelength $\lambda_{ex}$.

Figure 17C:
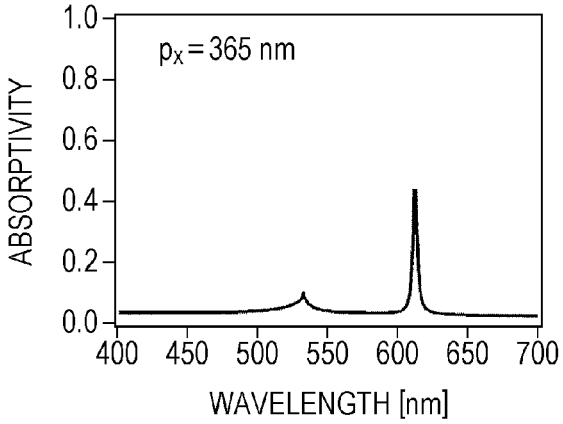
FIG. 17C is a graph showing the wavelength dependence of light absorptivity in the structure illustrated in FIG. 17A.
Figure 17D:
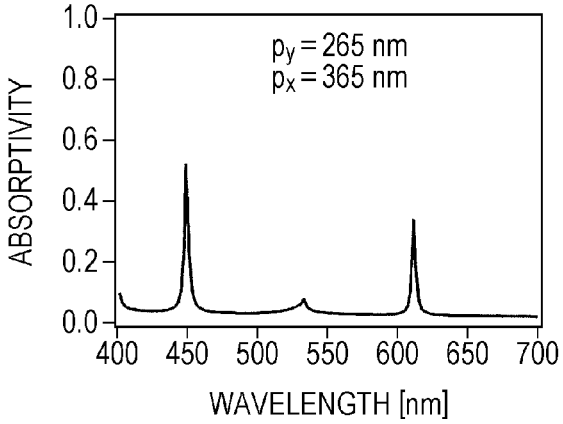
FIG. 17D is a graph showing the wavelength dependence of light absorptivity in the structure illustrated in FIG. 17B.

FIGS. 17C and 17D are the results of calculations of the proportion of absorbed light to light incident on the structures shown in FIGS. 17A and 17B, respectively, for each wavelength. In these calculations, $p_x$=365 nm, $p_y$=265 nm, the photoluminescent layer 110 was assumed to have an emission wavelength $\lambda$ of about 600 nm, the excitation light was assumed to have a wavelength $\lambda_{ex}$ of about 450 nm, and the photoluminescent layer 110 was assumed to have an extinction coefficient of 0.003. As shown in FIG. 17D, the photoluminescent layer 110 has high absorptivity not only for the light emitted from the photoluminescent layer 110, but also for the excitation light, i.e., light of a wavelength of about 450 nm. This indicates that the incident light is effectively converted into a quasi-guided mode to increase the proportion of the light absorbed into the photoluminescent layer 110. The photoluminescent layer 110 also has high absorptivity for the emission wavelength, i.e., about 600 nm. This indicates that light of a wavelength of about 600 nm incident on this structure is similarly effectively converted into a quasi-guided mode. The periodic structure 120 shown in FIG. 17B is a two-dimensional periodic structure including structures having different periods (i.e., different periodic components) in the x direction and the y direction. Such a two-dimensional periodic structure including periodic components allows for high excitation efficiency and high output intensity. Although the excitation light is incident on the transparent substrate 140 in FIGS. 17A and 17B, the same effect can be achieved if the excitation light is incident on the periodic structure 120.

Also available are two-dimensional periodic structures including periodic components as shown in FIGS. 18A and 18B. The structure shown in FIG. 18A includes periodically arranged projections or recesses having a hexagonal planar shape. The structure shown in FIG. 18B includes periodically arranged projections or recesses having a triangular planar shape. These structures have major axes (axes 1 to 3 in the examples in FIGS. 18A and 18B) that can be assumed to be periods. Thus, different periods can be assigned to different axial directions. These periods may be set so as to increase the directionality of light of different wavelengths or to efficiently absorb the excitation light. In any case, each period is set so as to satisfy the conditions corresponding to inequality (10).

6-3. Periodic Structure on Transparent Substrate

Figure 19A:
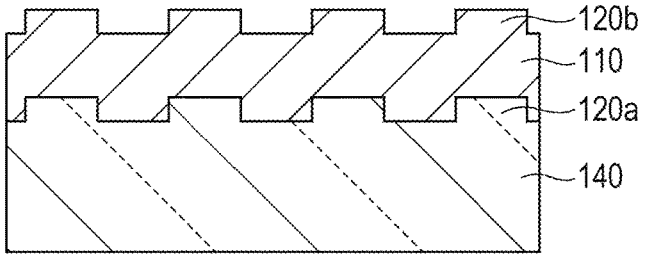
FIG. 19A is a schematic view of a modification in which the periodic structure is formed on the transparent substrate.
Figure 19B:
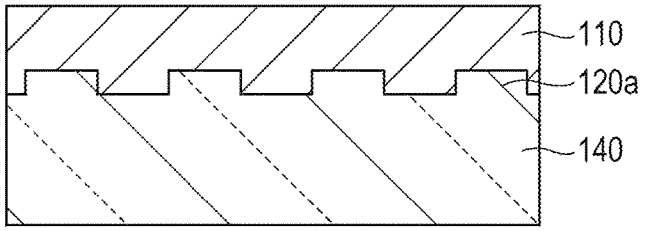
FIG. 19B is a schematic view of another modification in which the periodic structure is formed on the transparent substrate.

As shown in FIGS. 19A and 19B, a periodic structure 120a may be formed on the transparent substrate 140, and the photoluminescent layer 110 may be located thereon. In the example in FIG. 19A, the photoluminescent layer 110 is formed along the texture of the periodic structure 120a on the transparent substrate 140. As a result, a periodic structure 120b with the same period is formed in the surface of the photoluminescent layer 110. In the example in FIG. 19B, the surface of the photoluminescent layer 110 is planarized. In these examples, directional light emission can be achieved by setting the period p of the periodic structure 120a so as to satisfy inequality (15).

Figure 19C:
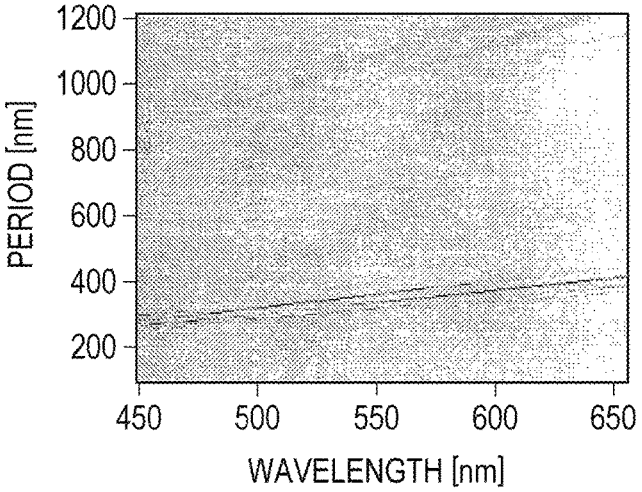
FIG. 19C is a graph showing the results of calculations of the enhancement of light output from the structure in FIG. 19A in the front direction with varying emission wavelengths and varying periods of the periodic structure.

To verify the effect of these structures, the enhancement of light output from the structure in FIG. 19A in the front direction was calculated with varying emission wavelengths and varying periods of the periodic structure. In these calculations, the photoluminescent layer 110 was assumed to have a thickness of 1,000 nm and a refractive index $n_{wav}$ of 1.8, the periodic structure 120a was assumed to be a one-dimensional periodic structure uniform in the y direction having a height of 50 nm, a refractive index $n_p$ of 1.5, and a period of 400 nm, and the polarization of the light was assumed to be the TM mode, which has an electric field component parallel to the y direction. FIG. 19C shows the results of these calculations. In these calculations, light intensity peaks were observed at the periods that satisfy the conditions represented by inequality (15).

6-4. Powder

According to the above embodiment, light of any wavelength can be enhanced by adjusting the period of the periodic structure and the thickness of the photoluminescent layer. For example, if the structure shown in FIGS. 1A and 1B is formed using a photoluminescent material that emits light over a wide wavelength range, only light of a certain wavelength can be enhanced. Accordingly, the structure of the light-emitting device 100 as shown in FIGS. 1A and 1B may be provided in powder form for use as a fluorescent material. Alternatively, the light-emitting device 100 as shown in FIGS. 1A and 1B may be embedded in resin or glass.

Figure 20:
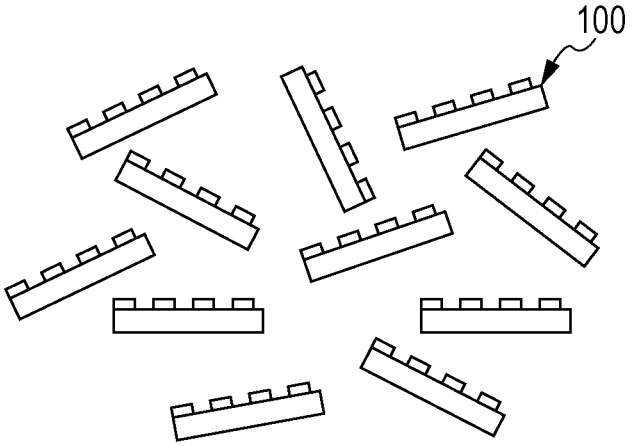
FIG. 20 is a schematic view of a mixture of light-emitting devices in powder form.

The single structure as shown in FIGS. 1A and 1B can output only light of a certain wavelength in a particular direction and is therefore not suitable for outputting, for example, white light, which has a wide wavelength spectrum. Accordingly, as shown in FIG. 20, light-emitting devices 100 that differ in the conditions such as the period of the periodic structure and the thickness of the photoluminescent layer may be mixed in powder form to provide a light-emitting apparatus with a wide wavelength spectrum. In this case, the individual light-emitting devices 100 have sizes of, for example, several micrometers to several millimeters in one direction and can include, for example, one- or two-dimensional periodic structures with several periods to several hundreds of periods.

6-5. Array of Structures with Different Periods

Figure 21:
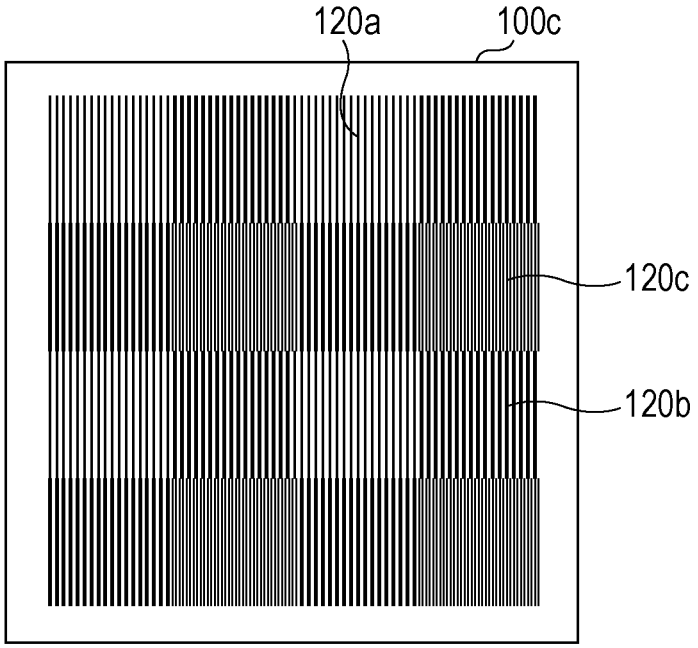
FIG. 21 is a plan view of an example two-dimensional array of periodic structures having different periods on the photoluminescent layer.

FIG. 21 is a plan view of an example two-dimensional array of periodic structures having different periods on the photoluminescent layer. In this example, three types of periodic structures 120a, 120b, and 120c are arranged without any space therebetween. The periods of the periodic structures 120a, 120b, and 120c are set so as to output, for example, light in the red, green, and blue wavelength ranges, respectively, in the front direction. Thus, structures having different periods can be arranged on the photoluminescent layer to output directional light with a wide wavelength spectrum. The periodic structures are not necessarily configured as described above, but may be configured in any manner.

6-6. Layered Structure

Figure 22:
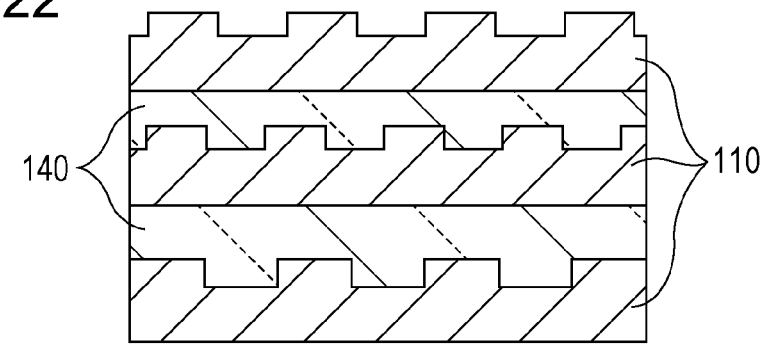
FIG. 22 is a schematic view of an example light-emitting device having a layered structure including photoluminescent layers having a texture formed thereon.

FIG. 22 shows an example light-emitting device having a layered structure including photoluminescent layers 110 having a texture formed thereon and transparent substrates 140 between the photoluminescent layers 110. The texture formed on the photoluminescent layer 110 in each layer corresponds to a periodic structure or a submicron structure. The example in FIG. 22 includes three periodic structures having different periods. The periods of these periodic structures are set so as to output light in the red, green, and blue wavelength ranges in the front direction. The photoluminescent layer 110 in each layer is made of a material that emits light of the color corresponding to the period of the periodic structure in that layer. Thus, periodic structures having different periods can be stacked on top of each other to output directional light with a wide wavelength spectrum.

The number of layers and the constructions of the photoluminescent layer 110 and the periodic structure in each layer are not limited to those described above, but may be selected as appropriate. For example, for a structure including two layers, first and second photoluminescent layers are formed opposite each other with a light-transmissive substrate therebetween, and first and second periodic structures are formed on the surfaces of the first and second photoluminescent layers, respectively. In this case, the first photoluminescent layer and the first periodic structure may together satisfy the conditions corresponding to inequality (15), whereas the second photoluminescent layer and the second periodic structure may together satisfy the conditions corresponding to inequality (15). For a structure including three or more layers, the photoluminescent layer and the periodic structure in each layer may satisfy the conditions corresponding to inequality (15). The positional relationship between the photoluminescent layers and the periodic structures in FIG. 22 may be reversed. Although the layers illustrated by the example in FIG. 22 have different periods, they may all have the same period. In this case, although the spectrum cannot be broadened, the emission intensity can be increased.

6-7. Structure Including Protective Layer

Figure 23:
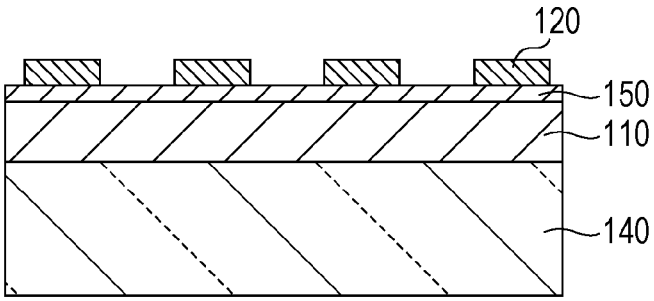
FIG. 23 is a sectional view of an example structure including a protective layer between the photoluminescent layer and the periodic structure.

FIG. 23 is a sectional view of an example structure including a protective layer 150 between the photoluminescent layer 110 and the periodic structure 120. The protective layer 150 may be provided to protect the photoluminescent layer 110. However, if the protective layer 150 has a lower refractive index than the photoluminescent layer 110, the electric field of the light leaks into the protective layer 150 only by about half the wavelength. Thus, if the protective layer 150 is thicker than the wavelength, no light reaches the periodic structure 120. As a result, there is no quasi-guided mode, and the function of outputting light in a particular direction cannot be achieved. If the protective layer 150 has a refractive index higher than or similar to that of the photoluminescent layer 110, the light reaches the interior of the protective layer 150; therefore, there is no limitation on the thickness of the protective layer 150. Nevertheless, a thinner protective layer 150 is desirable because more light is output if most of the portion in which light is guided (this portion is hereinafter referred to as "waveguide layer") is made of a photoluminescent material. The protective layer 150 may be made of the same material as the periodic structure (light-transmissive layer) 120. In this case, the light-transmissive layer 120 having the periodic structure functions as a protective layer. The light-transmissive layer 120 desirably has a lower refractive index than the photoluminescent layer 110.

7. Materials

Directional light emission can be achieved if the photoluminescent layer (or waveguide layer) and the periodic structure are made of materials that satisfy the above conditions. The periodic structure may be made of any material. However, a photoluminescent layer (or waveguide layer) or a periodic structure made of a medium with high light absorption is less effective in confining light and therefore results in a lower peak intensity and Q value. Thus, the photoluminescent layer (or waveguide layer) and the periodic structure may be made of media with relatively low light absorption.

For example, the periodic structure may be made of a dielectric with low light absorption. Examples of candidate materials for the periodic structure include magnesium fluoride ($MgF_2$), lithium fluoride (LiF), calcium fluoride ($CaF_2$), quartz ($SiO_2$), glasses, resins, magnesium oxide (MgO), indium tin oxide (ITO), titanium oxide ($TiO_2$), silicon nitride (SiN), tantalum pentoxide ($Ta_2O_5$), zirconia ($ZrO_2$), zinc selenide (ZnSe), and zinc sulfide (ZnS). To form a periodic structure having a lower refractive index than the photoluminescent layer, as described above, $MgF_2$, LiF, $CaF_2$, $SiO_2$, glasses, and resins are desirably used, which have refractive indices of about 1.3 to 1.5.

The term "photoluminescent material" encompasses fluorescent materials and phosphorescent materials in a narrow sense, encompasses inorganic materials and organic materials (e.g., dyes), and encompasses quantum dots (i.e., tiny semiconductor particles). In general, a fluorescent material containing an inorganic host material tends to have a higher refractive index. Examples of fluorescent materials that emit blue light include $M_{10}(PO_4)_6Cl_2:Eu^{2+}$ (where M is at least one element selected from Ba, Sr, and Ca), $BaMgAl_{10}O_{17}:Eu^{2}+$, $M_3MgSi_2O_8:Eu^{2+}$ (where M is at least one element selected from Ba, Sr, and Ca), and $M_5SiO_4Cl_6:Eu^{2+}$ (where M is at least one element selected from Ba, Sr, and Ca). Examples of fluorescent materials that emit green light include $M_2MgSi_2O_7:Eu^{2+}$ (where M is at least one element selected from Ba, Sr, and Ca), $SrSi_5AlO_2N_7:Eu^{2+}$, $SrSi_2O_2N_2:Eu^{2+}$, $BaAl_2O_4:Eu^{2+}$, $BaZrSi_3O_9:Eu^{2+}$, $M_2SiO_4:Eu^{2+}$ (where M is at least one element selected from Ba, Sr, and Ca), $BaSi_3O_4N_2:Eu^{2+}$, $Ca_8Mg(SiO_4)_4Cl_2:Eu^{2+}$, $Ca_3SiO_4Cl_2:Eu^{2+}$, $CaSi_{12-(m+n)}Al_{(m+n)}O_nN_{16-n}:Ce^{3+}$, and β-SiAlON:$Eu^{2+}$. Examples of fluorescent materials that emit red light include $CaAlSiN_3:Eu^{2+}$, $SrAlSi_4O_7:Eu^{2+}$, $M_2Si_5N_8:Eu^{2+}$ (where M is at least one element selected from Ba, Sr, and Ca), $MSiN_2:Eu^{2+}$ (where M is at least one element selected from Ba, Sr, and Ca), $MSi_2O_2N_2:Yb^{2+}$ (where M is at least one element selected from Sr and Ca), $Y_2O_2S:Eu^{3+}$, $Sm^{3+}$, $La_2O_2S:Eu^{3+}$, $Sm^{3+}$, $CaWO_4:Li^{1+}$, $Eu^{3+}$, $Sm^{3+}$, $M_2SiS_4:Eu^{2+}$ (where M is at least one element selected from Ba, Sr, and Ca), and $M_3SiO_5:Eu^{2+}$ (where M is at least one element selected from Ba, Sr, and Ca). Examples of fluorescent materials that emit yellow light include $Y_3Al_5O_{12}:Ce^{3+}$, $CaSi_2O_2N_2:Eu^{2+}$, $Ca_3Sc_2Si_3O_{12}:Ce^{3+}$, $CaSc_2O_4:Ce^{3+}$, α-SiAlON:$Eu^{2+}$, $MSi_2O_2N_2:Eu^{2+}$ (where M is at least one element selected from Ba, Sr, and Ca), and $M_7(SiO_3)_6Cl_2:Eu^{2+}$ (where M is at least one element selected from Ba, Sr, and Ca).

Examples of quantum dots include materials such as CdS, CdSe, core-shell CdSe/ZnS, and alloy CdSSe/ZnS. Light of various wavelengths can be emitted depending on the material. Examples of matrices for quantum dots include glasses and resins.

The transparent substrate 140, as shown in, for example, FIGS. 1C and 1D, is made of a light-transmissive material having a lower refractive index than the photoluminescent layer 110. Examples of such materials include $MgF_2$, LiF, $CaF_2$, $SiO_2$, glasses, and resins. In structures in which excitation light enters the photoluminescent layer 110 without passing through the substrate 140, the substrate 140 is not necessarily transparent. For example, the substrate 140 may be formed of $BaF_2$, $SrF_2$, MgO, $MgAl_2O_4$, sapphire ($Al_2O_3$), $SrTiO_3$, $LaAlO_3$, $TiO_2$, $Gd_3Ga_5O_{12}$, $LaSrAlO_4$, $LaSrGaO_4$, $LaTaO_3$, SrO, yttria-stabilized zirconia (YSZ) $ZrO_2.Y_2O_3$, yttrium-aluminum-garnet (YAG), or $Tb_3Ga_5O_{12}$.

8. Method of Manufacture

Example methods of manufacture will now be described.

Figure 24:
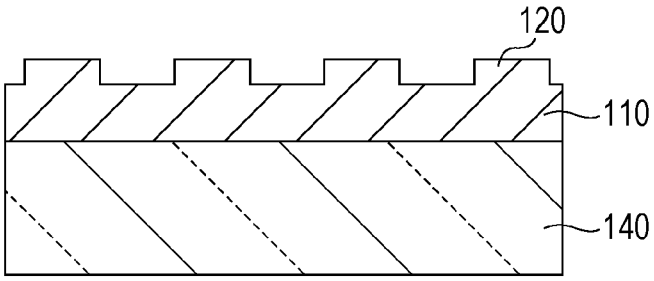
FIG. 24 is a sectional view of an example where the periodic structure is formed by partially processing the photoluminescent layer.

An example method for manufacturing the structure shown in FIGS. 1C and 1D includes depositing a thin film of fluorescent material on the transparent substrate 140 by a process such as evaporation, sputtering, or coating to form the photoluminescent layer 110 and then depositing a dielectric and patterning it by a process such as photolithography to form the periodic structure 120. Alternatively, the periodic structure 120 may be formed by nanoimprinting. As shown in FIG. 24, the periodic structure 120 may also be formed by partially processing the photoluminescent layer 110. In this case, the periodic structure 120 is made of the same material as the photoluminescent layer 110.

The light-emitting device 100 shown in FIGS. 1A and 1B can be manufactured, for example, by fabricating the light-emitting device 100a shown in FIGS. 1C and 1D and then stripping the photoluminescent layer 110 and the periodic structure 120 from the substrate 140.

The structure shown in FIG. 19A can be manufactured, for example, by forming the periodic structure 120a on the transparent substrate 140 by a process such as a semiconductor process or nanoimprinting and then depositing thereon the material for the photoluminescent layer 110 by a process such as evaporation or sputtering. The structure shown in FIG. 19B can be manufactured by filling the recesses in the periodic structure 120a with the photoluminescent layer 110 by a process such as coating.

The above methods of manufacture are for illustrative purposes only, and the light-emitting devices according to the embodiments of the present disclosure may be manufactured by other methods.

9. Experimental Examples

Light-emitting devices according to embodiments of the present disclosure are illustrated by the following examples.

A sample light-emitting device having the structure as illustrated in FIG. 19A was prepared and evaluated for its properties. The light-emitting device was prepared as described below.

Figure 25:
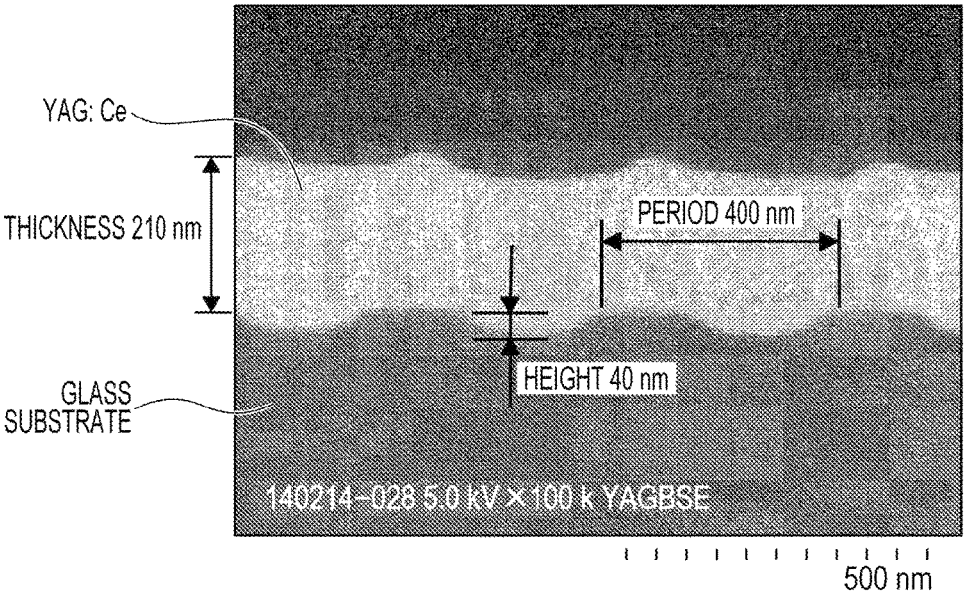
FIG. 25 is a cross-sectional transmission electron microscopy (TEM) image of a photoluminescent layer formed on a glass substrate having a periodic structure.
Figure 26:
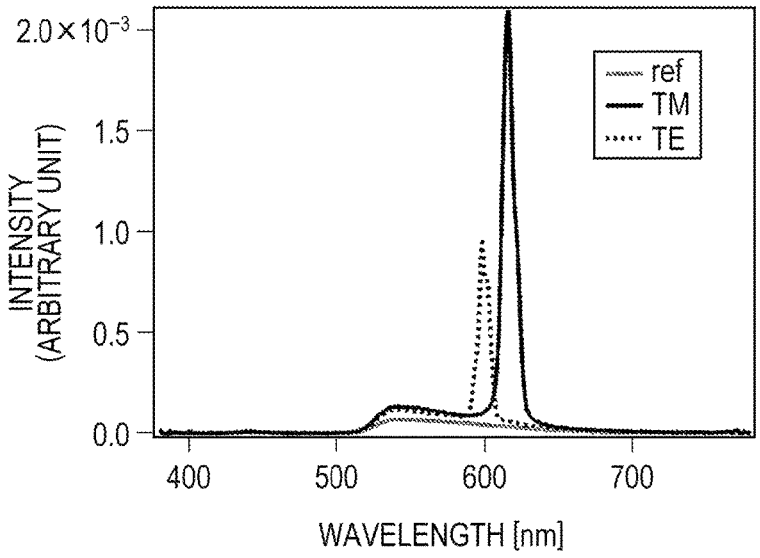
FIG. 26 is a graph showing the results of measurements of the spectrum of light output from a sample light-emitting device in the front direction.

A one-dimensional periodic structure (stripe-shaped projections) having a period of 400 nm and a height of 40 nm was formed on a glass substrate, and a photoluminescent material, i.e., YAG:Ce, was deposited thereon to a thickness of 210 nm. FIG. 25 shows a cross-sectional transmission electron microscopy (TEM) image of the resulting light-emitting device. FIG. 26 shows the results of measurements of the spectrum of light emitted from the light-emitting device in the front direction when YAG:Ce was excited with an LED having an emission wavelength of 450 nm. FIG. 26 shows the results (ref) for a light-emitting device including no periodic structure, the results for the TM mode, and the results for the TE mode. The TM mode has a polarization component parallel to the one-dimensional periodic structure. The TE mode has a polarization component perpendicular to the one-dimensional periodic structure. The results show that the intensity of light of a particular wavelength in the case with the periodic structure is significantly higher than without a periodic structure. The results also show that the light enhancement effect is greater for the TM mode, which has a polarization component parallel to the one-dimensional periodic structure.

Figure 27A:
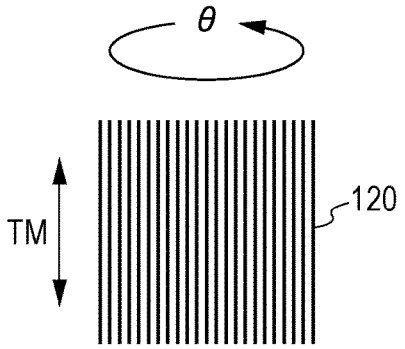
FIG. 27A is a schematic view of a light-emitting device that can emit linearly polarized light of the TM mode, rotated about an axis parallel to the line direction of the one-dimensional periodic structure.
Figure 27B:
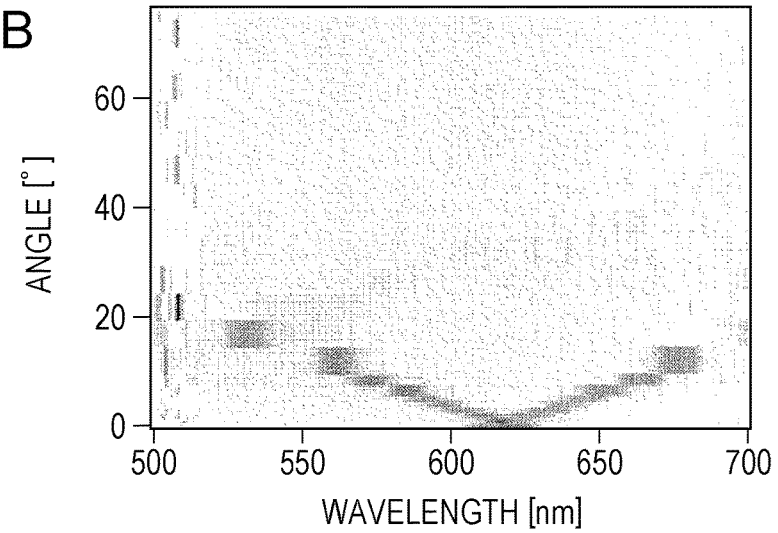
FIG. 27B is a graph showing the results of measurements of the angular dependence of light output from the sample light-emitting device rotated as illustrated in FIG. 27A.
Figure 27C:
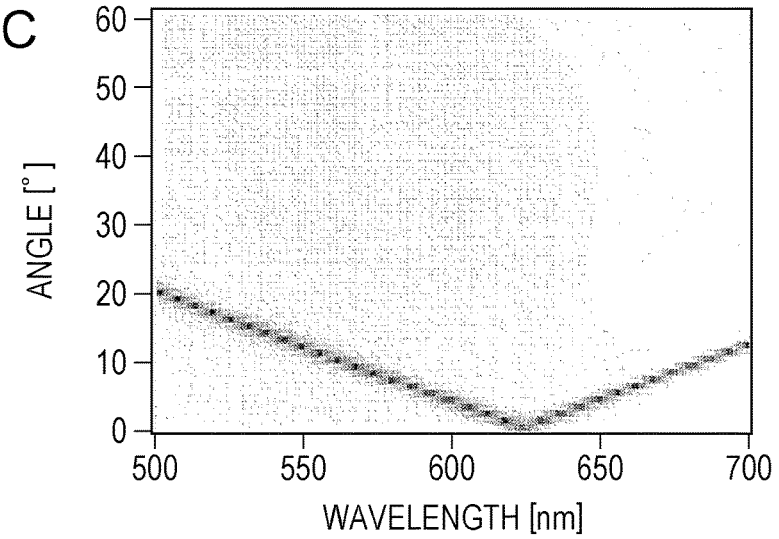
FIG. 27C is a graph showing the results of calculations of the angular dependence of light output from the sample light-emitting device rotated as illustrated in FIG. 27A.
Figure 27D:
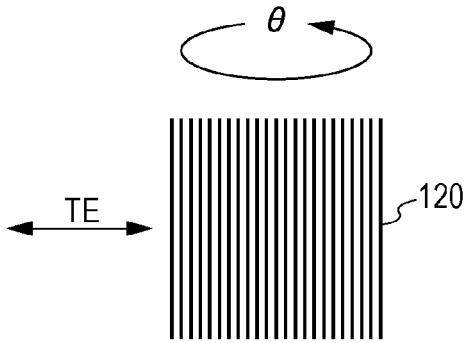
FIG. 27D is a schematic view of a light-emitting device that can emit linearly polarized light of the TE mode, rotated about an axis parallel to the line direction of the one-dimensional periodic structure.
Figure 27E:
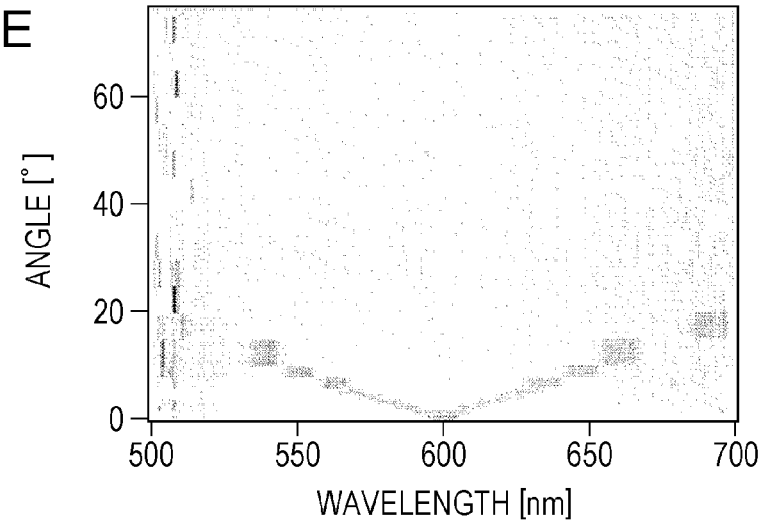
FIG. 27E is a graph showing the results of measurements of the angular dependence of light output from the sample light-emitting device rotated as illustrated in FIG. 270D.
Figure 27F:
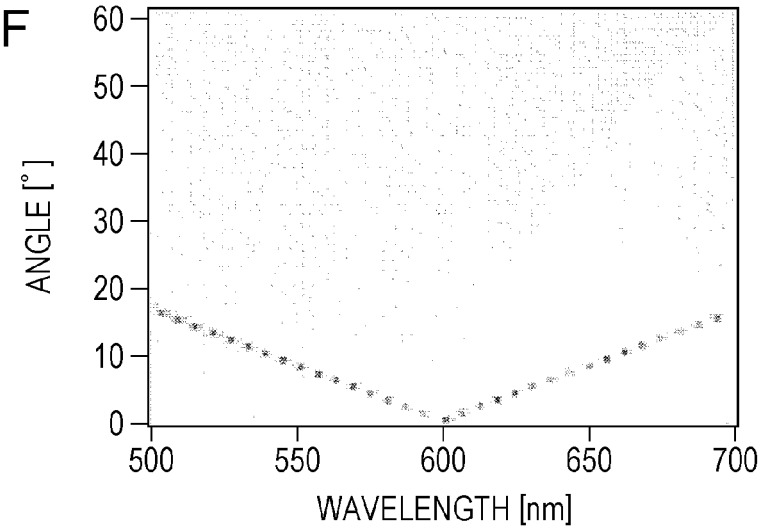
FIG. 27F is a graph showing the results of calculations of the angular dependence of light output from the sample light-emitting device rotated as illustrated in FIG. 27D.
Figure 28A:
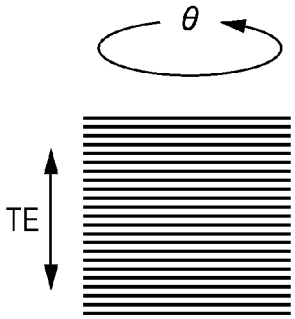
FIG. 28A is a schematic view of a light-emitting device that can emit linearly polarized light of the TE mode, rotated about an axis perpendicular to the line direction of the one-dimensional periodic structure.
Figure 28B:
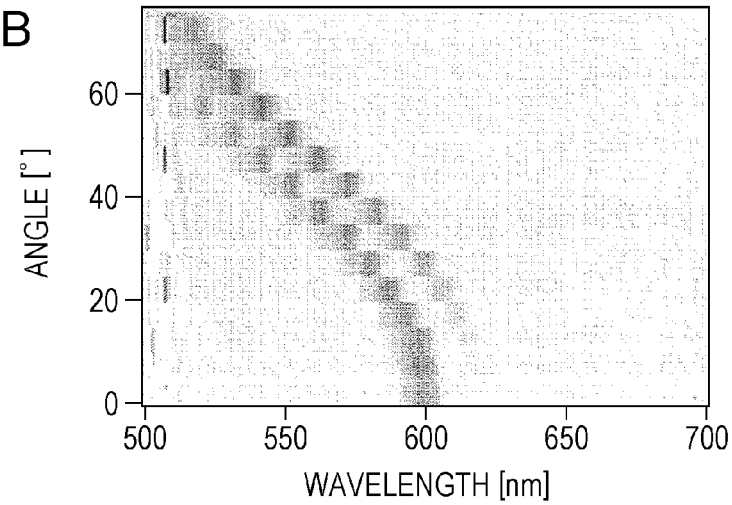
FIG. 28B is a graph showing the results of measurements of the angular dependence of light output from the sample light-emitting device rotated as illustrated in FIG. 28A.
Figure 28C:
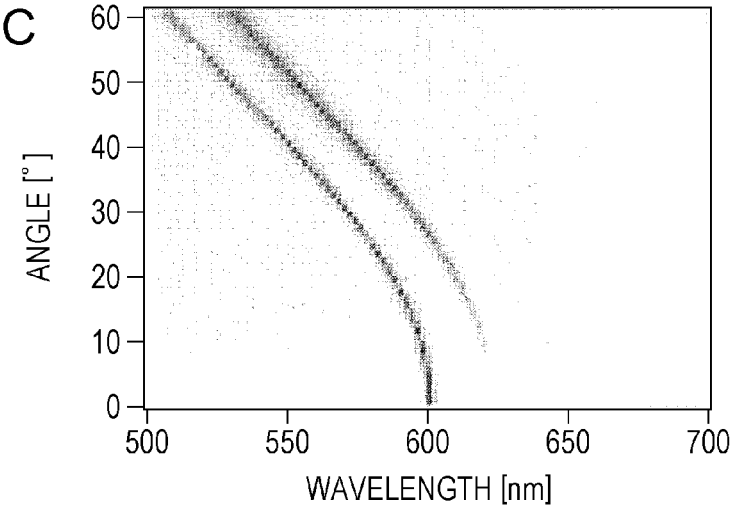
FIG. 28C is a graph showing the results of calculations of the angular dependence of light output from the sample light-emitting device rotated as illustrated in FIG. 28A.
Figure 28D:
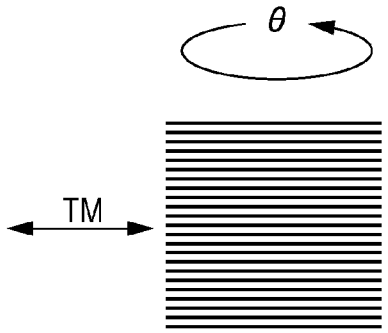
FIG. 28D is a schematic view of a light-emitting device that can emit linearly polarized light of the TM mode, rotated about an axis perpendicular to the line direction of the one-dimensional periodic structure.
Figure 28E:
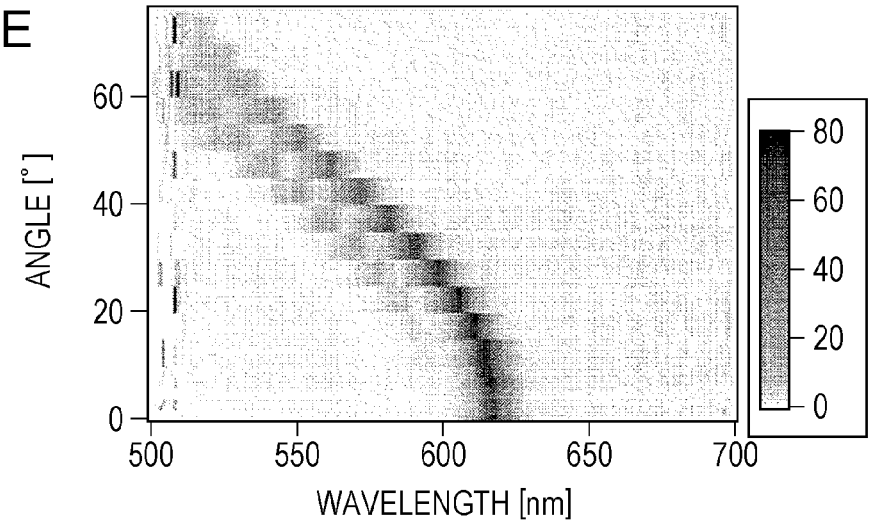
FIG. 28E is a graph showing the results of measurements of the angular dependence of light output from the sample light-emitting device rotated as illustrated in FIG. 28D.
Figure 28F:
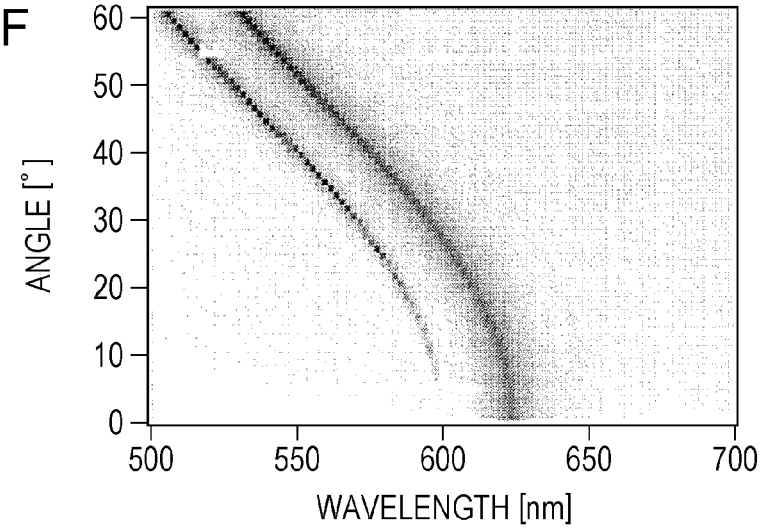
FIG. 28F is a graph showing the results of calculations of the angular dependence of light output from the sample light-emitting device rotated as illustrated in FIG. 28D.

FIGS. 27A to 27F and FIGS. 28A to 28F show the results of measurements and calculations of the angular dependence of the intensity of light output from the same sample. FIG. 27A illustrates a light-emitting device that can emit linearly polarized light of the TM mode, rotated about an axis parallel to the line direction of the one-dimensional periodic structure 120. FIGS. 27B and 27C show the results of measurements and calculations for the rotation. FIG. 27D illustrates a light-emitting device that can emit linearly polarized light of the TE mode, rotated about an axis parallel to the line direction of the one-dimensional periodic structure 120. FIGS. 27E and 27F show the results of measurements and calculations for the rotation. FIG. 28A illustrates a light-emitting device that can emit linearly polarized light of the TE mode, rotated about an axis perpendicular to the line direction of the one-dimensional periodic structure 120. FIGS. 28B and 28C show the results of measurements and calculations for the rotation. FIG. 28D illustrates a light-emitting device that can emit linearly polarized light of the TM mode, rotated about an axis perpendicular to the line direction of the one-dimensional periodic structure 120. FIGS. 28E and 28F show the results of measurements and calculations for the rotation. As can be seen from FIGS. 27A to 27F and FIGS. 28A to 28F, the enhancement effect is greater for the TM mode, and the enhanced wavelength shifts with angle. For example, light of a wavelength of 610 nm is observed only in the TM mode and in the front direction, indicating that the light is directional and polarized. Furthermore, the results of measurements and the results of calculations match each other in FIGS. 27B and 27C, FIGS. 27E and 27F, FIGS. 28B and 28C, or FIGS. 28E and 28F. Thus, the validity of the above calculations was experimentally demonstrated.

Figure 29:
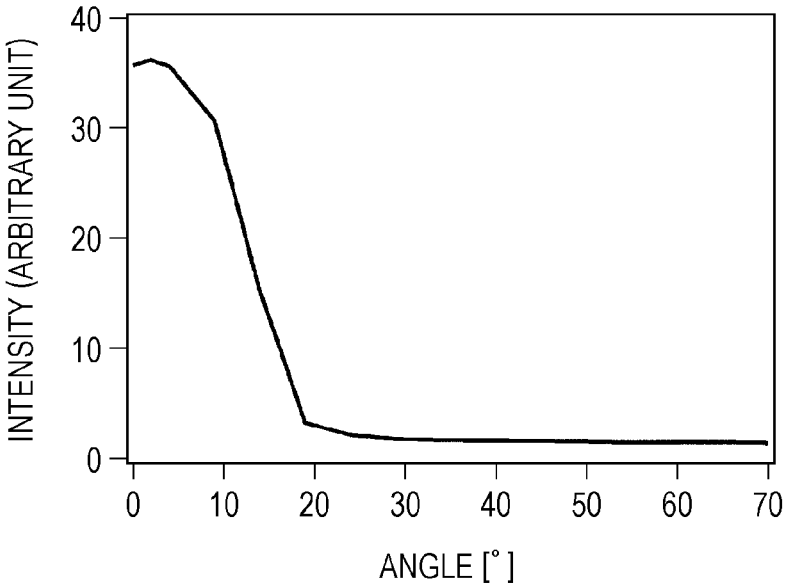
FIG. 29 is a graph showing the results of measurements of the angular dependence of light (wavelength: 610 nm) output from the sample light-emitting device.

FIG. 29 shows the angular dependence of the intensity of light of a wavelength of 610 nm for rotation about an axis perpendicular to the line direction, as illustrated in FIG. 28D. As shown in FIG. 29, the light was significantly enhanced in the front direction and was little enhanced at other angles. The directional angle of the light output in the front direction is less than 15 degrees. The directional angle is the angle at which the intensity is 50% of the maximum intensity and is expressed as the angle of one side with respect to the direction with the maximum intensity. The results shown in FIG. 29 demonstrates that directional light emission was achieved. In addition, all the light was the TM mode, which demonstrates that polarized light emission was simultaneously achieved.

Although YAG:Ce, which emits light in a wide wavelength range, was used in the above experiment, directional and polarized light emission can also be achieved using a similar structure including a photoluminescent material that emits light in a narrow wavelength range. Such a photoluminescent material does not emit light of other wavelengths and can therefore be used to provide a light source that does not emit light in other directions or in other polarized states.

10. Other Modifications

Other modifications of a light-emitting device and a light-emitting apparatus according to the present disclosure will be described below.

Figure 31:
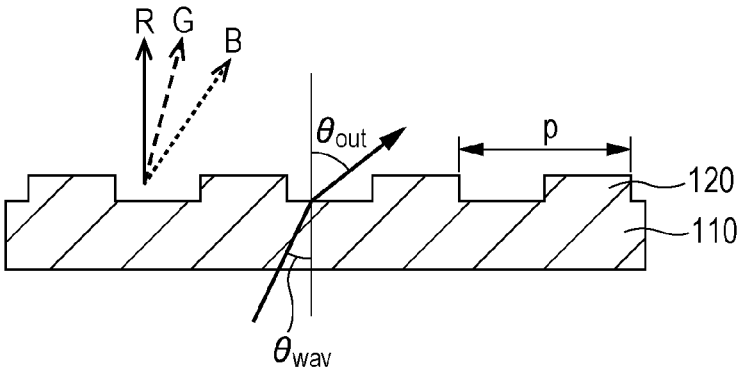
FIG. 31 is a schematic view illustrating the relationship between the wavelength and output direction of light under the light enhancement effect in a light-emitting device having a periodic structure on a photoluminescent layer.

As described above, the wavelength and output direction of light under the light enhancement effect depend on the submicron structure of a light-emitting device according to the present disclosure. FIG. 31 illustrates a light-emitting device having a periodic structure 120 on a photoluminescent layer 110. The periodic structure 120 is formed of the same material as the photoluminescent layer 110 and is the same as the one-dimensional periodic structure 120 illustrated in FIG. 1A. Light under the light enhancement effect of the one-dimensional periodic structure 120 satisfies $p \times n_{wav} \times \sin\theta_{wav} - p \times n_{out} \times \sin\theta_{out} = m\lambda$ (see equation (5)), where p (nm) is the period of the one-dimensional periodic structure 120, $n_{wav}$ is the refractive index of the photoluminescent layer 110, $n_{out}$ is the refractive index of an outer medium to which the light is output, $\theta_{wav}$ is the incident angle on the one-dimensional periodic structure 120, and $\theta_{out}$ is the angle at which the light is output from one-dimensional periodic structure 120 to the outer medium. $\lambda$ is the light wavelength in air, and m is an integer.

The equation can be transformed into $\theta_{out} = \arcsin[(n_{wav} \times \sin\theta_{wav} - m\lambda/p)/n_{out}]$. Thus, in general, the output angle $\theta_{out}$ of light under the light enhancement effect varies with the wavelength $\lambda$. Consequently, as schematically illustrated in FIG. 31, the color of visible light varies with the observation direction.

This visual angle dependency can be reduced by determining $n_{wav}$ and $n_{out}$ so as to make $(n_{wav} \times \sin\theta_{wav} - m\lambda/p)/n_{out}$ constant for any wavelength $\lambda$. The refractive indexes of substances have wavelength dispersion (i.e. wavelength dependence). Thus, a material to be selected should have the wavelength dispersion characteristics of $n_{wav}$ and $n_{out}$ such that $(n_{wax} \times \sin\theta_{wav} - m\lambda/p)/n_{out}$ is independent of the wavelength $\lambda$. For example, if the outer medium is air, $n_{out}$ is approximately 1.0 irrespective of the wavelength. Thus, it is desirable that the material of the photoluminescent layer 110 and the one-dimensional periodic structure 120 be a material having narrow wavelength dispersion of the refractive index $n_{wav}$. It is also desirable that the material have reciprocal dispersion, and the refractive index $n_{wav}$ decrease with decreasing wavelength of light.

Figure 32A:
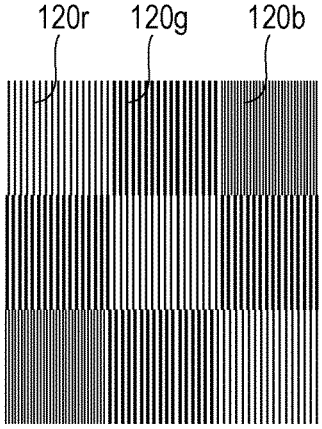
FIG. 32A is a schematic plan view of an example structure of an array of periodic structures having different wavelengths at which the light enhancement effect is produced.

As illustrated in FIG. 32A, an array of periodic structures having different wavelengths at which the light enhancement effect is produced can emit white light. In FIG. 32A, a periodic structure 120r that can enhance red light (R), a periodic structure 120g that can enhance green light (G), and a periodic structure 120b that can enhance blue light (B) are arranged in a matrix. Each of the periodic structures 120r, 120g, and 120b may be a one-dimensional periodic structure. The projections of the periodic structures 120r, 120g, and 120b are arranged in parallel. Thus, the red light, green light, and blue light have the same polarization characteristics. Light beams of three primary colors emitted from the periodic structures 120r, 120g, and 120b under the light enhancement effect are mixed to produce linearly polarized white light.

Each of the periodic structures 120r, 120g, and 120b arranged in a matrix is referred to as a unit periodic structure (or pixel). The size (e.g. the length of one side) of the unit periodic structure may be at least three times the period. It is desirable that the unit periodic structures be not perceived by the human eye in order to produce the color mixing effect. For example, it is desirable that the length of one side be less than 1 mm. Although each of the unit periodic structures is square in FIG. 32A, adjacent periodic structures 120r, 120g, and 120b may be in the shape other than square, such as rectangular, triangular, or hexagonal.

A photoluminescent layer under each of the periodic structures 120r, 120g, and 120b may be the same or may be formed of different photoluminescent materials corresponding to each color of light.

Figure 32B:
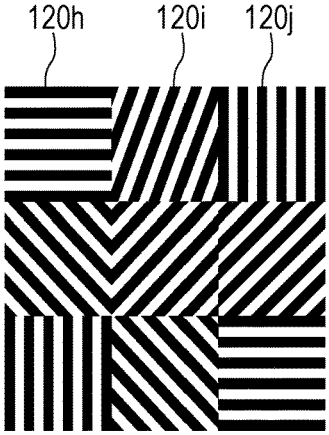
FIG. 32B is a schematic plan view of an example structure that includes an array of one-dimensional periodic structures having projections extending in different directions.

As illustrated in FIG. 32B, the projections of the one-dimensional periodic structures (including periodic structures 120h, 120i, and 120j) may extend in different directions. Light emitted from each of the periodic structures under the light enhancement effect may have the same wavelength or different wavelengths. For example, the same periodic structures arranged as illustrated in FIG. 32B can produce unpolarized light. The periodic structures 120r, 120g, and 120b in FIG. 32A arranged as illustrated in FIG. 32B can produce unpolarized white light as a whole.

Figure 32C:
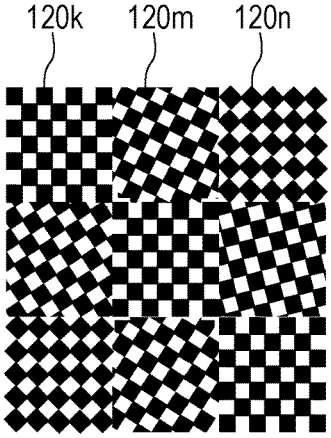
FIG. 32C is a schematic plan view of an example structure that includes an array of two-dimensional periodic structures.

As a matter of course, the periodic structures are not limited to one-dimensional periodic structures and may be an array of two-dimensional periodic structures (including periodic structures 120k, 120m, and 120n), as illustrated in FIG. 32C. The period and direction of each of the periodic structures 120k, 120m, and 120n may be the same or different, as described above, and may be appropriately determined as required.

Figure 33:
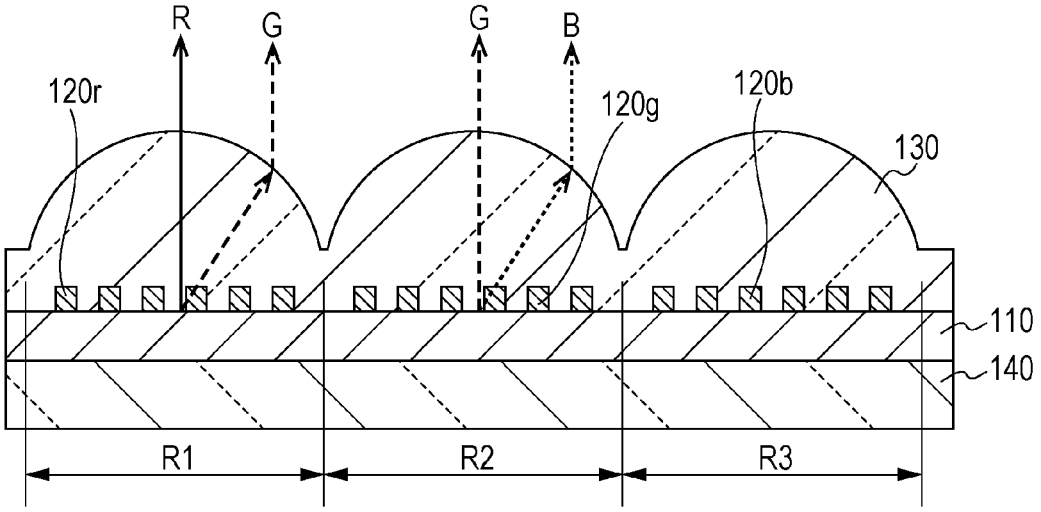
FIG. 33 is a schematic cross-sectional view of a light-emitting device including microlenses.

As illustrated in FIG. 33, for example, an array of microlenses 130 may be disposed on a light output side of a light-emitting device. The array of microlenses 130 can refract oblique light in the normal direction and produce the color mixing effect.

The light-emitting device illustrated in FIG. 33 includes regions R1, R2, and R3, which include the periodic structures 120r, 120g, and 120b, respectively, illustrated in FIG. 32A. In the region R1, the periodic structure 120r outputs red light R in the normal direction and, for example, outputs green light G in an oblique direction. The microlens 130 refracts the oblique green light G in the normal direction. Consequently, a mixture of the red light R and the green light G is observed in the normal direction. Thus, the microlenses 130 can reduce the difference in light wavelength depending on the angle. Although the microlens array including microlenses corresponding to the periodic structures is described here, another microlens array is also possible. As a matter of course, periodic structures to be tiled are not limited to those described above and may be the same periodic structures or the structures illustrated in FIG. 32B or 32C.

Lenticular lenses may also be used as optical elements for refracting oblique light instead of the microlens array. In addition to lenses, prisms may also be used. A prism array may also be used. A prism corresponding to each periodic structure may be arranged. Prisms of any shape may be used. For example, triangular prisms or pyramidal prisms may be used.

Figure 34A:
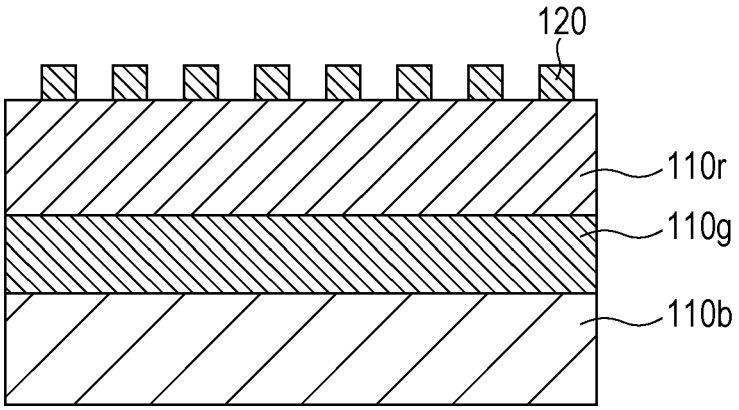
FIG. 34A is a schematic cross-sectional view of a light-emitting device that includes photoluminescent layers having different emission wavelengths.
Figure 34B:
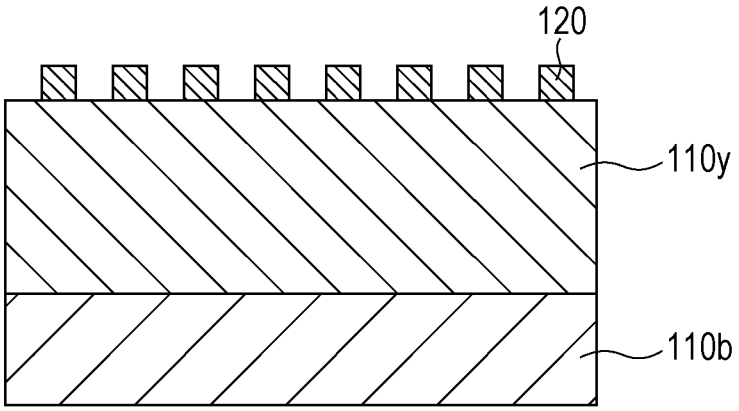
FIG. 34B is a schematic cross-sectional view of another light-emitting device that includes photoluminescent layers having different emission wavelengths.

White light (or light having a broad spectral width) may be produced by using the periodic structure described above or a photoluminescent layer as illustrated in FIG. 34A or 34B. As illustrated in FIG. 34A, photoluminescent layers 110b, 110g, and 110r having different emission wavelengths may be stacked to produce white light. The stacking sequence is not limited to that illustrated in FIG. 34A. As illustrated in FIG. 34B, a photoluminescent layer 110y that emits yellow light may be disposed on a photoluminescent layer 110b that emits blue light. The photoluminescent layer 110y may be formed of YAG.

When photoluminescent materials, such as fluorescent dyes, to be mixed with a matrix (i.e. host) material are used, photoluminescent materials having different emission wavelengths may be mixed with the matrix material to emit white light from a single photoluminescent layer. Such a photoluminescent layer that can emit white light may be used in tiled unit periodic structures as illustrated in FIGS. 32A to 32C.

When an inorganic material (e.g., YAG) is used as a material of the photoluminescent layer 110, the inorganic material may be subjected to heat treatment at more than 1000° C. in the production process. During the production process, impurities may diffuse from an underlayer (typically, a substrate) and affect the light-emitting properties of the photoluminescent layer 110. In order to prevent impurities from diffusing into the photoluminescent layer 110, a diffusion-barrier layer (i.e. barrier layer) 108 may be disposed under the photoluminescent layer 110, as illustrated in FIGS. 35A to 35D. As illustrated in FIGS. 35A to 35D, the diffusion-barrier layer 108 is disposed under the photoluminescent layer 110 in the structures described above.

Figure 35A:
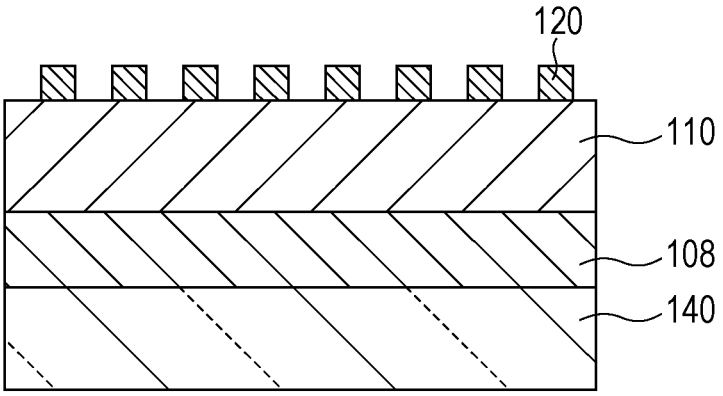
FIG. 35A is a schematic cross-sectional view of an example light-emitting device that includes a diffusion-barrier layer (i.e. barrier layer) under a photoluminescent layer.
Figure 35B:
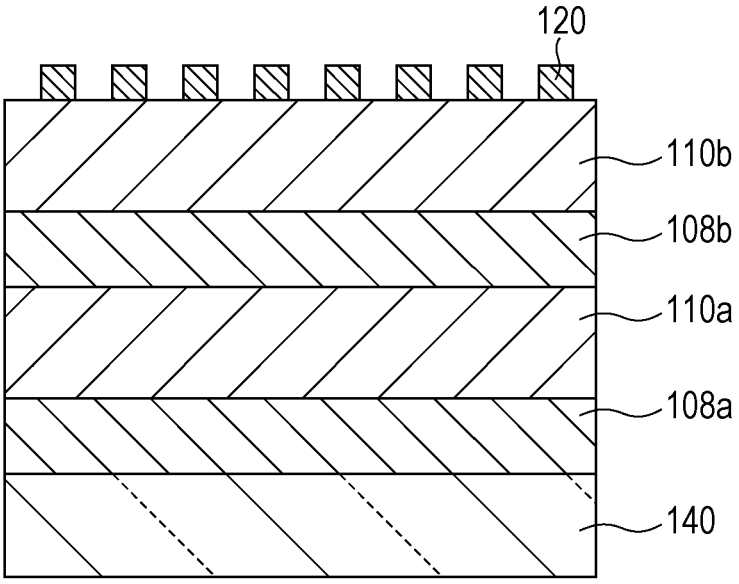
FIG. 35B is a schematic cross-sectional view of another example light-emitting device that includes a diffusion-barrier layer (i.e. barrier layer) under a photoluminescent layer.

For example, as illustrated in FIG. 35A, the diffusion-barrier layer 108 is disposed between a substrate 140 and the photoluminescent layer 110. As illustrated in FIG. 35B, when there are photoluminescent layers 110a and 110b, diffusion-barrier layers 108a and 108b are disposed under the photoluminescent layers 110a and 110b, respectively.

Figure 35C:
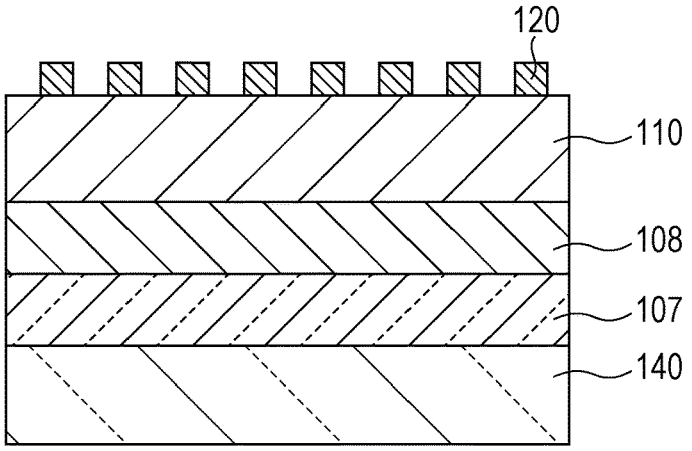
FIG. 35C is a schematic cross-sectional view of another example light-emitting device that includes a diffusion-barrier layer (i.e. barrier layer) under a photoluminescent layer.
Figure 35D:
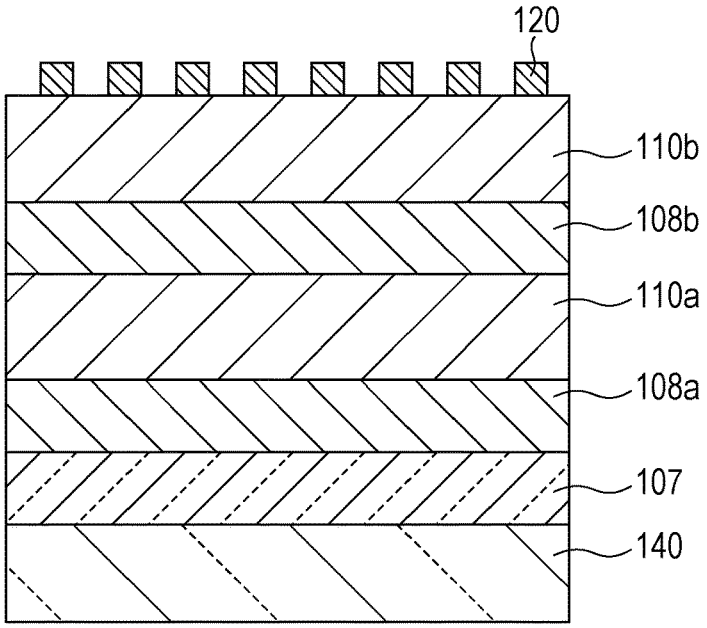
FIG. 35D is a schematic cross-sectional view of another example light-emitting device that includes a diffusion-barrier layer (i.e. barrier layer) under a photoluminescent layer.

When the substrate 140 has a higher refractive index than the photoluminescent layer 110, a low-refractive-index layer 107 may be formed on the substrate 140, as illustrated in FIGS. 35C and 35D. When the low-refractive-index layer 107 is disposed on the substrate 140, as illustrated in FIG. 35C, the diffusion-barrier layer 108 is formed between the low-refractive-index layer 107 and the photoluminescent layer 110. As illustrated in FIG. 35D, when there are photoluminescent layers 110a and 110b, diffusion-barrier layers 108a and 108b are disposed under the photoluminescent layers 110a and 110b, respectively.

The low-refractive-index layer 107 is formed if the substrate 140 has a refractive index greater than or equal to the refractive index of the photoluminescent layer 110. The low-refractive-index layer 107 has a lower refractive index than the photoluminescent layer 110. The low-refractive-index layer 107 may be formed of $MgF_2$, LiF, $CaF_2$, $BaF_2$, $SrF_2$, quartz, a resin, or room-temperature curing glass, such as hydrogen silsesquioxane (HSQ) spin-on glass (SOG). It is desirable that the thickness of the low-refractive-index layer 107 be greater than the light wavelength. For example, the substrate 140 may be formed of $MgF_2$, LiF, $CaF_2$, $BaF_2$, $SrF_2$, glass, a resin, MgO, $MgAl_2O_4$, sapphire ($Al_2O_3$), $SrTiO_3$, $LaAlO_3$, $TiO_2$, $Gd_3GasO_{12}$, $LaSrAlO_4$, $LaSrGaO_4$, $LaTaO_3$, SrO, YSZ ($ZrO_2.Y_2O_3$), YAG, or $Tb_3Ga_5O_{12}$.

It is desirable that the diffusion-barrier layers 108, 108a, and 108b be selected in a manner that depends on the type of element to be prevented from diffusion. For example, the diffusion-barrier layers 108, 108a, and 108b may be formed of strongly covalent oxide crystals or nitride crystals. The diffusion-barrier layers 108, 108a, and 108b may have a thickness of 50 nm or less.

In structures that include a layer adjacent to the photoluminescent layer 110, such as the diffusion-barrier layer 108 or a crystal growth layer 106 described later, if the adjacent layer has a higher refractive index than the photoluminescent layer 110, the refractive index $n_{wav}$ is the average refractive index of the layer having the higher refractive index and the photoluminescent layer 110 weighted by their respective volume fractions. This is optically equivalent to a photoluminescent layer composed of layers of different materials.

Figure 36A:
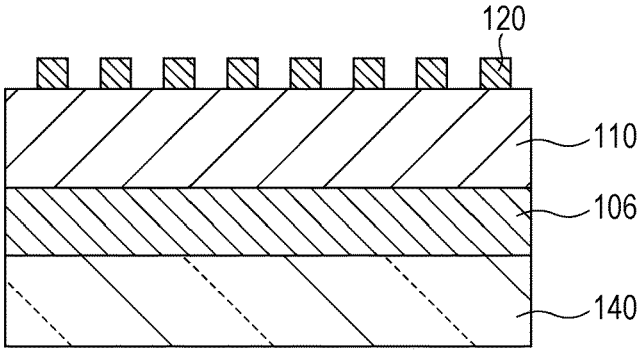
FIG. 36A is a schematic cross-sectional view of an example light-emitting device that includes a crystal growth layer (i.e. seed layer) under a photoluminescent layer.

When the photoluminescent layer 110 is formed of an inorganic material, the photoluminescent layer 110 may have poor light-emitting properties due to low crystallinity of the inorganic material. In order to increase the crystallinity of the inorganic material of the photoluminescent layer 110, a crystal growth layer (hereinafter also referred to as a "seed layer") 106 may be formed under the photoluminescent layer 110, as illustrated in FIG. 36A. The material of the crystal growth layer 106 is lattice-matched to the crystals of the overlying photoluminescent layer 110. It is desirable that the lattice matching be within ±5%. If the substrate 140 has a higher refractive index than the photoluminescent layer 110, it is desirable that the crystal growth layer 106 or 106a have a lower refractive index than the photoluminescent layer 110.

Figure 36B:
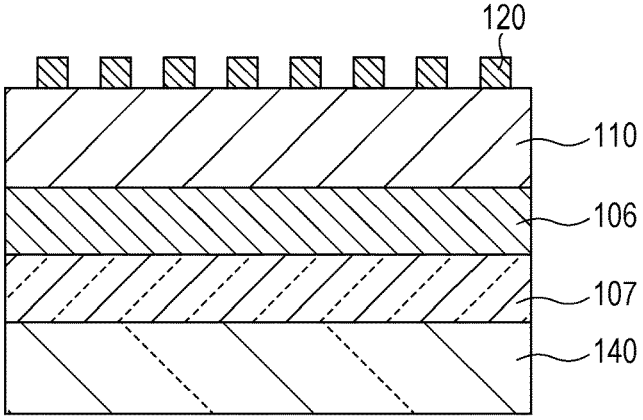
FIG. 36B is a schematic cross-sectional view of another example light-emitting device that includes a crystal growth layer (i.e. seed layer) under a photoluminescent layer.
Figure 36C:
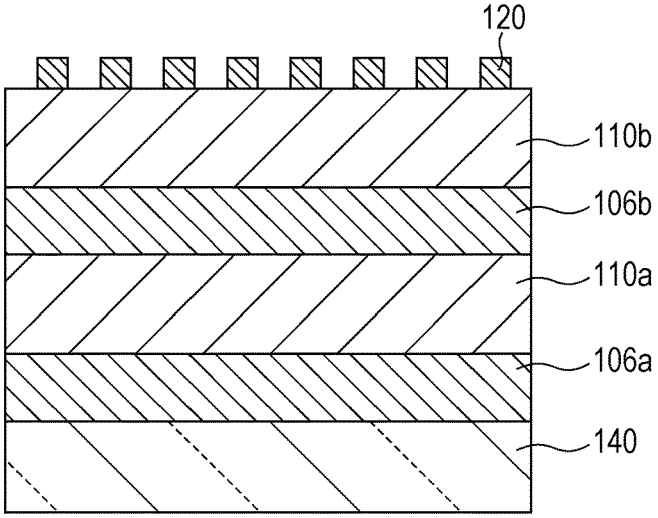
FIG. 36C is a schematic cross-sectional view of another example light-emitting device that includes a crystal growth layer (i.e. seed layer) under a photoluminescent layer.

If the substrate 140 has a higher refractive index than the photoluminescent layer 110, a low-refractive-index layer 107 may be formed on the substrate 140, as illustrated in FIG. 36B. In this case, because the crystal growth layer 106 is in contact with the photoluminescent layer 110, the crystal growth layer 106 is formed on the low-refractive-index layer 107, which is disposed on the substrate 140. In structures that include photoluminescent layers 110a and 110b, as illustrated in FIG. 36C, it is desirable that crystal growth layers 106a and 106b be formed on the photoluminescent layer 110a and 110b, respectively. Each of the crystal growth layers 106, 106a, and 106b may have a thickness of 50 nm or less.

Figure 37A:
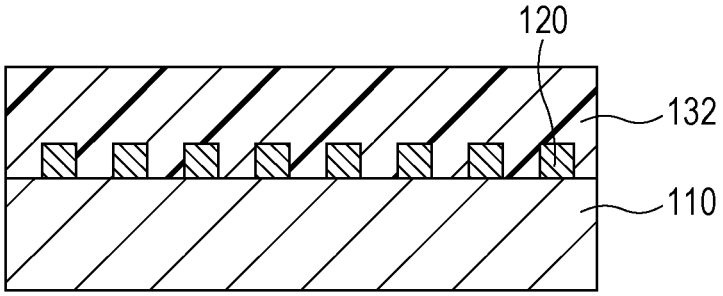
FIG. 37A is a schematic cross-sectional view of an example light-emitting device that includes a surface protective layer for protecting a periodic structure.
Figure 37B:
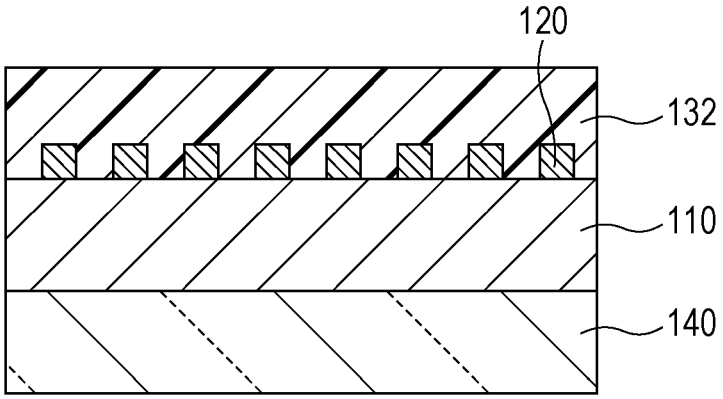
FIG. 37B is a schematic cross-sectional view of another example light-emitting device that includes a surface protective layer for protecting a periodic structure.

As illustrated in FIGS. 37A and 37B, a surface protective layer 132 may be formed to protect the periodic structure 120.

The surface protective layer 132 may be formed in a light-emitting device with or without the substrate 140, as illustrated in FIGS. 37A and 37B. In the light-emitting device without the substrate as illustrated in FIG. 37A, a surface protective layer may be formed under the photoluminescent layer 110. The surface protective layer 132 may be formed on any surface of the light-emitting devices. The periodic structure 120 is not limited to those illustrated in FIGS. 37A and 37B and may be of any of the types described above.

The surface protective layer 132 may be formed of a resin, a hard coat material, $SiO_2$, alumina ($Al_2O_3$), silicon oxycarbide (SiOC), or diamond-like carbon (DLC). The surface protective layer 132 may have a thickness in the range of 100 nm to 10 μm.

The surface protective layer 132 can protect the light-emitting device from the external environment and suppress the degradation of the light-emitting device. The surface protective layer 132 can protect the surface of the light-emitting device from scratches, water, oxygen, acids, alkalis, or heat. The material and thickness of the surface protective layer 132 may be appropriately determined for each use.

Photoluminescent materials sometimes deteriorate due to heat. Heat is mostly generated by the nonradiative loss or Stokes loss of the photoluminescent layer 110. For example, the thermal conductivity of quartz (1.6 W/m·K) is lower by an order of magnitude than the thermal conductivity of YAG (11.4 W/m·K). Thus, heat generated by the photoluminescent layer (e.g., a YAG layer) 110 is not fully dissipated via the substrate (e.g., a quartz substrate) 140 and increases the temperature of the photoluminescent layer 110, thereby possibly causing thermal degradation.

Figure 38A:
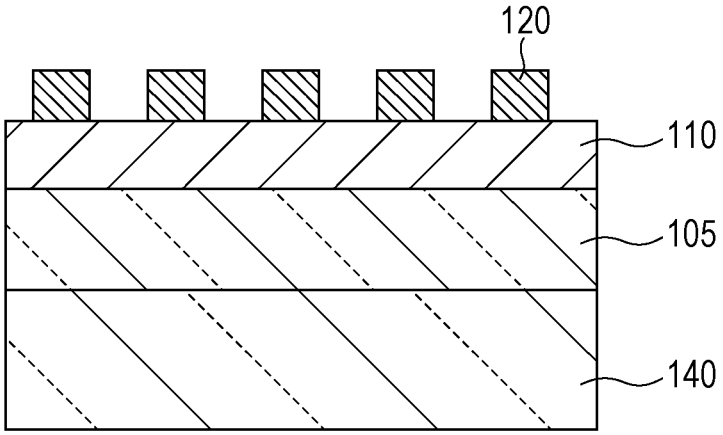
FIG. 38A is a schematic cross-sectional view of an example light-emitting device having a transparent thermally conductive layer.
Figure 38B:
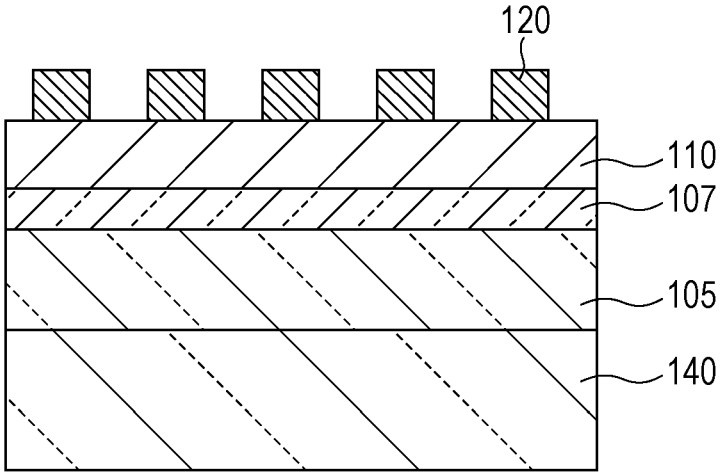
FIG. 38B is a schematic cross-sectional view of another example light-emitting device having a transparent thermally conductive layer.

As illustrated in FIG. 38A, a transparent thermally conductive layer 105 between the photoluminescent layer 110 and the substrate 140 can efficiently dissipate heat of the photoluminescent layer 110 and prevent temperature rise. It is desirable that the transparent thermally conductive layer 105 have a lower refractive index than the photoluminescent layer 110. If the substrate 140 has a lower refractive index than the photoluminescent layer 110, the transparent thermally conductive layer 105 may have a higher refractive index than the photoluminescent layer 110. In such a case, the transparent thermally conductive layer 105, together with the photoluminescent layer 110, forms a waveguide layer, and therefore desirably has a thickness of 50 nm or less. As illustrated in FIG. 38B, in the presence of a low-refractive-index layer 107 between the photoluminescent layer 110 and the transparent thermally conductive layer 105, a thick transparent thermally conductive layer 105 may be used.

Figure 38C:
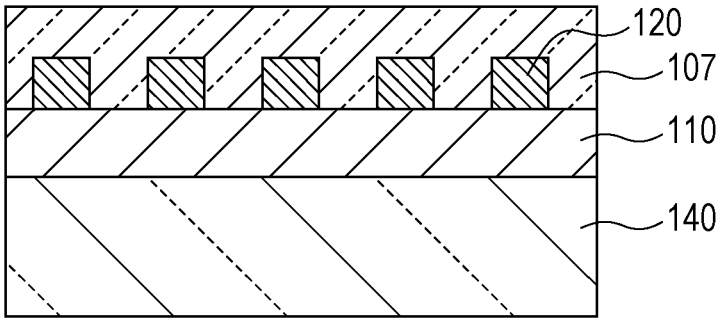
FIG. 38C is a schematic cross-sectional view of another example light-emitting device having a transparent thermally conductive layer.
Figure 38D:
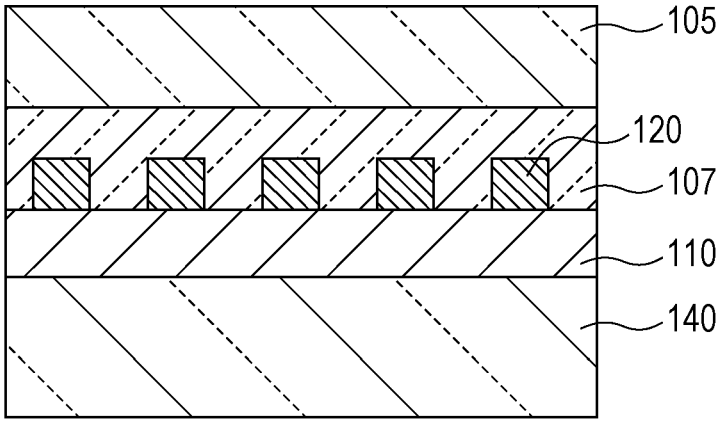
FIG. 38D is a schematic cross-sectional view of another example light-emitting device having a transparent thermally conductive layer.

As illustrated in FIG. 38C, the periodic structure 120 may be covered with a low-refractive-index layer 107 having high thermal conductivity. As illustrated in FIG. 38D, a transparent thermally conductive layer 105 may be formed on the low-refractive-index layer 107 covering the periodic structure 120. The low-refractive-index layer 107 does not necessarily have high thermal conductivity.

The material of the transparent thermally conductive layer 105 may be $Al_2O_3$, MgO, $Si_3N_4$, ZnO, AlN, $Y_2O_3$, diamond, graphene, $CaF_2$, or $BaF_2$. Among these, $CaF_2$ and $BaF_2$ can be used for the low-refractive-index layer 107 due to their low refractive indexes.

A light-emitting apparatus that includes a light-emitting device 100 and a light source 180 and has high heat dissipation characteristics will be described below with reference to FIGS. 39A to 39D.

Figure 39A:
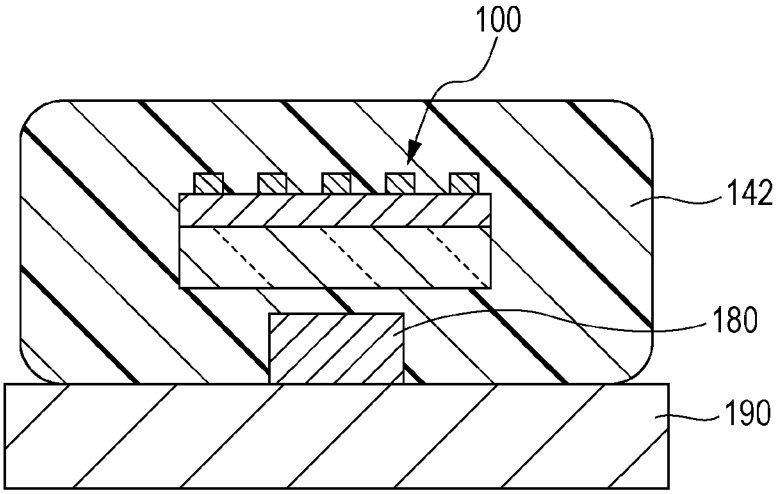
FIG. 39A is a schematic cross-sectional view of an example light-emitting apparatus having improved heat dissipation characteristics.

A light-emitting apparatus illustrated in FIG. 39A includes an LED chip 180 as a light source 180 and a light-emitting device 100. The light-emitting device 100 may be of any of the types described above. The LED chip 180 is disposed on a supporting substrate 190. The light-emitting device 100 is separated from the LED chip 180 by a predetermined distance. The light-emitting device 100 emits light in response to excitation light emitted from the LED chip 180. The LED chip 180 and the light-emitting device 100 on the supporting substrate 190 are covered with a sealing component 142.

The sealing component 142 has high thermal conductivity and is transparent to light. The material of the sealing component 142 (hereinafter also referred to as a "sealing material") may be a composite material containing a thermally conductive filler and a resin material. The thermally conductive filler may be $Al_2O_3$, ZnO, $Y_2O_3$, graphene, or AlN. The resin material may be an epoxy resin or a silicone resin. In particular, the sealing material may be a nanocomposite material containing a thermally conductive filler of a nanometer size (i.e., a submicron size). Use of the nanocomposite material can suppress the diffuse reflection (or scattering) of light. The nanocomposite material may contain ZnO or $Al_2O_3$ as filler and an epoxy resin or a silicone resin.

If the light-emitting device 100 is of a type in which the periodic structure is exposed at the surface, as illustrated in FIG. 39A, it is desirable that the refractive index of a medium around the periodic structure be lower than the refractive index of the periodic structure. If the periodic structure is formed of a light-transmissive layer, it is desirable that the sealing component 142 have a lower refractive index than the light-transmissive layer. If the periodic structure is formed of the same material as a photoluminescent layer, it is desirable that the sealing component 142 have a lower refractive index than the photoluminescent layer.

Figure 39B:
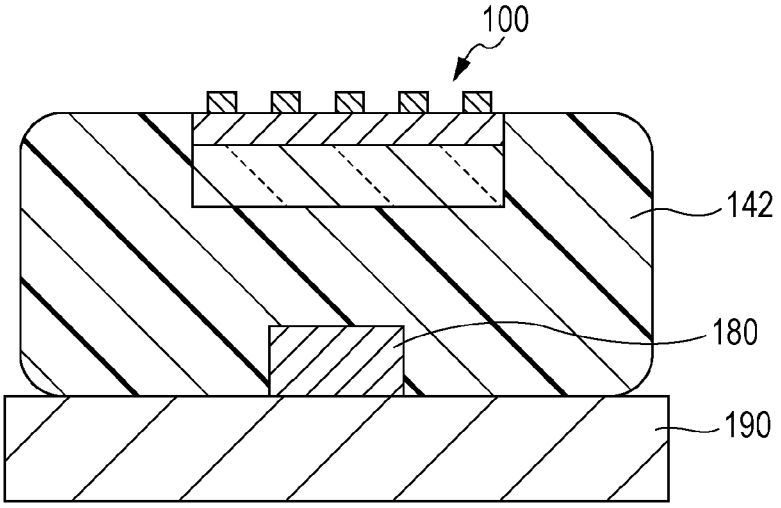
FIG. 39B is a schematic cross-sectional view of another example light-emitting apparatus having improved heat dissipation characteristics.

As illustrated in FIG. 39B, the sealing component 142 may be formed such that the vicinity of the surface (e.g., a light-transmissive layer having a periodic structure or a photoluminescent layer) of the light-emitting device 100 is exposed. In this case, the sealing component 142 may have any refractive index.

Figure 39C:
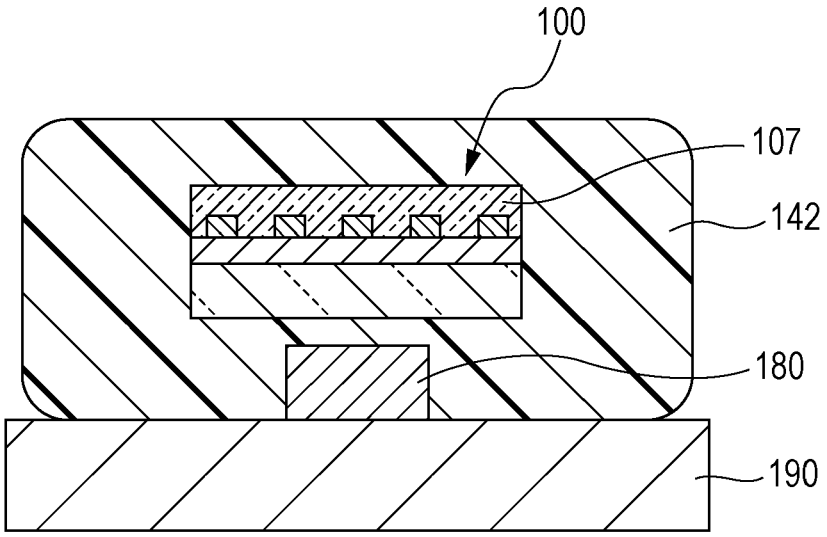
FIG. 39C is a schematic cross-sectional view of another example light-emitting apparatus having improved heat dissipation characteristics.

If the light-emitting device 100 is of a type in which the periodic structure is covered with a low-refractive-index layer 107 (see FIG. 38C), as illustrated in FIG. 39C, the sealing component 142 may have a higher refractive index than the periodic structure. Such a structure can offer a wide selection of the material of the sealing component 142.

Figure 39D:
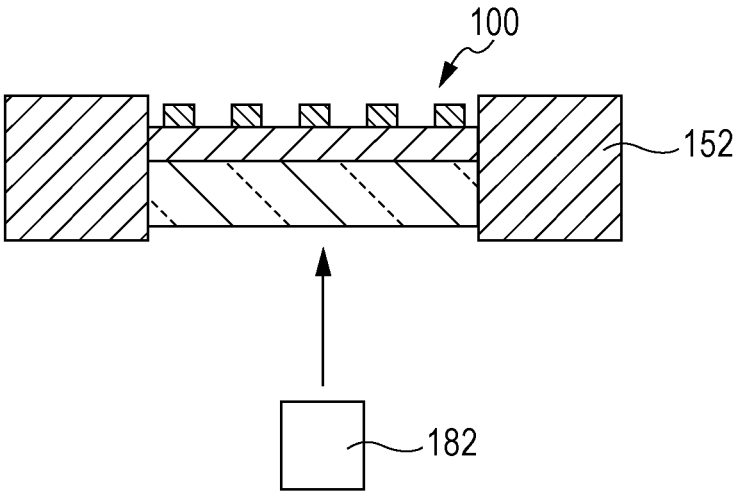
FIG. 39D is a schematic cross-sectional view of another example light-emitting apparatus having improved heat dissipation characteristics.

As illustrated in FIG. 39D, the periphery of the light-emitting device 100 may be fixed to a thermally conductive holder 152. The holder 152 may be made of a metal. For example, this structure is desired if the sealing material cannot be placed between the light-emitting device 100 and a light source as in the case where a laser diode 182 is used as a light source. For example, the light-emitting devices 100 as illustrated in FIGS. 38A to 38D, which include the transparent thermally conductive layer 105 or the thermally conductive low-refractive-index layer 107 and therefore have high in-plane thermal conductivity, can effectively dissipate heat via the holder 152.

As illustrated in FIGS. 40A to 40D, a thermally conductive member 144 or 146 may be disposed on a surface of the light-emitting device 100. The thermally conductive member 144 or 146 may be made of a metal.

Figure 40A:
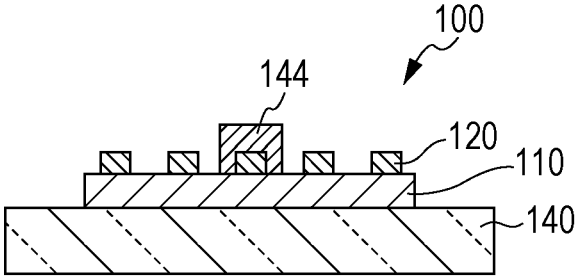
FIG. 40A is a schematic cross-sectional view of an example light-emitting device including a thermally conductive member.
Figure 40B:
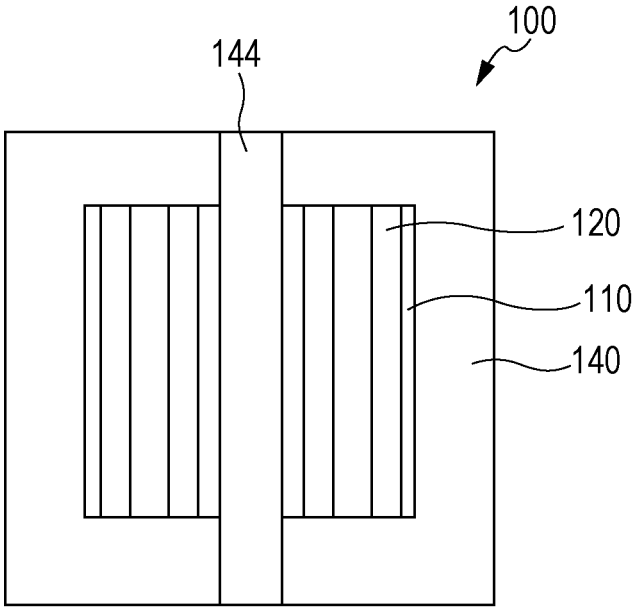
FIG. 40B is a plan view of the light-emitting device illustrated in FIG. 40A.

For example, as illustrated in a cross-sectional view of FIG. 40A and a plan view of FIG. 40B, the thermally conductive member 144 may partly cover a periodic structure 120 of a light-emitting device 100. Although the thermally conductive member 144 covers only one linear projection of a one-dimensional periodic structure in FIGS. 40A and 40B, the present disclosure is not limited to this.

Figure 40C:
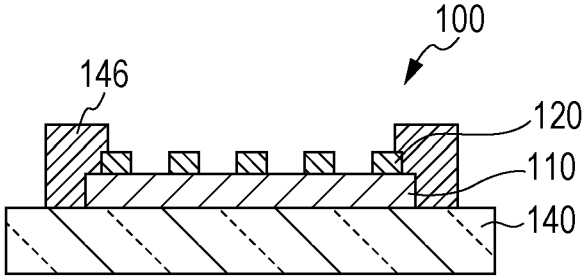
FIG. 40C is a schematic cross-sectional view of another example light-emitting device including a thermally conductive member.
Figure 40D:
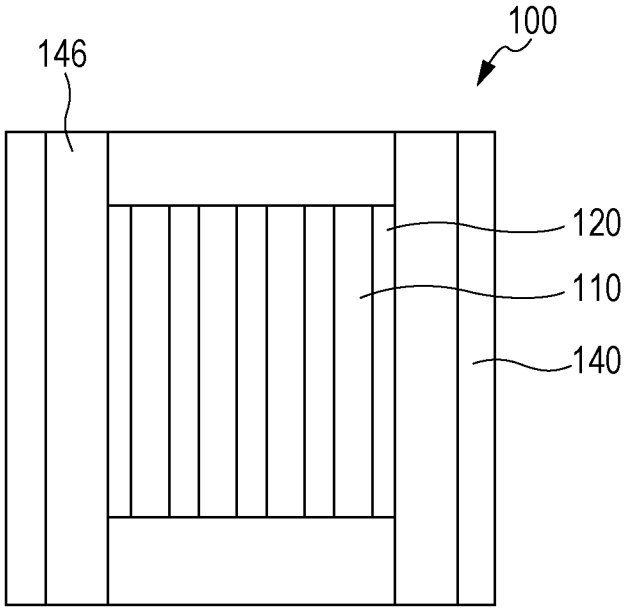
FIG. 40D is a plan view of the light-emitting device illustrated in FIG. 40C.
Figure 41A:
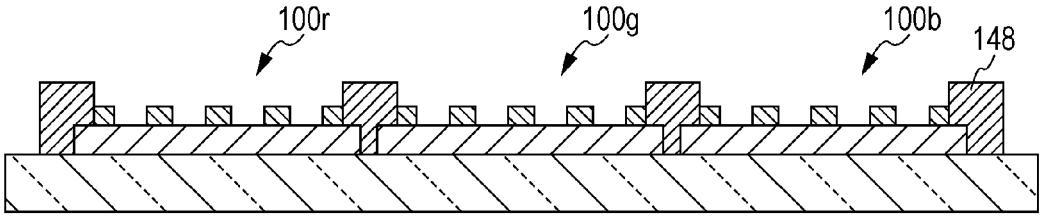
FIG. 41A is a schematic view of an example arrangement of thermally conductive members in tiled light-emitting devices.
Figure 41B:
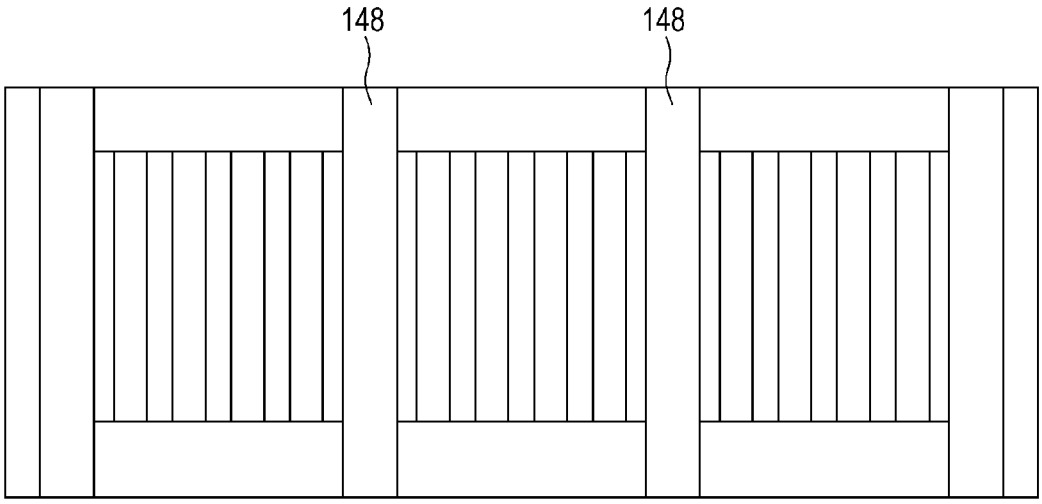
FIG. 41B is a plan view of the light-emitting device illustrated in FIG. 41A.

As illustrated in a cross-sectional view of FIG. 40C and a plan view of FIG. 40D, the thermally conductive member 146 may cover projections at each end of the periodic structure 120 of the light-emitting device 100 and cover end surfaces of a photoluminescent layer 110. In both cases, an increase in the area of the periodic structure and the photoluminescent layer covered with the thermally conductive member 146 may affect the characteristics of the light-emitting device 100. Thus, the area of the thermally conductive member 146 on a surface of the light-emitting device 100 should be minimized As illustrated in a cross-sectional view of FIG. 41A and a plan view of FIG. 41B, in tiled light-emitting devices 100r, 100g, and 100b having different structures, a thermally conductive member 148 may be disposed between adjacent light-emitting devices so as to cover end portions of the light-emitting devices. For example, as illustrated in these figures, in an array of a light-emitting device 100r that enhances red light, 100g that enhances green light, and 100b that enhances blue light, a thermally conductive member 148 made of a metal between adjacent light-emitting devices can prevent color mixing due to the light-shielding effect of the thermally conductive member 148. Thus, the thermally conductive member 148 may be used as a black matrix in display panels.

Figure 42A:
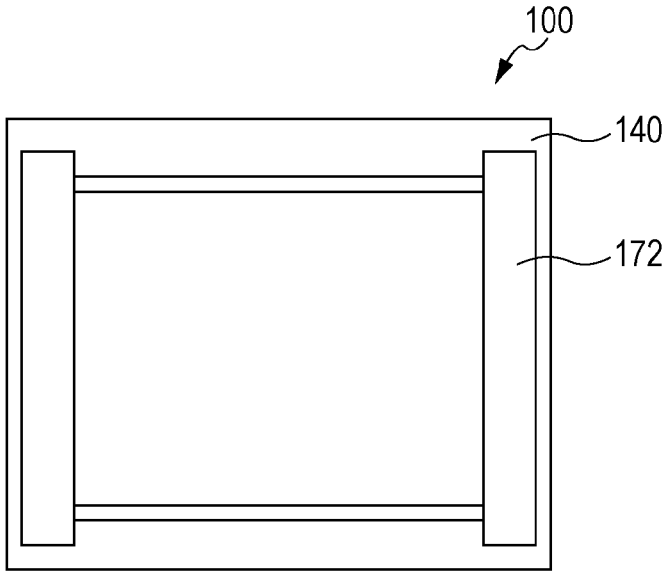
FIG. 42A is a schematic view of an example light-emitting apparatus including an interlock circuit.
Figure 42B:
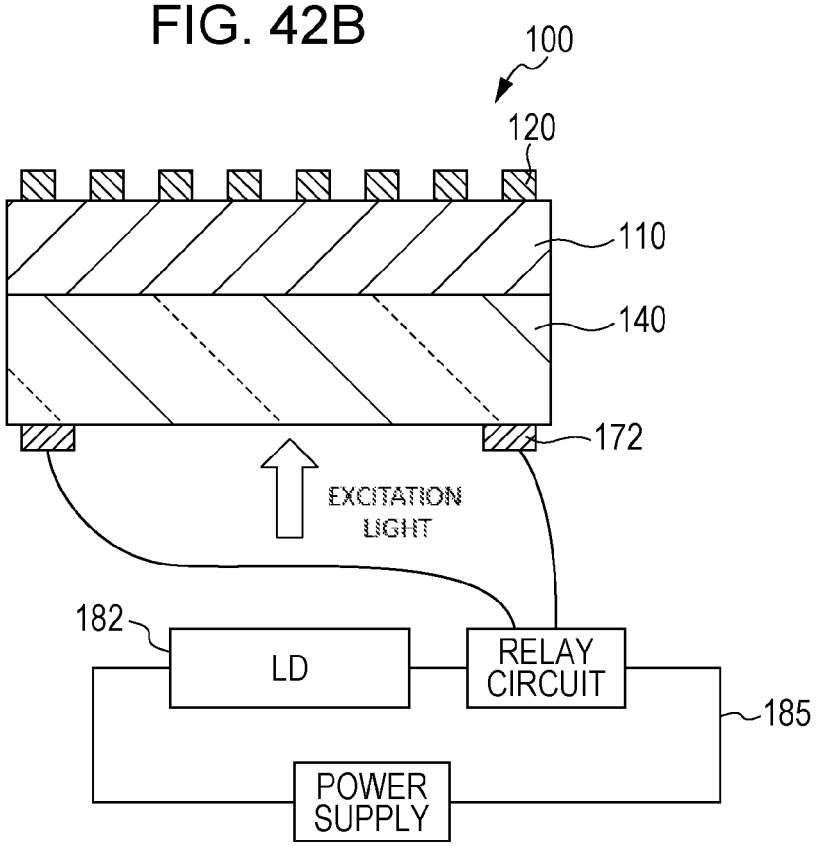
FIG. 42B is a schematic view of the configuration of a light-emitting apparatus including an interlock circuit.

FIGS. 42A and 42B illustrate a light-emitting apparatus including an interlock circuit 185. FIG. 42A is a schematic view of the back side of the light-emitting device 100. FIG. 42B is a schematic view of the light-emitting apparatus, including a cross-sectional view of the light-emitting device 100. As illustrated in FIGS. 42A and 42B, a closed electric wire 172 is disposed on the back side of a substrate 140 of a light-emitting device 100. The closed electric wire 172 is disposed along the periphery of the back side of the light-emitting device 100 and is configured to break when the substrate 140 is broken. The closed electric wire 172 may be made of a metallic material. Two terminals of the dosed electric wire 172 are electrically connected to a relay circuit of the interlock circuit 185. When the closed electric wire 172 is broken, the relay circuit will stop supplying an electric power to a light source 182. In particular, in the case that the light source 182 emits high-intensity light as in laser diodes, it is desirable to provide the interlock circuit 185 from a safety standpoint.

The submicron structures of the light-emitting devices according to these embodiments may be periodic structures and may be formed by photolithography or nanoprinting. Other methods for forming a submicron structure will be described below with reference to FIGS. 43A to 43F.

Figure 43A:
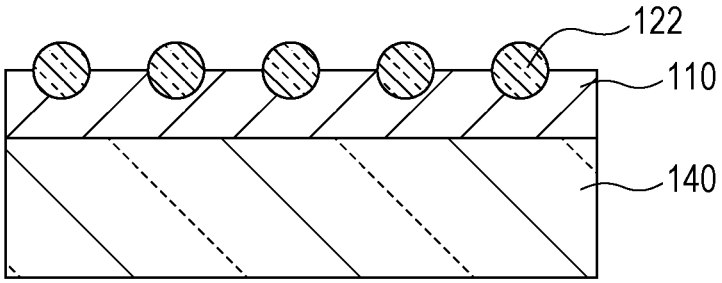
FIG. 43A is a first figure illustrating a method for forming a submicron structure using beads.

As illustrated in FIG. 43A, beads 122 are disposed on a surface of a photoluminescent layer 110 supported by a substrate 140. Each of the beads 122 can be partly embedded in the photoluminescent layer 110 and can be fixed to the photoluminescent layer 110. The refractive index of the beads 122 partly embedded in the photoluminescent layer 110 at regular intervals and partly protruding from the photoluminescent layer 110 may be equal to or lower than the refractive index of the photoluminescent layer 110. For example, if the beads 122 have a lower refractive index than the photoluminescent layer 110, a layer composed of the beads 122 (both the portions protruding from the photoluminescent layer 110 and the portions embedded in the photoluminescent layer 110) functions as a light-transmissive layer 120 having a submicron structure. If the beads 122 have substantially the same refractive index as the photoluminescent layer 110, the beads 122 and the photoluminescent layer 110 function as substantially one body, and the portions protruding from the photoluminescent layer 110 function as a light-transmissive layer 120 having a submicron structure.

Figure 43B:
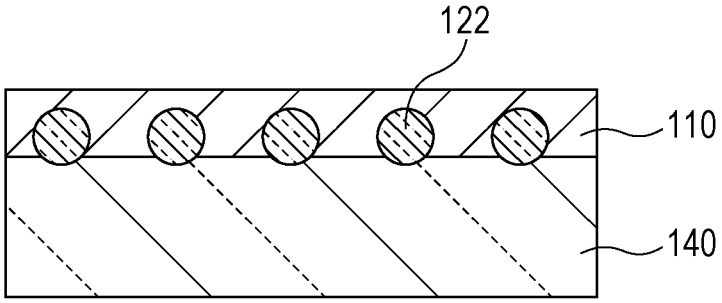
FIG. 43B is a second figure illustrating a method for forming a submicron structure using beads.

Alternatively, as illustrated in FIG. 43B, beads 122 may be disposed on a substrate 140 and may be covered with a photoluminescent layer 110. It is desirable that the beads 122 have a lower refractive index than the photoluminescent layer 110.

The beads 122 may have a diameter smaller than or equal to the $D_{int}$. If the beads 122 are densely packed, the beads 122 have substantially the same diameter as the Dim. If the beads 122 have a gap therebetween, the sum of the diameter of the beads 122 and the length of the gap corresponds to the $D_{int}$.

The beads 122 may be hollow beads or solid beads.

FIGS. 43C to 43F illustrate a schematic view of packing of beads and a light scattering pattern of the packed beads. In FIGS. 43C to 43F, black portions indicate solid portions in solid or hollow beads, and white portions indicate hollow beads or void portions in hollow beads.

Figure 43C:
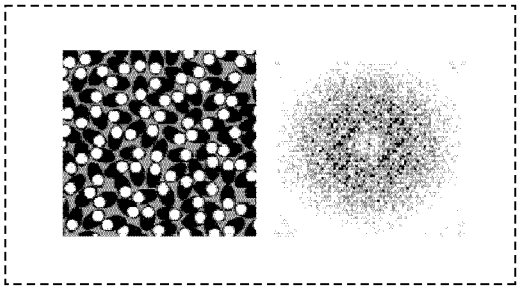
FIG. 43C illustrates a schematic view of an example of packing of beads and a light scattering pattern of the packed beads.
Figure 43D:
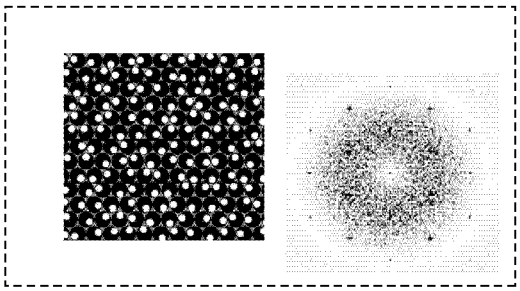
FIG. 43D illustrates a schematic view of another example of packing of beads and a light scattering pattern of the packed beads.
Figure 43E:
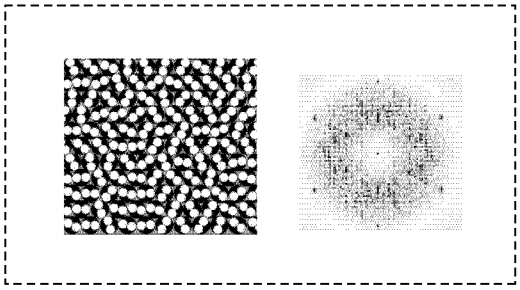
FIG. 43E illustrates a schematic view of another example of packing of beads and a light scattering pattern of the packed beads.
Figure 43F:
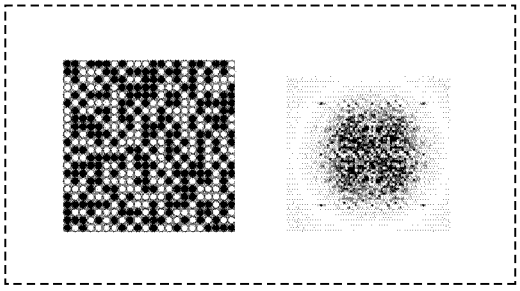
FIG. 43F illustrates a schematic view of another example of packing of beads and a light scattering pattern of the packed beads.

FIG. 43C illustrates densely packed hollow beads having an egg-shaped external shape and a light scattering patter of the hollow beads. The void portions of the hollow beads are generally spherical and are located at the bottom of the eggs. FIG. 43D illustrates densely packed hollow beads having a generally spherical external shape and a light scattering pattern of the hollow beads. The void portions of the hollow beads are generally spherical and are in contact with each external sphere. FIG. 43E illustrates densely packed hollow beads having a generally spherical external shape and a light scattering patter of the hollow beads. Each void portion of the hollow beads includes two generally spherical voids, and the two spherical voids are arranged along the diameter of the external sphere. FIG. 43F illustrates dense packing of hollow beads each having a generally spherical external shape and solid beads each having a generally spherical external shape, and a light scattering pattern of the packed beads. The hollow beads and solid beads have substantially the same diameter and are mixed at a volume ratio of approximately 50:50. The hollow beads and solid beads are almost randomly arranged without regularity.

Hollow beads and solid beads made of various glasses and resins are commercially available. For example, these beads may be an alumina powder widely commercially available as an abrasive or hollow silica manufactured by Nittetsu Mining Co., Ltd. These beads and a dispersant may be dispersed in a solvent (e.g., water or an alcohol), and the dispersion liquid may be applied to a substrate 140 or a photoluminescent layer 110 and dried to form a layer of densely packed beads.

11. Application Examples

As described above, light-emitting devices and light-emitting apparatuses including the light-emitting devices according to the present disclosure have various advantages and can be used with advantageous effects in various optical devices. Some application examples of light-emitting devices and light-emitting apparatuses including the light-emitting devices according to the present disclosure will be described below.

11-1. Fiber Lighting Apparatus

Figure 44:
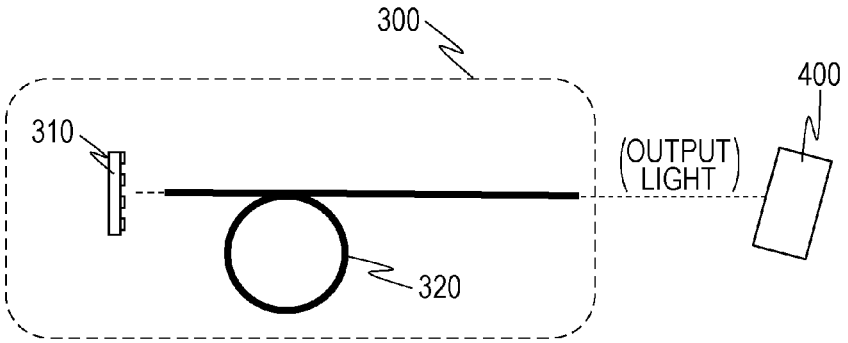
FIG. 44 is a schematic view of a fiber lighting apparatus to which a light-emitting device according to the present disclosure is applied.

FIG. 44 is a schematic view of a fiber lighting apparatus 300 to which a light-emitting device 310 according to the present disclosure is applied. The fiber lighting apparatus (i.e. light-emitting apparatus) 300 includes the light-emitting device 310 and an optical fiber 320, which can absorb light from the light-emitting device 310 at one end thereof and emit the light from the other end thereof. The optical fiber 320 transmits light from the light-emitting device 310 and irradiates an object 400 with the light. The light-emitting device 310 has any of the structures described above. The object 400 is a test object and is also referred to as a specimen.

When the object 400 is irradiated with white light, the light-emitting device 310 may have one of the structures described above with reference to FIGS. 32A to 32C and FIG. 33. When the object 400 is irradiated with light in a particular wavelength band, the light-emitting device 310 is configured to emit intense light in the wavelength band in a particular direction (e.g., in the front direction).

A light-emitting device according to the present disclosure can enhance light having a particular wavelength alone. Thus, a light source that emits light having a required wavelength alone can be easily provided. The wavelength of output light can be adjusted only by changing the periodic structure without changing the material of the photoluminescent layer. The wavelength of output light can be changed with the angle relative to the periodic structure. Such wavelength selectivity can be utilized in a narrow-band imaging (NBI, registered trademark) technique, for example. In narrow-band imaging, a mucosa is irradiated with blue and green light having a narrow-band wavelength to observe capillary vessels and fine patterns on the surface layer of the mucosa. For example, narrow-band imaging allows a lesion site to be easily observed with an endoscope described later.

The light-emitting device 310 utilized in narrow-band imaging includes two emission regions from which light in a blue wavelength band and light in a green wavelength band are emitted in a direction perpendicular to the photoluminescent layer (hereinafter also referred to as a "normal direction" or "perpendicular direction"). These emission regions are arranged in a direction perpendicular to or parallel to the photoluminescent layer. If blue light is used as excitation light, and part of the blue light is transmitted through the light-emitting device 310, the light-emitting device 310 may include only an emission region from which light in a green wavelength band is output in the perpendicular direction. In the present specification, the blue wavelength band ranges from 400 to 480 nm. The green wavelength band ranges from 490 to 580 nm. Typically, blue light having a wavelength in the range of 430 to 470 nm and green light having a wavelength in the range of 500 to 570 nm are used.

In known optical fiber lighting apparatuses, light sources, such as excimer lamps, metal halide lamps, and halogen lamps, have been used. The light-emitting apparatus 300 according to the present embodiment has the following advantages over known optical fiber lighting apparatuses due to high directionality of light emitted from the light-emitting device 310. (1) All or part of the components, such as a fiber coupler or lens, can be omitted. (2) The size of the light-emitting apparatus 300 can be reduced because a semiconductor light-emitting device can be used as an excitation light source. (3) High efficiency can be achieved due to a low optical loss (e.g., approximately one-tenth of the optical loss of excimer lamps). (4) The maintenance of the light-emitting apparatus 300 is easy because no lamp replacement is required.

Figure 45:
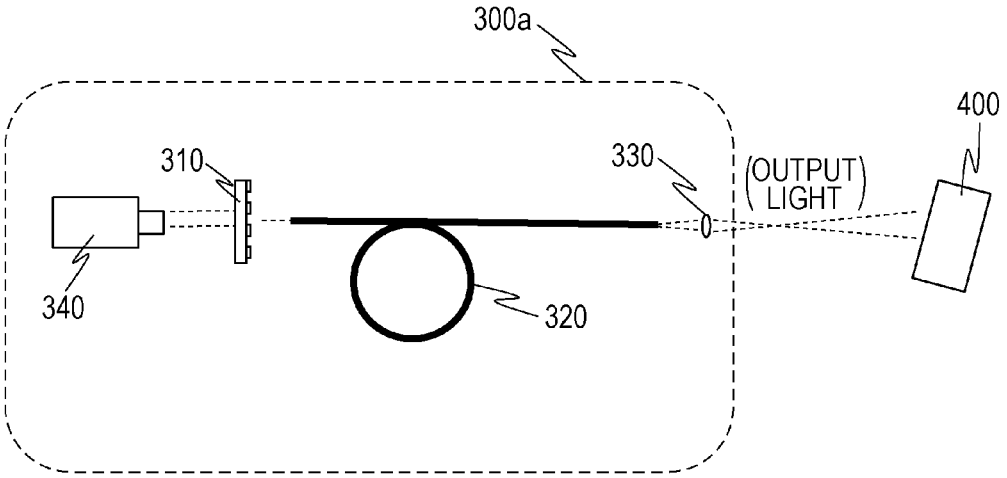
FIG. 45 is a schematic view of a modification of the light-emitting apparatus.

FIG. 45 is a schematic view of a modification of the light-emitting apparatus. A light-emitting apparatus 300a according to this embodiment includes an excitation light source 340 and an optical system 330. For example, the excitation light source 340 emits light in a blue wavelength band as excitation light. Excitation light from the excitation light source 340 is perpendicularly incident on the photoluminescent layer of the light-emitting device 310. The optical system 330 includes at least one lens for converging light output from the optical fiber 320. The lenses of the optical system 330 are appropriately designed in accordance with the intended use. As in this embodiment, the light-emitting apparatus 300a may include the optical system 330 and the excitation light source 340. Alternatively, the light-emitting apparatus 300a may include only one of these.

Figure 46:
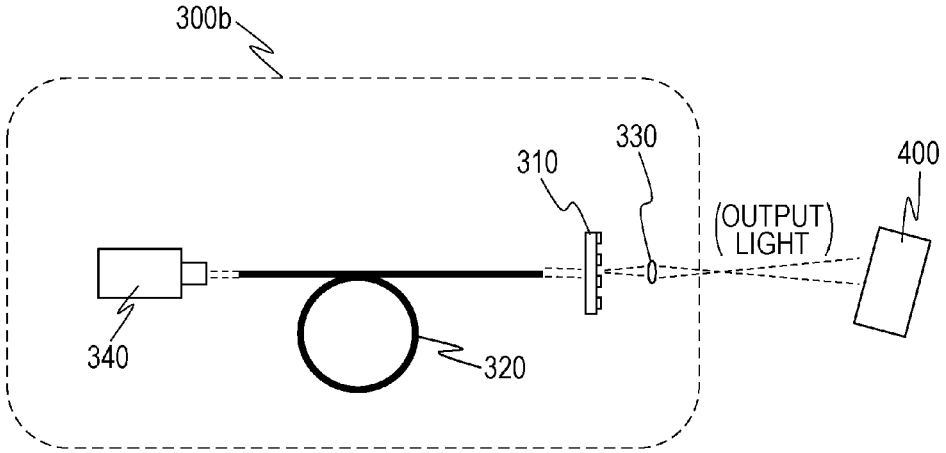
FIG. 46 is a schematic view of another modification of the light-emitting apparatus.

FIG. 46 is a schematic view of another modification of the light-emitting apparatus. A light-emitting apparatus 300b is different from the embodiments described above in that the optical fiber 320 transmits excitation light from the excitation light source 340 to the light-emitting device 310. The optical fiber 320 absorbs excitation light at one end thereof and outputs the excitation light from the other end thereof toward the light-emitting device 310. Although excitation light enters the back side of the photoluminescent layer of the light-emitting device 310 (i.e., a side opposite the surface structure) in the embodiment illustrated in FIG. 46, excitation light may enter the front or a side surface. In such an embodiment, the light-emitting device 310 may be disposed at an end of the optical fiber 320. Also in this embodiment, the optical system 330 may be omitted.

11-2. Endoscope

The light-emitting apparatus having any of the structures described above may be used in endoscopes. An endoscope will be described below as an application example.

Figure 47:
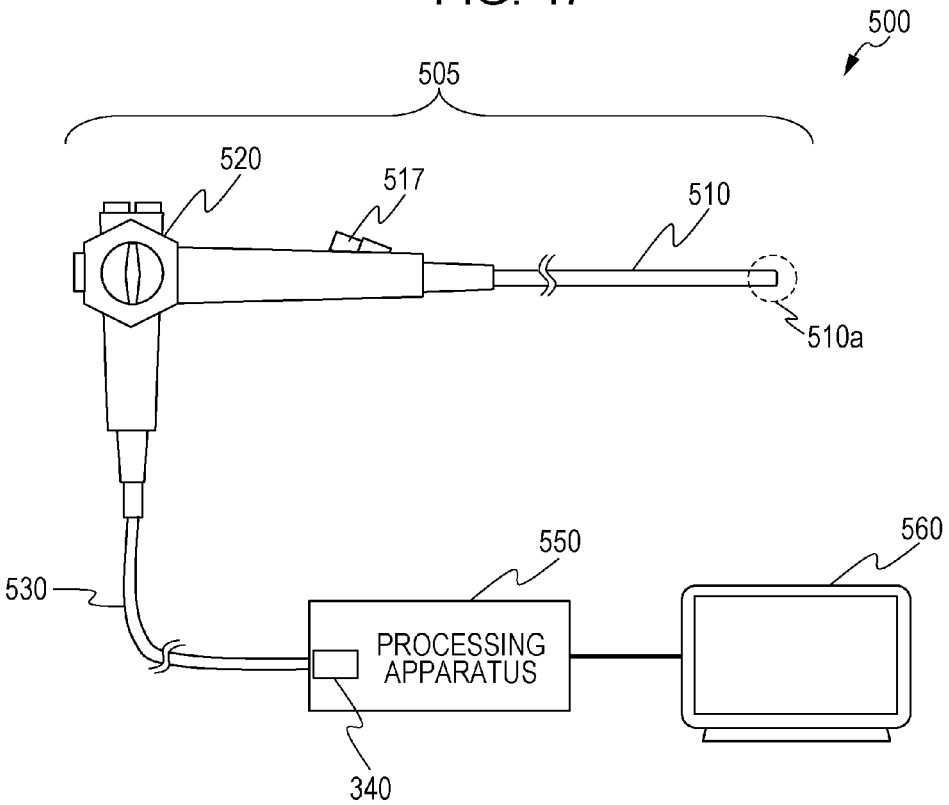
FIG. 47 is a schematic view of an endoscope system that includes a light-emitting apparatus according to the present disclosure.

FIG. 47 is a schematic view of an endoscope system 500 in which a light-emitting apparatus according to the present disclosure is used. The endoscope system 500 includes an endoscope 505, a processing apparatus 550 coupled to the endoscope 505, and a display unit 560 coupled to the processing apparatus 550. The term "couple", as used herein, refers to electrical connection that allows electric signals to be sent and received.

The endoscope 505 includes an insert 510 to be inserted into the body cavity, a forceps insertion opening 517, a manipulating portion 520, and a cable 530 to be coupled to the processing apparatus 550. The insert 510 is a long (or tubular) member made of a flexible material. The tip (front edge 510a) of the insert 510 may be configured to be bent by the operator.

The front edge 510a includes a light-emitting device, an imaging device, and an optical system. The light-emitting device irradiates an object with light. Reflected light is converged by the optical system and enters an imaging plane of the imaging device. In response to this, the imaging device outputs an electric signal depending on the amount of light received per pixel.

The manipulating portion 520 includes various switches and buttons for manipulating the endoscope 505. For example, the manipulating portion 520 may include a power switch, an on/off switch for illumination, an angle knob for changing the direction of the front edge 510a, a button for injecting air or water through the front edge 510a, and a release button for instructing the start and stop of imaging.

The cable 530 includes a light guide (i.e., an optical fiber) that can absorb excitation light from the excitation light source 340 at one end thereof and emit the excitation light from the other end thereof and a signal line for transmitting electric signals from the imaging device to the processing apparatus 550. In addition to these, the cable 530 may include a water and air supply pipe.

The processing apparatus 550 includes the excitation light source 340, a processor, such as a central processing unit (CPU), an image-processing circuit, a memory, and an input/output interface. Excitation light from the excitation light source 340 propagates through the light guide in the cable 530 and enters the light-emitting device in the front edge 510a. In response to this, the light-emitting device emits light. The processing apparatus 550 processes electric signals sent from the imaging device to produce and output image signals. The image signals are transmitted to the display unit 560.

Figure 48:
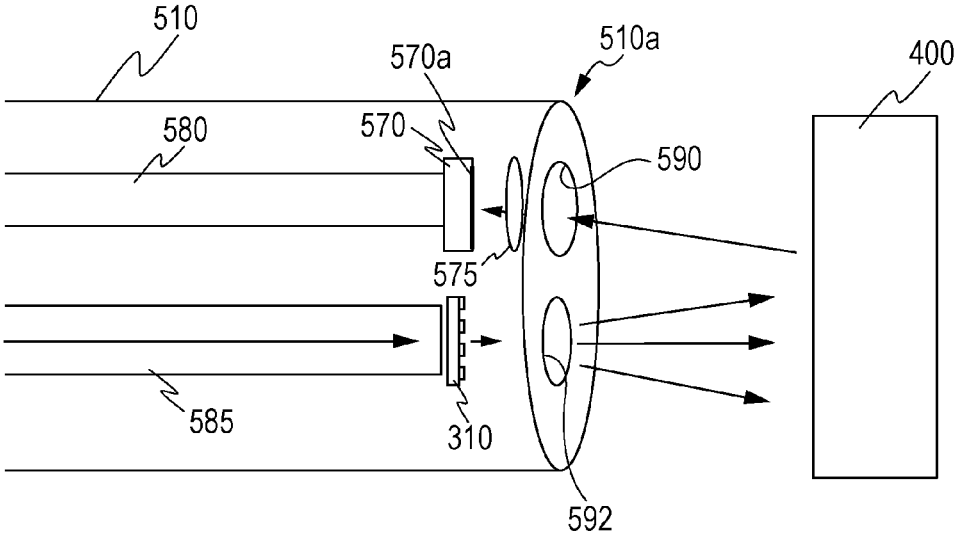
FIG. 48 is a simplified view of an inner structure of a front edge of an insert.

FIG. 48 is a simplified view of an inner structure of the front edge 510a of the insert 510. The endoscope 505 includes the light-emitting device 310, an imaging device 570, and an optical system 575 in the front edge 510a. The optical system 575 faces an imaging plane 570a of the imaging device 570.

The light-emitting device 310 is disposed near or in contact with an end of the light guide 585. A photoluminescent material is excited by excitation light output from the light guide 585 and emits light. The light is output through an illumination opening 592. An optical system for diffusing or converging light may be disposed near the illumination opening 592.

The imaging device 570 is coupled to a signal line 580. The signal line 580 transmits electric signals from the imaging device 570 to the processing apparatus 550. For example, the imaging device 570 is an image sensor, such as a charge coupled device (CCD) or a complementary metal oxide semiconductor (CMOS) sensor. Photodetector cells (e.g., photodiodes) are arranged on the imaging plane 570a of the imaging device 570. The photodetector cells output by photoelectric conversion an electric signal depending on the intensity of light received (also referred to as the amount of light received). The photodetector cells may face color filters. The color filters are arranged in two dimension (typically in a square grid). For example, the color filters may have a typical Bayer pattern, in which a unit of four color filters, that is, a red color filter, two green color filters, and a blue color filter is repeatedly arranged. Each photodetector cell and a color filter facing the photodetector cell constitute one pixel. The color filters may be omitted.

Light from the light-emitting device 310 travels toward the object 400 through the illumination opening 592. Part of the light is reflected from the object 400 and passes through an observation opening 590. The light passing through the observation opening 590 is converged onto the imaging plane 570a of the imaging device 570 through the optical system 575 including an objective lens. Consequently, an image of the object 400 is formed on the imaging plane 570a. The photodetector cells output an electric signal corresponding to the image. The signal line 580 transmits the electric signal to the processing apparatus 550.

The processing apparatus 550 produces an image signal based on the electric signal. For example, the processing apparatus 550 produces an image signal based on the electric signal after image processing, such as color interpolation, white balance adjustment, gamma correction, noise reduction, and/or color conversion. The image processing is performed by an image-processing circuit, such as a digital signal processor (DSP), in the processing apparatus 550. The image signal thus produced is transmitted from the processing apparatus 550 to the display unit 560. The display unit 560 displays an image based on the image signal. Thus, the operator can observe a picture of the object 400.

FIG. 48 illustrates a simplified inner structure of the front edge 510a. Typically, the front edge 510a may further include other components not illustrated in FIG. 48, such as an opening for forceps and a water and air supply nozzle. These will be briefly described below.

Figure 49:
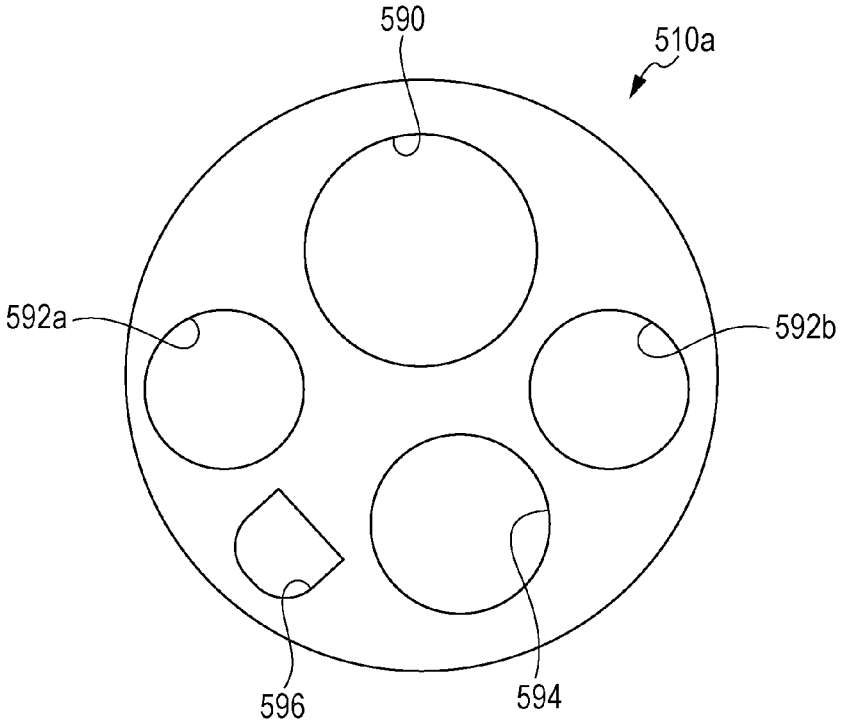
FIG. 49 is a schematic view of the front edge viewed from an object.

FIG. 49 is a schematic view of the front edge 510a viewed from the object 400. The front edge 510a includes two illumination openings 592a and 592b, an opening for forceps 594, and a water and air supply nozzle 596. The light-emitting device 310 and the light guide 585 are disposed at the back of each of the illumination openings 592a and 592b. Forceps inserted through the forceps insertion opening 517 pass through the opening for forceps 594. The water and air supply nozzle 596 injects water or air to wash away blood or mucus adhering to the front edge 510a. The illumination openings 592a and 592b are symmetrically disposed about the central axis. This can prevent a shadow from being formed during the imaging process.

The emission wavelength of a light source in the endoscope 505 according to the present embodiment may be in a blue wavelength band and a green wavelength band. For example, the light-emitting device 310 includes a first emission region for emitting light in a green wavelength band in the normal direction and a second emission region for emitting light in a blue wavelength band in the normal direction. The first and second emission regions are arranged in a direction perpendicular to or parallel to the photoluminescent layer. In the first emission region, the relationship $\lambda_a/n_{wav\text{-}a}<D_{int\text{-}a}<\lambda_a$ is satisfied, where $D_{int\text{-}a}$ is the distance (i.e., period) between adjacent projections or recesses, and $n_{wav\text{-}a}$ is the refractive index of the photoluminescent layer for light having the wavelength $\lambda_a$ in the green wavelength band. Likewise, in the second emission region, the relationship $\lambda_b/n_{wav\text{-}b}<D_{int\text{-}b}<\lambda_b$ is satisfied, where $D_{int\text{-}b}$ is the distance (i.e., period) between adjacent projections or recesses, and $n_{wav\text{-}b}$ is the refractive index of the photoluminescent layer for light having the wavelength $\lambda_b$ in the blue wavelength band.

If excitation light in the blue wavelength band is used as a light source, the light-emitting device 310 may include the first emission region alone. In this case, the light-emitting device 310 is configured to transmit part of the blue excitation light.

Advantageously, the endoscope according to the present embodiment can easily identify a very small lesion site, such as cancer. Hemoglobin in blood absorbs blue light. Thus, blue light irradiation allows capillary vessels on the surface to be emerged. Because blue light alone is insufficient in quantity, green light is also used in the present embodiment. The combined use can produce generally clear images.

In particular, in the present embodiment, the light-emitting device 310 directly emits narrow-band blue light and green light. This advantageously obviates the need for traditional color filters. This advantage will be described in detail below.

Figure 50:
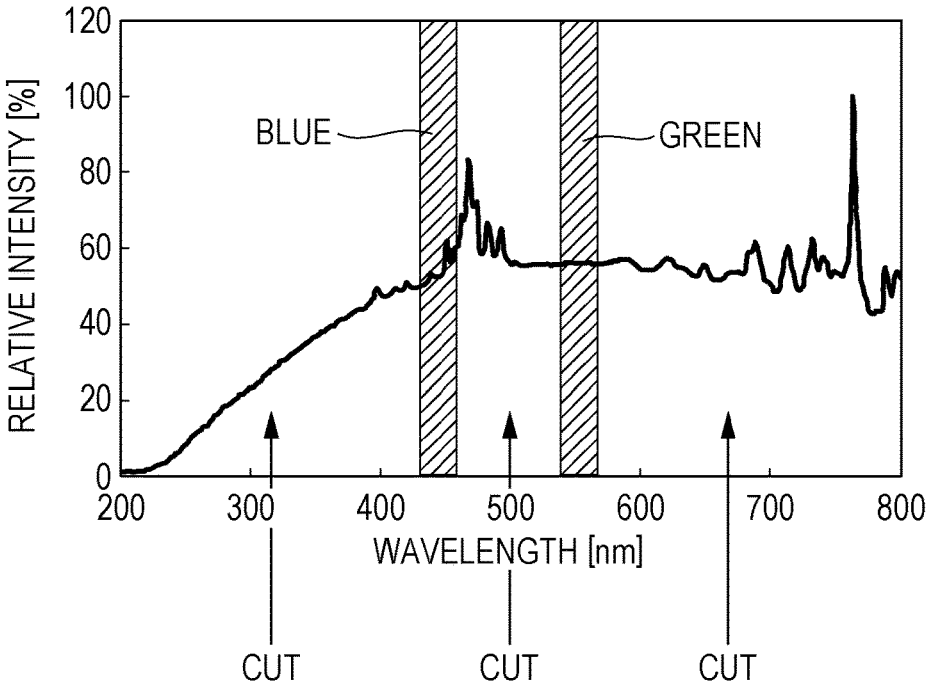
FIG. 50 is an emission spectrum of a known xenon lamp.

FIG. 50 is an emission spectrum of a known xenon lamp. The emission spectrum has a broad intensity distribution throughout the entire wavelength band of visible light. Thus, the use of light in a blue wavelength band and light in a green wavelength band requires color filters for removing light having the other wavelength bands. Such color filters increase optical loss and decrease efficiency.

Figure 51:
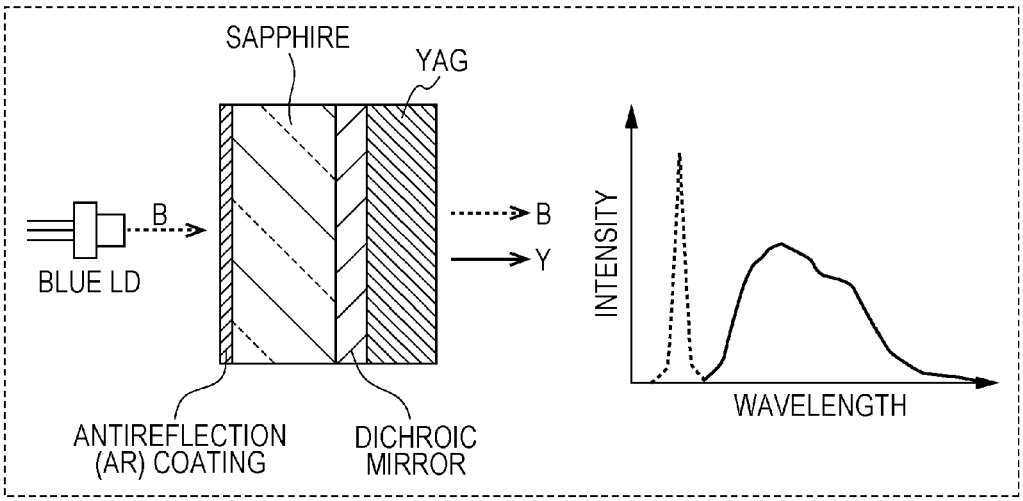
FIG. 51 illustrates the structure and emission spectrum of a known typical LED white light source.

FIG. 51 illustrates the structure and emission spectrum of a known typical LED white light source. The LED white light source produces white light by using a fluorescent substance, such as YAG, that emits yellow fluorescent light (i.e., red light and green light) in response to excitation light in a blue wavelength band, in combination with blue light passing through the fluorescent substance. Also in this case, a color filter that can selectively transmit green light is required to produce narrow-band green light from yellow light. This decreases light-use efficiency.

Figure 52:
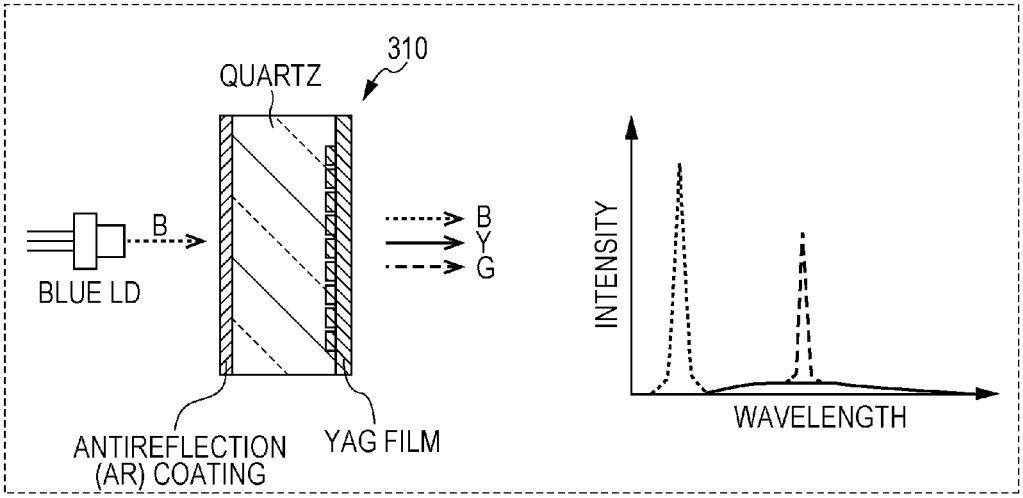
FIG. 52 illustrates the structure and emission spectrum of a light source that includes a light-emitting device according to an embodiment of the present disclosure.

FIG. 52 illustrates the structure and emission spectrum of a light source that includes the light-emitting device 310. In this structure, blue light from a blue LD is used as excitation light. A periodic structure is disposed between a light-transmissive quartz layer and a photoluminescent layer. An antireflection (AR) coating is disposed on an excitation light incident surface of the light-transmissive layer. The periodic structure is configured to output light in a green wavelength band in a direction approximately perpendicular to the photoluminescent layer. More specifically, the relationship $\lambda_a/n_{wav\text{-}a}<D_{int}<\lambda_a$ is satisfied, where $D_{int}$ is the distance (i.e., period) between adjacent projections or recesses, and $n_{wav\text{-}a}$ is the refractive index of the photoluminescent layer for light in the green wavelength band $\lambda_a$. The photoluminescent layer is a thin film containing YAG and emits light in a yellow (i.e., red and green) wavelength band in response to excitation light. However, the periodic structure is configured to output light in the green wavelength band in the perpendicular direction, and therefore most of light emitted from the light-emitting device 310 in the perpendicular direction includes green light and blue light passing through the light-emitting device 310.

In FIG. 52, the light-emitting device 310 directly emits narrow-band blue light and green light. Thus, intended narrow-band light can be produced without color filters. Thus, the light-emitting device 310 can greatly reduce the optical loss of known light sources.

A light-emitting device according to the present disclosure used in endoscopes that utilize narrow-band imaging can obviate the need for color filters and improve light-use efficiency. Thus, endoscopes having high efficiency in addition to the advantages of a decrease in size and easy maintenance described above can be provided.

These endoscopes are for illustrative purposes only, and an endoscope according to the present disclosure may have another structure. For example, at least one of the light-emitting device 310 and the imaging device 570 may be disposed away from the front edge 510a. For example, at least one of the light-emitting device 310 and the imaging device 570 may be disposed near or within the manipulating portion 520 or the processing apparatus 550. An endoscope according to the present disclosure may be configured to emit white light. In such a case, the light-emitting device 310 may have one of the structures described above with reference to FIGS. 32A to 34B. A light-emitting device according to the present disclosure can be widely applied to known endoscopes, such as those described in Japanese Unexamined Patent Application Publication No. 2013-000175.

Wavelengths used for endoscopes will be described below.

FIGS. 53A to 53F illustrate wavelengths used for endoscopes. In FIGS. 53A to 53F, excitation light from the excitation light source 340 is directed obliquely with respect to a direction perpendicular to the photoluminescent layer of the light-emitting device 310, and light from the light-emitting device 310 is transmitted to the optical fiber 320 through a lens 330.

Figure 53A:
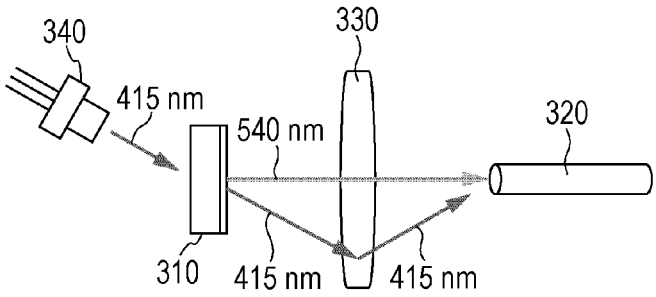
FIG. 53A is a first figure of wavelengths used for an endoscope.

In FIG. 53A, light having a wavelength of 415 nm and light having a wavelength of 540 nm are used as endoscope illumination light. For example, light having a wavelength of 415 nm is part of excitation light from the excitation light source 340 including a laser diode. For example, light having a wavelength of 540 nm is part of yellow light from a photoluminescent layer containing YAG. Light having a wavelength of 415 nm passing through the light-emitting device 310 and light having a wavelength of 540 nm emitted from the light-emitting device 310 in the front direction converge onto the optical fiber 320 through the lens 330. Wavelengths to be used are not limited to these wavelengths and may be other wavelengths. For example, light having a wavelength in the range of 400 to 430 nm, desirably 410 to 420 nm, and light having a wavelength in the range of 520 to 560 nm, desirably 530 to 550 nm, may be used.

An endoscope according to an embodiment of the present disclosure may utilize a wavelength (390 to 470 nm) for autofluorescence imaging (AFI), that is, for observing intrinsic fluorescence of a fluorescent substance, such as collagen, and a wavelength (540 to 560 nm), which is absorbed by hemoglobin in blood. Use of light in these two wavelengths bands enables special light observation that highlights a neoplastic lesion and a normal mucosa with different color tones.

Figure 53B:
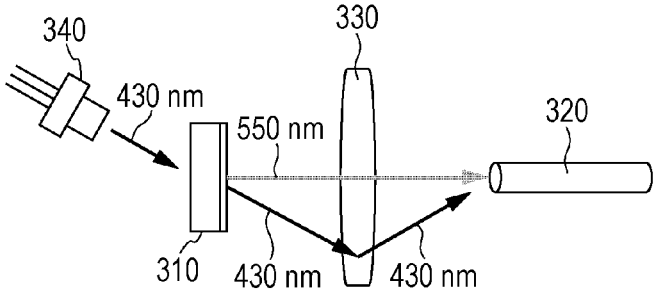
FIG. 53B is a second figure of wavelengths used for an endoscope.
Figure 53C:
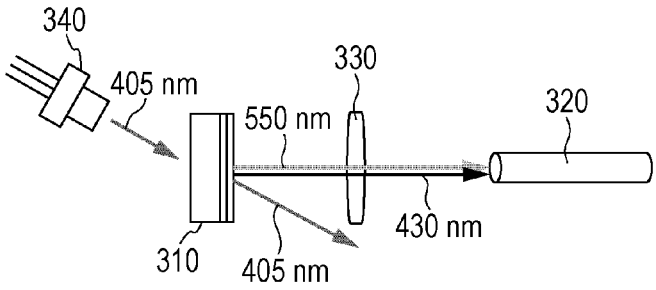
FIG. 53C is a third figure of wavelengths used for an endoscope.

FIGS. 53B and 53C illustrate the structures of endoscopes for use in such applications. In FIG. 53B, light having a wavelength of 430 nm and light having a wavelength of 550 nm are used as endoscope illumination light. For example, light having a wavelength of 430 nm is part of excitation light from the excitation light source 340 including a laser diode. For example, light having a wavelength of 550 nm is part of yellow light from a photoluminescent layer containing YAG. Light having a wavelength of 430 nm passing through the light-emitting device 310 and light having a wavelength of 550 nm emitted from the light-emitting device 310 in the front direction converge onto the optical fiber 320 through the lens 330. FIG. 53C is the same as FIG. 53B in that light having a wavelength of 430 nm and light having a wavelength of 550 nm are used as endoscope illumination light but is different from FIG. 53B in that the light-emitting device 310 emits both of them. In FIG. 53C, light having a wavelength of 405 nm from the excitation light source 340 enters the light-emitting device 310. The light-emitting device 310 includes a layered structure of a periodic structure for outputting light having a wavelength of 550 nm in the front direction and a periodic structure for outputting light having a wavelength of 430 nm in the front direction. Examples of light-emitting materials to be used include a material that emits light including light having a wavelength of 550 nm, such as YAG, and a material that emits light including light having a wavelength of 430 nm, such as barium aluminum oxide (BAM). In FIG. 53C, light having a wavelength of 430 nm and light having a wavelength of 550 nm emitted from the light-emitting device 310 in the front direction travel to the optical fiber 320 through the lens 330. Excitation light having a wavelength of 405 nm passing through the light-emitting device 310 does not enter the lens 330 and does not reach the optical fiber 320.

An endoscope according to an embodiment of the present disclosure may also be used for infrared light imaging (IRI). After an infrared indicator for infrared absorption is injected into a vein, irradiation with infrared light in two wavelengths bands (790 to 820 nm and 905 to 970 nm) enables special light observation that highlights information on blood vessels and blood flows in a deep portion of a mucosa, which are difficult to visually recognize in observation with ordinary light.

Figure 53D:
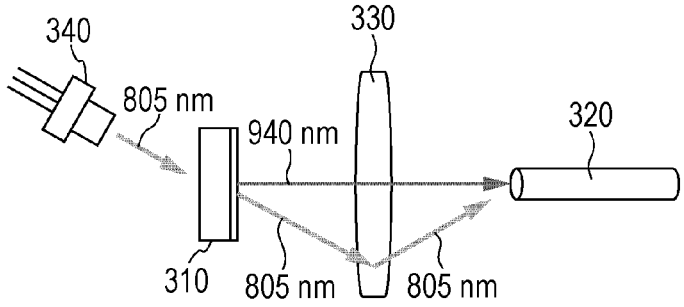
FIG. 53D is a fourth figure of wavelengths used for an endoscope.
Figure 53E:
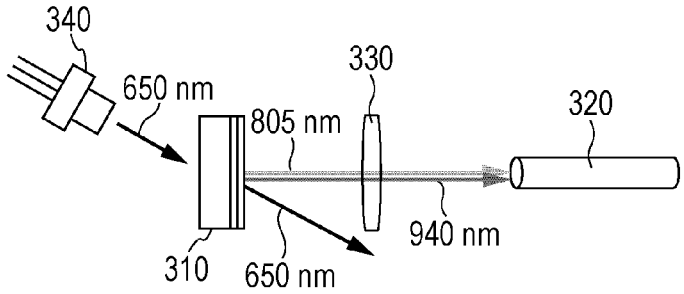
FIG. 53E is a fifth figure of wavelengths used for an endoscope.

FIGS. 53D and 53E illustrate the structures of endoscopes for use in such infrared imaging. In FIG. 53D, light having a wavelength of 805 nm and light having a wavelength of 940 nm are used as endoscope illumination light. For example, light having a wavelength of 805 nm is part of excitation light from the excitation light source 340 including a laser diode. For example, light having a wavelength of 940 nm is light from a photoluminescent layer containing quantum dots. Light having a wavelength of 805 nm passing through the light-emitting device 310 and light having a wavelength of 940 nm emitted from the light-emitting device 310 in the front direction converge onto the optical fiber 320 through the lens 330. FIG. 53E is the same in that light having a wavelength of 805 nm and light having a wavelength of 940 nm are used as endoscope illumination light but is different from FIG. 53D in that the light-emitting device 310 emits both of them. In FIG. 53E, light having a wavelength of 650 nm from the excitation light source 340 enters the light-emitting device 310. The light-emitting device 310 includes a layered structure of a periodic structure for outputting light having a wavelength of 805 nm in the front direction and a periodic structure for outputting light having a wavelength of 940 nm in the front direction. Examples of light-emitting materials to be used include gadolinium gallium garnet (GGG) phosphors that emit light having a wavelength of 805 nm and quantum dots that emit light having a wavelength of 940 nm. In FIG. 53E, near-infrared light having a wavelength of 805 nm and near-infrared light having a wavelength of 940 nm emitted from the light-emitting device 310 in the front direction travel to the optical fiber 320 through the lens 330. Excitation light having a wavelength of 650 nm passing through the light-emitting device 310 does not enter the lens 330 and does not reach the optical fiber 320.

An endoscope according to an embodiment of the present disclosure may also be used in an indocyanine green (ICG) fluorescence method. ICG is excited by near-infrared light having a certain wavelength (e.g., a wavelength of 774 nm) and emits near-infrared fluorescent light having another wavelength (e.g., 805 nm). In the ICG fluorescence method, ICG injected into the body is irradiated with, for example, excitation light having a wavelength of 774 nm, and the resulting fluorescent light having a wavelength of 805 nm is detected by an infrared camera. The ICG fluorescence method enables minimally invasive convenient observation of body tissues, such as blood vessels and lymphatic vessels, under the tissue surface.

Figure 53F:
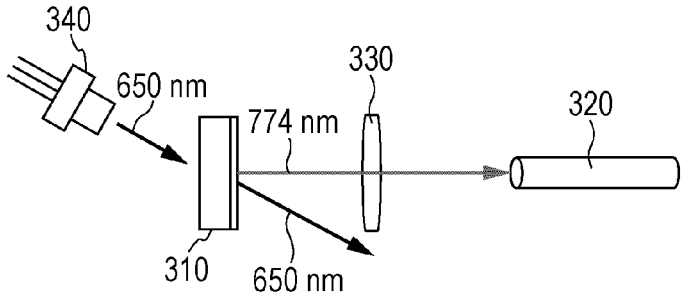
FIG. 53F is a sixth figure of wavelengths used for an endoscope.

FIG. 53F illustrates the structure of an endoscope or an imaging system for use in the ICG fluorescence method. In FIG. 53F, light having a wavelength of 774 nm is used as illumination light. For example, light having a wavelength of 774 nm is emitted from a photoluminescent layer containing GGG that emits light in response to excitation light having a wavelength of 650 nm. Light having a wavelength of 774 nm emitted from the light-emitting device 310 in the front direction travels to the optical fiber 320 through the lens 330. Excitation light having a wavelength of 650 nm passing through the light-emitting device 310 does not enter the lens 330 and does not reach the optical fiber 320. Although not shown in FIG. 53F, an imaging system for use in the ICG fluorescence method further includes an imaging device for detecting fluorescent light (near-infrared light) produced by ICG.

11-3. Underwater Fiber Illumination

A light-emitting apparatus according to the present disclosure may be used for underwater fiber illumination. Examples of a light-emitting apparatus applied to underwater fiber illumination will be described below.

Figure 54A:
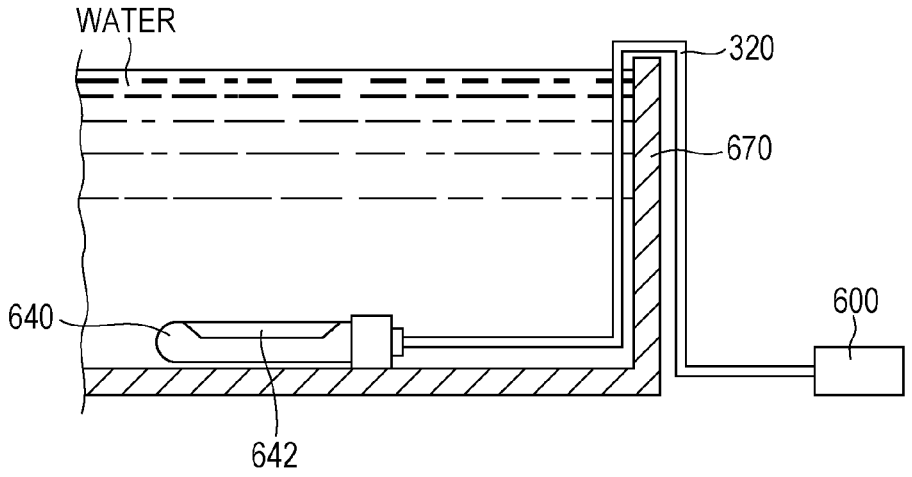
FIG. 54A is a schematic view of the structure of an underwater fiber lighting apparatus.

FIG. 54A is a schematic view of the structure of an underwater fiber lighting apparatus. The lighting apparatus includes a light source apparatus 600, an illumination unit 640, and an optical fiber 320 for coupling the light source apparatus 600 to the illumination unit 640. The illumination unit 640 is disposed in water in a water tank 670, and the light source apparatus 600 is disposed outside the water tank 670. Light from the light source apparatus 600 propagates through the optical fiber 320 and is output from an illumination window 642 of the illumination unit 640, thereby illuminating water.

Figure 54B:
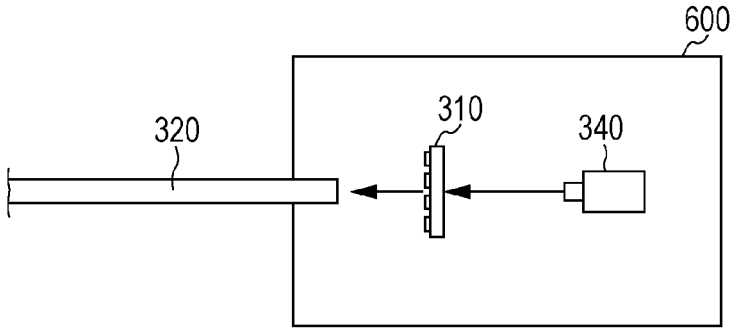
FIG. 54B is a schematic view of the structure of a light source apparatus.

FIG. 54B is a schematic view of the structure of the light source apparatus 600. The light source apparatus 600 includes a light-emitting device 310 and an excitation light source 340. The light-emitting device 310 has the same structure as one of the light-emitting devices according to the embodiments described above. Excitation light from the excitation light source 340 excites a photoluminescent material in the light-emitting device 310 and induces light emission. Light from the light-emitting device 310 is transmitted to the illumination unit 640 through the optical fiber 320. The light source apparatus 600 may include a lens between the light-emitting device 310 and the optical fiber 320. The lens converges light from the light-emitting device 310 onto the optical fiber 320.

Lamp light sources, for example, as disclosed in Japanese Unexamined Patent Application Publication No. 1-262959 have been used for underwater fiber illumination. Lamp light sources have high optical losses and power consumption due to low coupling efficiency in optical fibers. As disclosed in Japanese Unexamined Patent Application Publication No. 2003-257204, a water tank lighting apparatus that includes a cold-cathode tube and a power supply cable to be used in water has a high risk of electric leakage.

The structure according to the present application example can increase the coupling efficiency between the light-emitting device 310 and the optical fiber 320 because the light-emitting device 310 has high directionality. Furthermore, the use of the optical fiber 320 allows the light source apparatus 600 and a power supply to be placed outside the water tank 670, thus eliminating the risk of electric leakage. Thus, an underwater fiber lighting apparatus having high efficiency and safety can be provided.

The structure of an underwater fiber lighting apparatus is not limited to the structure illustrated in FIGS. 54A and 54B and may be subjected to various modifications. For example, as disclosed in Japanese Unexamined Patent Application Publication No. 1-262959, fiber illumination for a fountain can be provided by placing an illumination unit near a fountain nozzle. For example, as disclosed in Japanese Unexamined Patent Application Publication No. 56-72637, fiber illumination for illuminating the area around fishnet in the sea can be realized using optical fibers coupled to a light source apparatus placed on a boat. Target fish can be efficiently harvested by irradiating the underwater with light in a wavelength band suitable for the behavior of the fish. The use of a light-emitting device according to the present disclosure can reduce optical loss and power consumption and contribute to improved fuel efficiency of fishing boats. For example, as disclosed in Japanese Unexamined Patent Application Publication No. 4-95864, a structure according to the present disclosure may be applied to apparatuses for detecting defects in underwater structures. For example, a structure according to the present disclosure may be applied to damage inspection of cooling water pools in nuclear reactors. Defects in a structure in a cooling water pool can be examined by irradiating the structure with light output from an optical fiber coupled to a light source placed outside the cooling water pool and detecting reflected light with an imaging device. Because the light source is placed outside water, a battery or a light source can be easily replaced in case of failure, such as a dead battery.

11-4. Fiber Illumination for Space Probe

Examples of a light-emitting apparatus according to the present disclosure applied to a lighting apparatus for a space probe will be described below.

Figure 55:
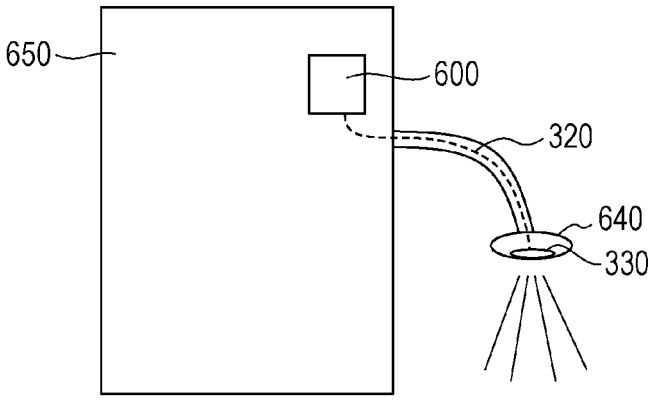
FIG. 55 is a simplified view of a space probe that includes a fiber lighting apparatus according to an embodiment of the present disclosure.

FIG. 55 is a schematic view of a space probe 650 that includes a fiber lighting apparatus according to an embodiment of the present disclosure. FIG. 55 is a simplified view of the structure of the main body of the space probe 650. The specific structure of the space probe 650 may be the same as one of the space probes disclosed in David S. F. Prtree, "Mir Hardware Heritage", NASA Reference Publication 1357, Johnson Space Center Reference Series, March 1995 (http://ston.jsc.nasa.gov/collections/TRS/#techrep/RP1357.pdf), for example. The lighting apparatus includes a light source apparatus 600 within the space probe 650, an illumination unit 640 including a lens 330 outside the space probe 650, and an optical fiber 320 for coupling the light source apparatus 600 to the illumination unit 640. The light source apparatus 600 has the same structure as the light source apparatus 600 illustrated in FIG. 54B. Light from a light-emitting device 310 in the light source apparatus 600 is output from the space probe 650 through the optical fiber 320 and the lens 330. The lens 330 may be omitted.

Such a structure can realize compact, high-efficiency, low power consumption illumination for space probes. Known lighting apparatuses for space probes or spacecraft generally include a lamp light source, as disclosed in Japanese Unexamined Utility Model Registration Application Publication No. 61-157098. Thus, the known lighting apparatuses are large and inefficient and consume much power. High power consumption results in a short battery life, which may be a critical problem in space exploration. The use of a light-emitting device according to the present disclosure can reduce optical loss and power consumption and prolong battery life.

Lighting apparatuses for use in space should meet the following requirements. (1) Breakage of a lighting apparatus scatters the least amount of debris. (2) Heat dissipation is possible even in a vacuum. (3) Use of reliable structures and materials of high durability even in a vacuum. (4) Durability to withstand very low temperatures and very high temperatures.

The present application example can meet all of these requirements. Regarding (1), only an end of the optical fiber 320 or the illumination unit including the lens 330 is disposed outside the spacecraft, and the light source apparatus 600 is disposed within the spacecraft. Thus, the fiber lighting apparatus is rarely broken, and no debris associated with breakage of the light source apparatus 600 occurs. Regarding (2), the light source apparatus 600 is disposed within the spacecraft, and the optical fiber 320, which generates no heat, is disposed outside the spacecraft. Thus, the light source apparatus 600 can dissipate heat within the spacecraft. Regarding (3), resin materials, such as adhesives, generate gases and should not be disposed outside the spacecraft. Air remaining after sealing and bonding may cause a breakage in a vacuum. In the present application example, there is no concern for such a breakage because the light source apparatus 600 is disposed within the spacecraft. Furthermore, the optical fiber 320 is composed essentially of glass and a resin cover for protecting the glass and is therefore durable even in a vacuum. Regarding (4), although durability at a temperature range in the range of approximately −40° C. to 100° C. is sufficient on earth, the temperature in space is lower in the shade and higher in the sun. Resin materials may not withstand a low-temperature or high-temperature environment in space. In the present application example, the optical fiber 320 is composed mainly of glass and is therefore durable in both low-temperature and high-temperature environments.

11-5. Fiber Illumination for High Place Illumination

A light-emitting apparatus according to the present disclosure that includes a light-emitting device and an optical fiber in combination is also suitable as an illuminator installed in a high place. Examples of lighting apparatuses installed in high places include lighting apparatuses for stadiums, expressways, tunnels, and bridges.

Figure 56:
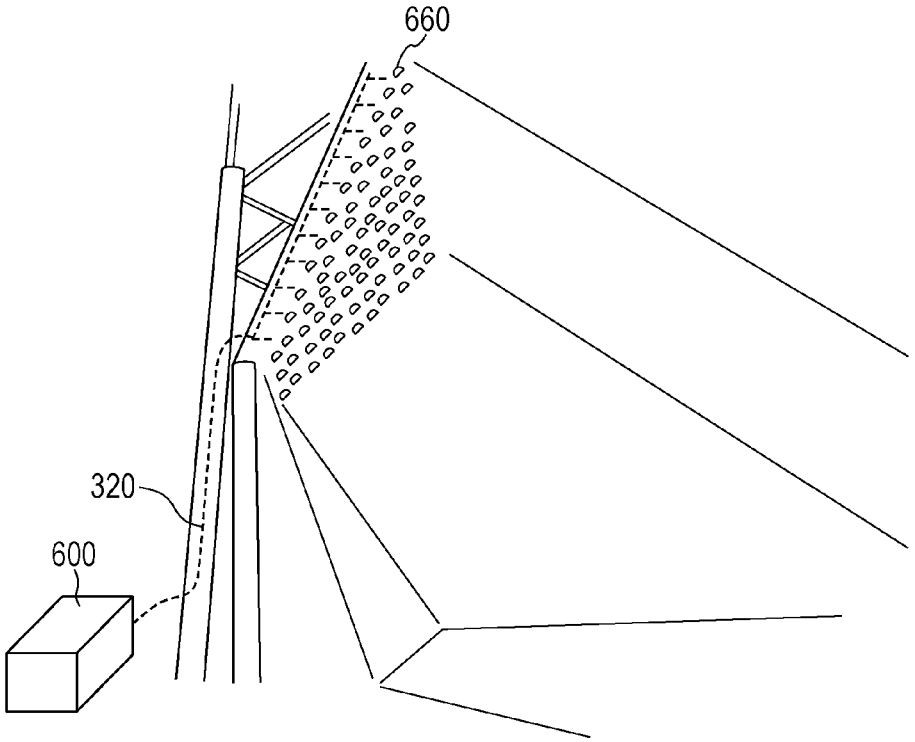
FIG. 56 is a schematic view of an optical fiber lighting apparatus for use in stadiums.

FIG. 56 is a schematic view of an optical fiber lighting apparatus for use in stadiums as an example of a light-emitting apparatus for high place illumination. This lighting apparatus includes a light source apparatus 600, an optical fiber 320, and illumination units 660. The light source apparatus 600 has the structure as illustrated in FIG. 54B and is placed on the ground (i.e., in a low place). The optical fiber 320 is divided into two or more optical fibers and couples the light source apparatus 600 to the illumination units 660. Each of the illumination units 660 is disposed near an end of the optical fiber 320 and is installed in a high place. The illumination units 660 may include a lens or a diffuser plate. Light propagating through the optical fiber 320 is output from the illumination units 660.

Such a structure can provide a compact and efficient stadium lighting apparatus having high maintainability. In known stadium illumination, many lamp light sources are installed in high places, which makes installation and maintenance (such as lamp replacement) difficult. Furthermore, large-scale housings that can withstand high wind pressure in high places are required. In the present application example, the optical fiber 320 can transmit light from the light source apparatus 600 disposed on the ground to the illumination units 660 disposed in a high place. Thus, a compact lighting apparatus that is easy to install and has high maintainability can be provided.

Figure 57:
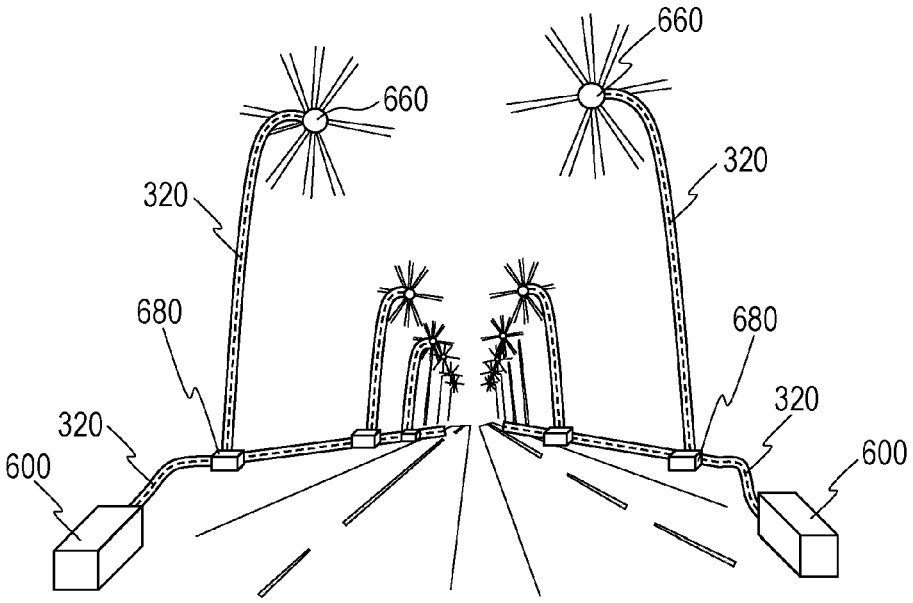
FIG. 57 is a schematic view of a lighting apparatus for use in expressways.

FIG. 57 is a schematic view of a lighting apparatus for use in expressways as another example of a light-emitting apparatus for high place illumination. This lighting apparatus include light source apparatuses 600, optical fibers 320, optical dividers 680, and illumination units 660. Also in this example, the light source apparatus 600 has the structure as illustrated in FIG. 54B and is placed on the ground (i.e., in a low place). The light source apparatuses 600 are coupled to the optical fibers 320. The optical fibers 320 are coupled to other optical fibers 320 via the optical dividers 680. The other optical fibers 320 extend to high places. The illumination units 660 for outputting light are disposed at an end of each of the optical fibers 320 extending to high places. As in the example described above, the illumination units 660 may include a lens or a diffuser plate.

Such a structure can provide a smaller expressway lighting apparatus having higher maintainability than known expressway lighting apparatuses that include many lamps in high places.

Such a structure can also be applied to bridges as well as expressways. Bridges are located above rivers, above the ocean, and in the mountains. Illuminators for bridges are disposed in high places and in strong winds. Installation and maintenance of illuminators involve considerable danger. Thus, optical fiber illumination according to the present application example is particularly desired.

Figure 58:
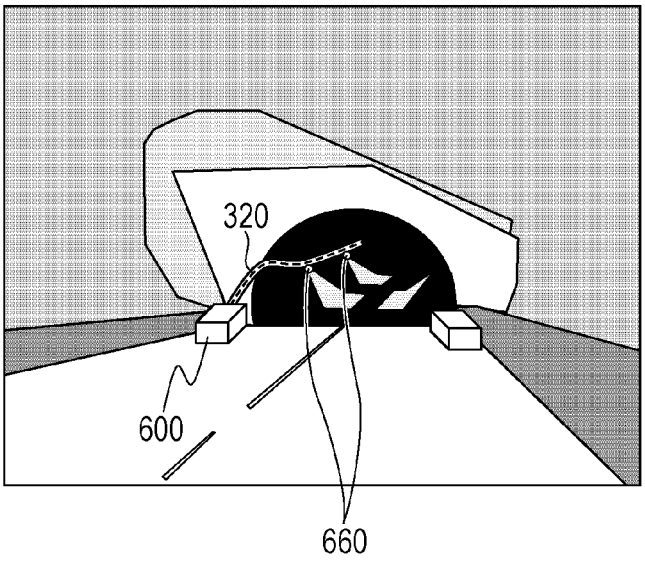
FIG. 58 is a schematic view of a lighting apparatus for use in tunnels.

FIG. 58 is a schematic view of a lighting apparatus for use in tunnels as another example of a light-emitting apparatus for high place illumination. As in the example described above, the lighting apparatus includes a light source apparatus 600, an optical fiber 320, and illumination units 660. The light source apparatus 600 is disposed near a tunnel entrance and is coupled to the illumination units 660 via the optical fiber 320 (and an optical divider). The illumination units 660 are disposed in the tunnel. The light source apparatus 600, the optical fiber 320, and the illumination units 660 have the structures as described above.

Such a structure can provide a smaller tunnel lighting apparatus having higher maintainability than known tunnel lighting apparatuses that include many lamps in high places over a long distance.

A fiber lighting apparatus according to the present application example will be described in detail below.

Figure 59:
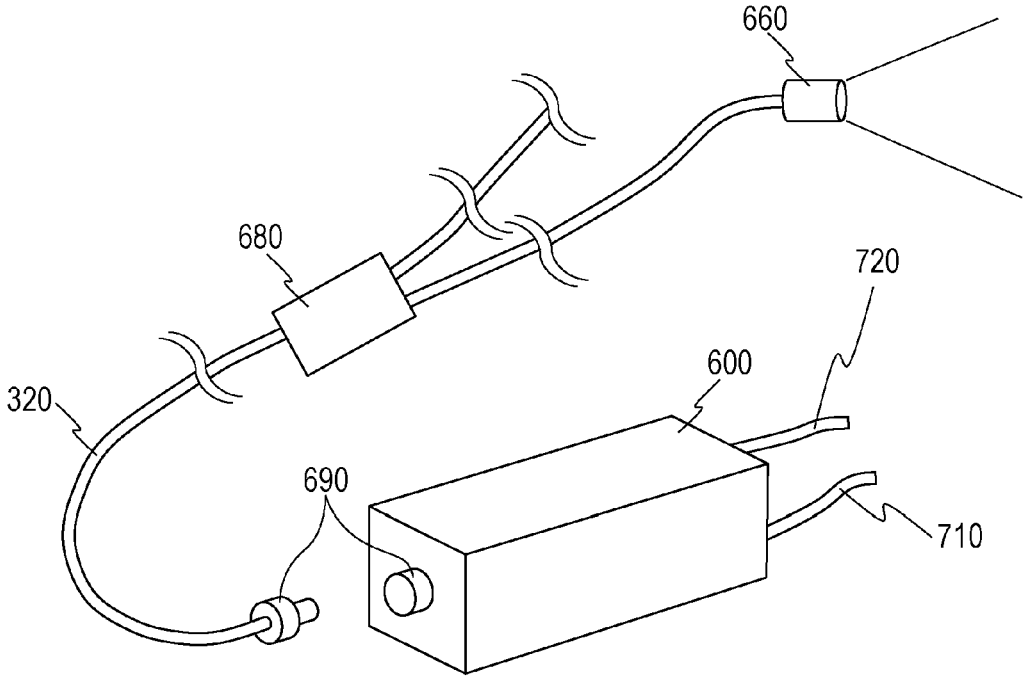
FIG. 59 is an explanatory view of a detailed structure of a fiber lighting apparatus.

FIG. 59 is an explanatory view of a detailed structure of a fiber lighting apparatus used in the examples described above. A light source apparatus 600 and an optical fiber 320 have connectors 690 and are coupled together via the connectors 690. The light source apparatus 600 is coupled to a power supply cable 710 and a communication cable 720. The light source apparatus 600 is supplied with electric power from a power supply through the power supply cable 710 and communicates with another equipment (e.g., a remote computer) through the communication cable 720. The optical fiber 320 is coupled to another optical fiber via an optical divider 680. An illumination unit 660, which is to be disposed in a high place or a place in which the illumination unit 660 is difficult to install, is coupled to the light source apparatus 600 through at least one optical fiber 320 and the optical divider 680. Light from the one light source apparatus 600 is branched through the optical fiber 320 and is transmitted to the illumination units 660. This can significantly reduce maintenance workload. In such a structure in which light is transmitted from the light source apparatus 600 to the illumination units 660 through optical fibers 320 (i.e., optical fiber cables) coupled together by the optical dividers 680, the optical fibers 320 between the light source apparatus 600 and the illumination units 660 may be considered to be a single optical fiber. Such an optical fiber includes optical fiber cables and an optical divider for coupling the optical fiber cables together.

Figure 60:
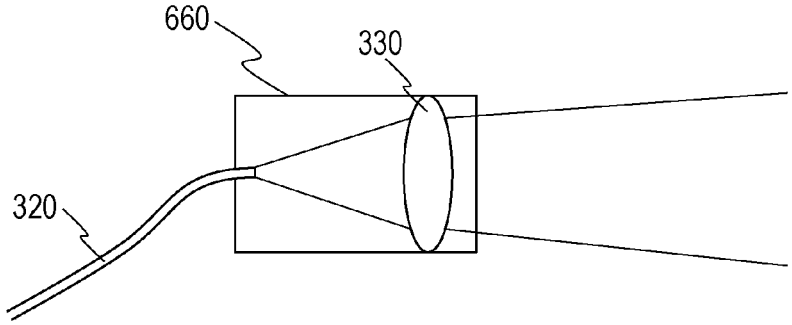
FIG. 60 is a schematic view of the structure of an illumination unit.

FIG. 60 is a schematic view of the structure of an illumination unit 660. The illumination unit 660 includes a lens 330 near an end of an optical fiber 320. The lens 330 is not limited to one illustrated in the figure and may be an aspheric lens, a singlet lens, a doublet lens, or a triplet lens. The lens may be adjusted so as to change the emission angle. The illumination unit 660 may not include the lens 330. The illumination unit 660 may include a light diffuser plate instead of the lens 330.

Figure 61A:
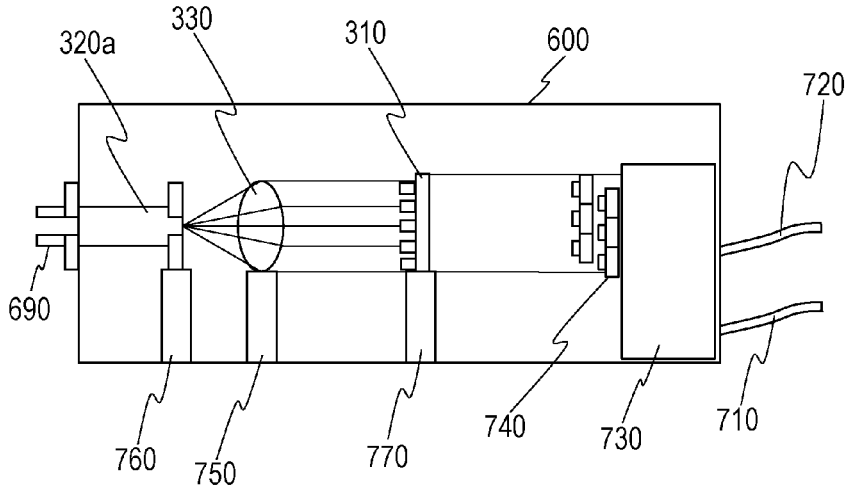
FIG. 61A is a cross-sectional view of a detailed structure of the light source apparatus.

FIG. 61A is a cross-sectional view of a detailed structure of the light source apparatus 600. The light source apparatus 600 includes laser diodes 740 (an excitation light source) for emitting excitation light, a light-emitting device 730 for emitting light in response to the excitation light, and a lens 330 for converging light from the light-emitting device 730 onto the optical fiber 320a. The optical fiber 320a is coupled to an external optical fiber 320 via an optical connector 690. The optical fiber 320a is fixed to a fiber jig 760, and the lens 330 is fixed to a lens jig 750. For example, the lens 330 may be an aspheric lens, a singlet lens, a doublet lens, or a triplet lens. The light-emitting device 310 is fixed to a jig 770. The laser diodes 740 are arranged in parallel with a photoluminescent layer of the light-emitting device 310. Thus, light can be emitted from portions in the photoluminescent layer of the light-emitting device 310. The laser diodes 740 are supplied with electric power from a laser power supply 730. The laser power supply 730 is supplied with electric power from an external power supply through a power supply cable 710. The laser power supply 730 may include a secondary battery. The laser power supply 730 is also coupled to a communication cable 720. Control signals for controlling the output of the laser diodes 740 may be input from a computer remote from the light source apparatus 600 through the communication cable 720. Thus, the laser power supply 730 can control light emission of the light-emitting device 310. The laser power supply 730 includes a control circuit for controlling the output of the laser diodes 740 and a communication circuit for transmission and reception of information. Although the laser diodes 740 are herein used as excitation light sources, LEDs may be used as excitation light sources instead of the laser diodes 740.

Figure 61B:
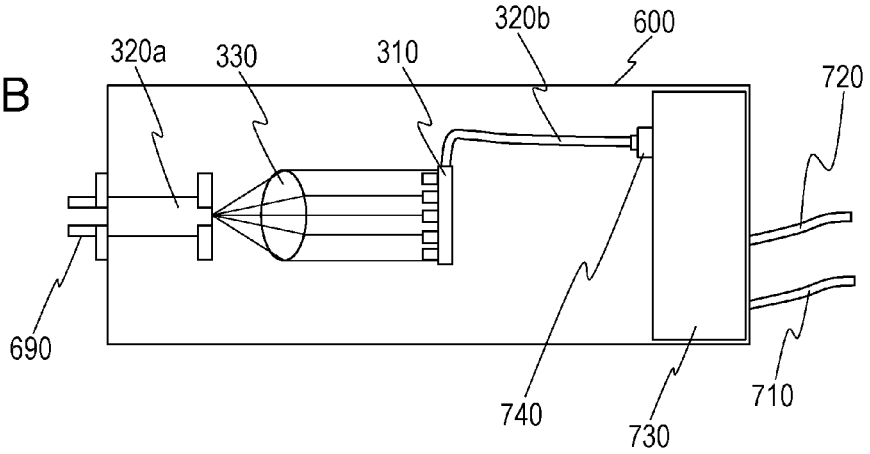
FIG. 61B is a top view of another structure of the light source apparatus.

FIG. 61B is a top view of another structure of the light source apparatus 600. The light source apparatus 600 is different from one illustrated in FIG. 61A in that only one laser diode 740 is used, and excitation light is transmitted from the laser diode 740 to a side surface of the light-emitting device 310 through an optical fiber 320b. This structure can also have the same function as that illustrated in FIG. 61A.

Figure 61C:
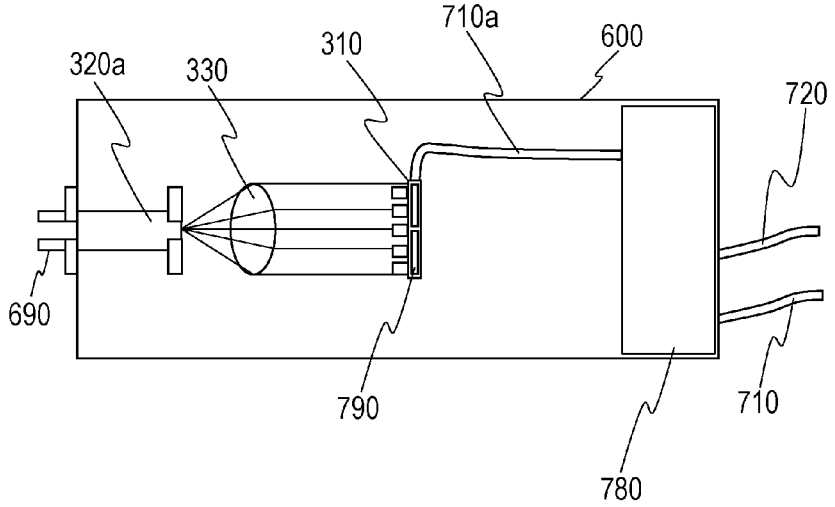
FIG. 61C is a top view of still another structure of the light source apparatus.
Figure 61D:
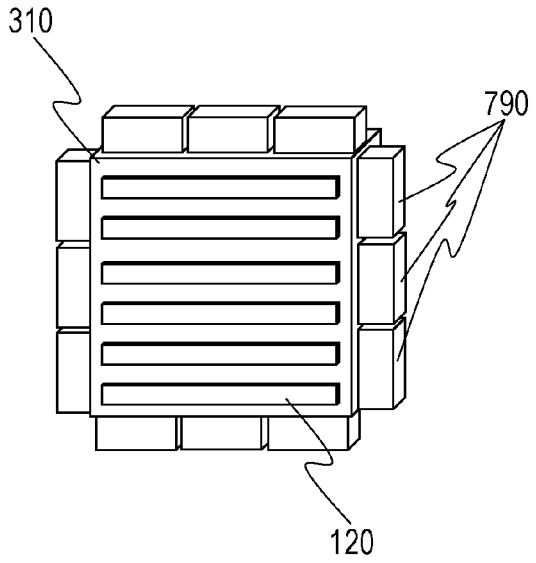
FIG. 61D is an enlarged view of a light-emitting device in the light source apparatus illustrated in FIG. 61C.

FIG. 61C is a top view of still another structure of the light source apparatus 600. The light source apparatus 600 is different from those described above in that the excitation light source is light-emitting diodes (LEDs) 790 instead of the laser diode(s). As illustrated in an enlarged view of FIG. 61D the LEDs 790 surround a light-emitting device 310. The LEDs 790 are supplied with electric power from an LED power supply 780 through a power supply cable 710a. The LED power supply 780 is coupled to a communication cable 720. Control signals for controlling the output of the LEDs 790 may be input from a computer remote from the light source apparatus 600 through the communication cable 720. Thus, the LED power supply 780 can control light emission of the light-emitting device 310. The LED power supply 780 includes a control circuit for controlling the output of the LEDs 790 and a communication circuit for transmission and reception of information. Thus, the use of LEDs as excitation light sources can also achieve the same function.

Figure 61E:
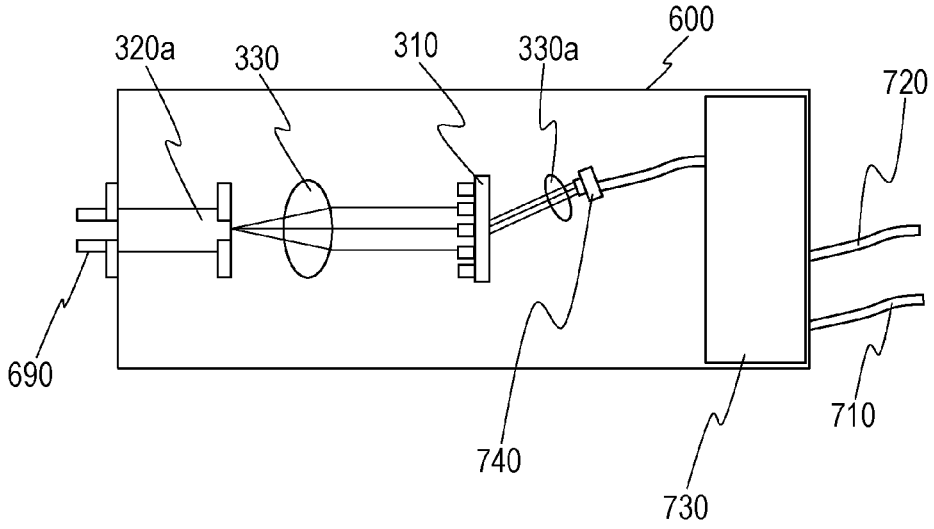
FIG. 61E is a top view of still another structure of the light source apparatus.

FIG. 61E is a top view of still another structure of the light source apparatus 600. The light source apparatus 600 includes one laser diode 740 and a lens 330a for condensing excitation light from the laser diode 740 and obliquely directing the excitation light to the light-emitting device 310. Except for this, the light source apparatus 600 has the same structure as illustrated in FIG. 61A. Excitation light is directed obliquely with respect to the direction normal to the photoluminescent layer of the light-emitting device 310. The incident angle is adjusted such that excitation light is totally reflected in the photoluminescent layer. This structure can also have the same function as those described above.

As described above, the light source apparatus 600 can be variously modified. The light source apparatus 600 can be applied not only to fiber lighting apparatuses for use in high places but also to lighting apparatuses according to the present disclosure for other uses.

11-6. Vehicle Fiber Illumination

A vehicle optical fiber lighting apparatus including a light-emitting device according to the present disclosure will be described below.

Figure 62:
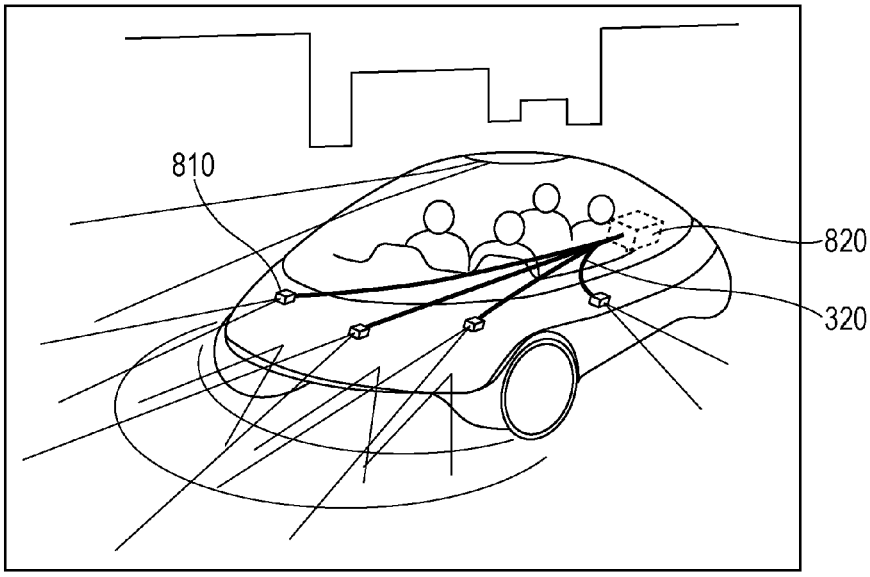
FIG. 62 is a schematic view of a vehicle that includes a vehicle fiber lighting apparatus.

FIG. 62 is a schematic view of a vehicle that includes a lighting apparatus according to the present application example. The lighting apparatus according to the present application example includes an excitation light source unit 820 within the vehicle, optical fibers 320, and light-emitting units 810 outside the vehicle. The light-emitting units 810 are coupled to the excitation light source unit 820 through the optical fibers 320. The excitation light source unit 820 includes an optical connector for coupling an excitation light source to the optical fibers 320. Each of the light-emitting units 810 includes the light-emitting device according to any one of the embodiments described above and an optical connector for coupling the optical fibers 320 to the light-emitting units 810.

Figure 63:
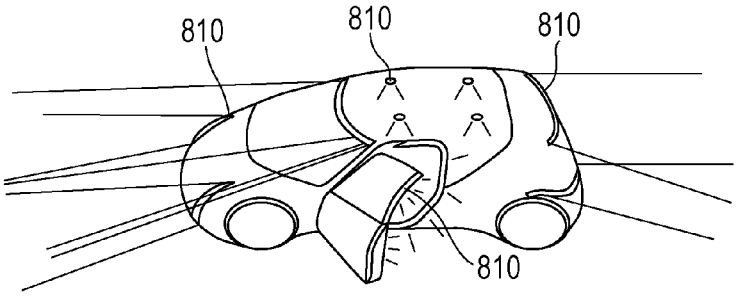

The light-emitting units 810 outside or inside the vehicle coupled to each end (light exit) of the optical fibers 320 can emit light in any direction, including the rear or top of the vehicle that is difficult to see from the inside of the vehicle. As illustrated in FIG. 63, the light-emitting units 810 may be applied to headlights, taillights, and door lights.

The light-emitting device may be disposed in the excitation light source unit 820 instead of the light-emitting units 810. In this case, the excitation light source unit 820 has the same structure as the "light source apparatus 600", and the light-emitting units 810 have the same structure as the "illumination unit(s) 660".

Figure 64:
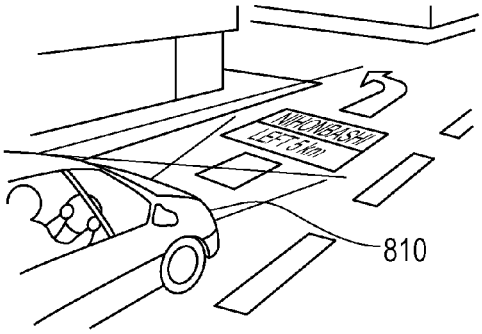

FIG. 64 illustrates another application example applied to a vehicle. A light-emitting unit in combination with a navigation system can display a navigation image on a projection plane, such as a road surface. In order to perform this function, the vehicle has a projector. The projector may have a novel structure that includes a light-emitting device according to the present disclosure as a light source. For example, a light-emitting device having high directionality according to the present disclosure may be substituted for phosphors in phosphor wheels of known projectors (e.g., disclosed in Japanese Unexamined Patent Application Publication No. 2012-8177 and No. 2014-191003). For example, a light-emitting device that emits red light approximately perpendicularly to the photoluminescent layer and a light-emitting device that emits green light approximately perpendicularly to the photoluminescent layer may be substituted for a red phosphor layer and a green phosphor layer in a phosphor wheel disclosed in Japanese Unexamined Patent Application Publication No. 2014-191003.

In the present application example, the light-emitting unit 810 functions not only as an illuminator but also as a display unit that displays a navigation image. Thus, an unprecedentedly convenient car navigation system can be provided.

11-7. Fiber Sensor

It is desirable that a light-emitting device according to the present disclosure be used in optical fiber sensors for detecting the displacement or deformation of vehicles and aircrafts. An optical fiber sensor for detecting the displacement or deformation of vehicles is disclosed in Japanese Unexamined Patent Application Publication No. 2006-282114, for example. In known optical fiber sensors, however, because of weak backscattered light caused by Rayleigh scattering, light sources, detectors, and circuits disadvantageously have large sizes. This problem must be solved in order to meet the demands for smaller vehicle systems. The use of a light-emitting device according to the present disclosure can provide a compact high-sensitivity optical fiber sensor. Such an optical fiber sensor will be described below.

A single-ended optical fiber of an optical fiber sensor according to the present embodiment is stretched around an automobile or aircraft body and detects the deformation of the body or a damaged portion utilizing the time-of-flight (TOF) principle. A deformed portion or displacement can be detected by inputting pulsed light into the optical fiber and analyzing the (group) delay time of the pulsed light.

Figure 65A:
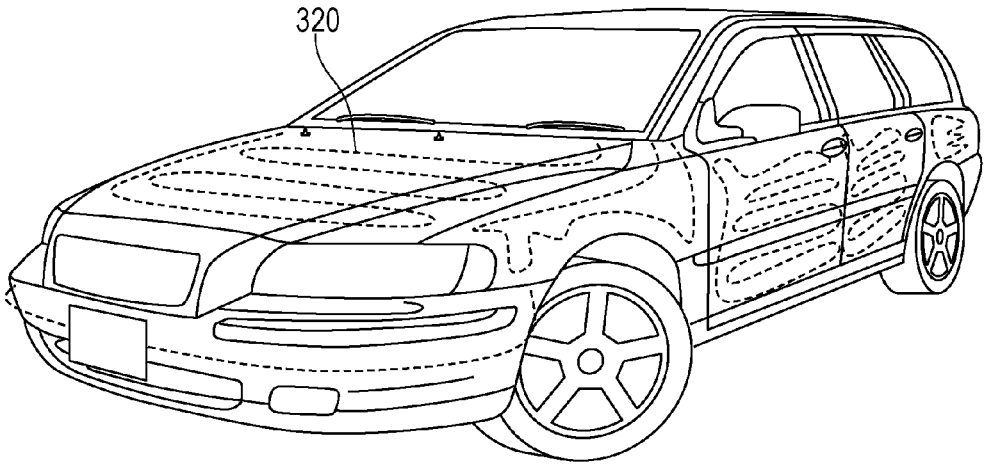
Figure 65B:
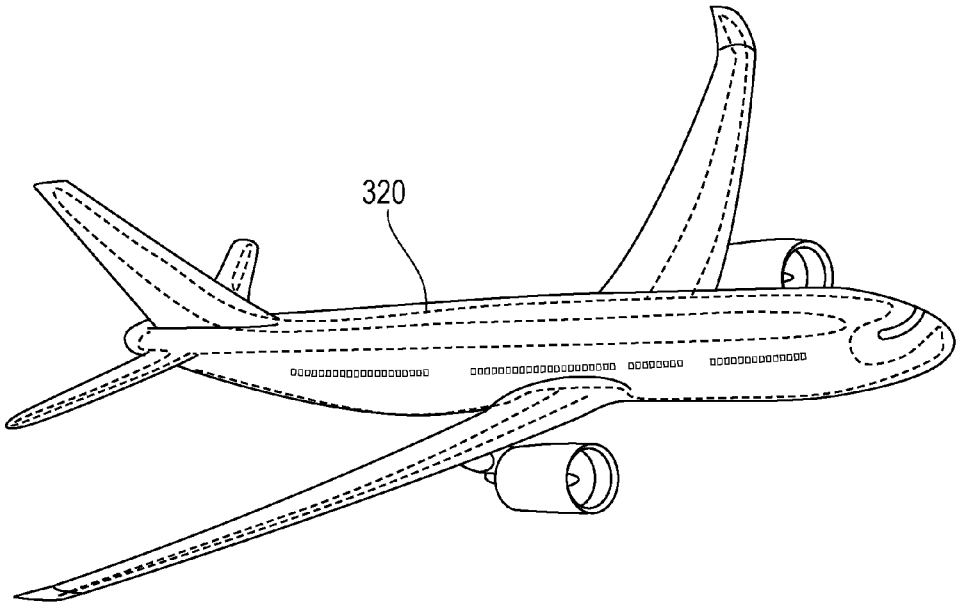

FIG. 65A is a schematic view of an automobile that includes an optical fiber sensor according to the present embodiment. FIG. 65B is a schematic view of an airplane that includes an optical fiber sensor according to the present embodiment. In both examples, an optical fiber 320 is stretched around the body.

Figure 66:
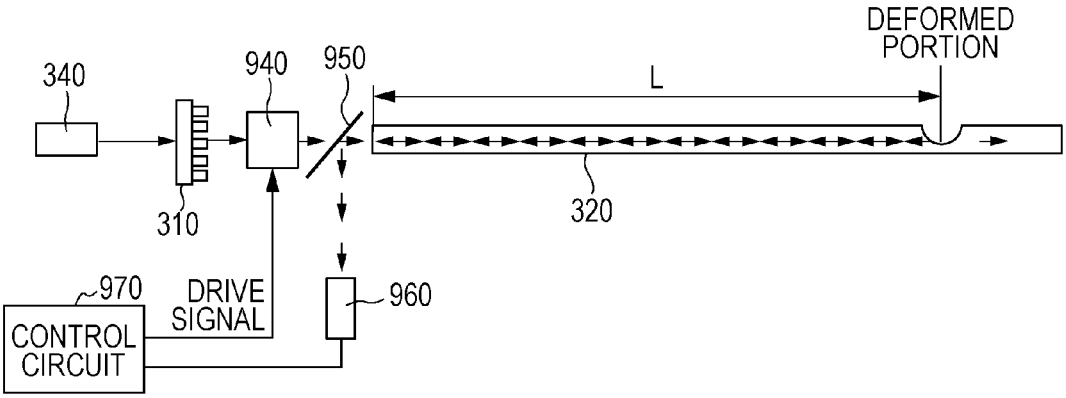

FIG. 66 is an explanatory view of the structure and the principle of operation of an optical fiber sensor. The optical fiber sensor includes an excitation light source 340, a light-emitting device 310, an optical shutter 940, a half-mirror 950, a photoreceptor 960, a control circuit 970, and an optical fiber 320. The light-emitting device 310 has the same structure as one of the light-emitting devices according to the embodiments described above. The light-emitting device 310 emits narrow-angle light in response to excitation light from the excitation light source 340. The optical shutter 940 is disposed on the optical path of light emitted from the light-emitting device 310. For example, the optical shutter 940 includes a liquid crystal layer and two electrode layers on both sides of the liquid crystal layer. In response to a drive signal from the control circuit 970, the optical shutter 940 switches between a state that allows light from the light-emitting device 310 to pass through the optical shutter 940 (hereinafter referred to as a light-transmissive state) and a state that blocks the light (hereinafter referred to as a light-shielding state). The half-mirror 950 is disposed on the optical path of light passing through the optical shutter 940. Light passing through the half-mirror 950 enters the optical fiber 320. Light reflected from the half-mirror 950 enters the photoreceptor 960. The photoreceptor 960 may include a photodiode and output an electric signal depending on the amount of light received (hereinafter referred to as a light-responsive signal). The control circuit 970 inputs a drive signal for switching between the light-transmissive state and the light-shielding state of the optical shutter 940 into the optical shutter 940. This allows the optical shutter 940 to output pulsed light. The control circuit 970 analyzes electric signals output from the photoreceptor 960. For example, the control circuit 970 may be an integrated circuit including a processor, such as a microcontroller. For the sake of simplicity, the optical fiber 320 in FIG. 66 has a linear form.

A lens may be disposed between the light-emitting device 310 and the optical shutter 940 and between the optical shutter 940 and the half-mirror 950. The optical shutter 940 may be disposed at a position at which light from the light-emitting device 310 forms an image through the lens. This can reduce the size of the optical shutter 940 and allows the light-transmissive state and the light-shielding state to be switched at high speed. Such a compact shutter may be provided by a microelectromechanical system (MEMS). The transmittance and reflectance of the half-mirror 950 are not necessarily identical, and the half-mirror 950 may be a beam splitter that have different transmittance and reflectance.

In such a structure, light emitted from the light-emitting device 310 and excited by excitation light is modulated to pulsed light by the optical shutter 940 in response to a drive signal. The pulsed light is transmitted to the optical fiber 320 through the half-mirror 950. The incident light propagates through the optical fiber 320 stretched around the body and is partly or entirely reflected from a deformed portion of the optical fiber 320. The reflected light is directed to the photoreceptor 960 via the half-mirror 950. The photoreceptor 960 sends the control circuit 970 a light-responsive signal depending on the intensity of the reflected light.

Figure 67:
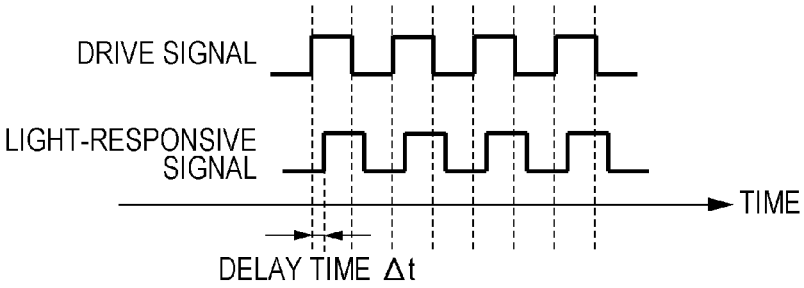

FIG. 67 is a diagram of a drive signal and a light signal as a function of time. The control circuit 970 determines the distance L from the end portion of the optical fiber 320 to the deformed portion on the basis of the delay time $\Delta t$ between the drive signal and the light-responsive signal. The distance L is calculated using the following equation.

$$L = \text{Speed of light in optical fiber } 320 \times \text{Delay time } \Delta t/2 = \left(\frac{\text{Speed of light } c}{\text{Refractive index } n \text{ of optical fiber } 320}\right) = \text{Delay time } \Delta t/2$$

The position of the deformed portion of the optical fiber 320 stretched around the body can be determined from the distance L to the deformed portion. Thus, the deformed portion, for example, due to an accident can be identified.

In the light-emitting device 310 according to the present embodiment, the output beam has a very narrow angle of divergence. This results in high coupling efficiency in the optical fiber 320 and a very low optical loss. This allows very weak reflected light in the optical fiber 320 to be detected and can reduce the size and weight of the detector and the power supply circuit.

Although pulsed light is produced by controlling the optical shutter 940 in the present embodiment, the present disclosure is not limited to the present embodiment. For example, pulsed light may be produced by controlling the on and off state of the excitation light source 340 instead of controlling the optical shutter 940.

Although there is one deformed portion in the present embodiment, two or more deformed portions may also be identified. In the case of two or more deformed portions, reflected light is composed of pulsed light components having different phases and amplitudes. Individual reflected light components can be identified, for example, by performing Fourier transformation on the combined wave contained in a light-responsive signal using a fast Fourier transform (FFT) analyzer. Thus, the delay time Δt can be determined for each reflected light component, and the distance L to each deformed portion can be calculated.

11-8. Other Application Examples

Other application examples of a light-emitting device according to the present disclosure will be described below.

A light-emitting device according to the present disclosure can emit directional light in a particular direction. It is desirable that such high directionality be utilized in edge-light backlight units that utilize a light guide plate of a liquid crystal display unit. For example, when a known light source having low directionality is used, light from the light source is directed to a light guide plate through a reflector and/or a diffuser. When a light source having high directionality in a particular direction is used, light can be efficiently directed to a light guide plate without these optical components.

In optical devices, light from a light source must be efficiently directed in a predetermined direction. Thus, optical devices include a lens, a prism, and/or a reflector, for example. For example, it is known that a projector includes a light guide to direct light from a light source to a display panel (e.g., Japanese Unexamined Patent Application Publication No. 2010-156929). The use of a light-emitting device according to the present disclosure as a light source can remove the light guide.

Known lighting fixtures include an optical component, including a lens and/or a reflector, to direct isotropic light in a desired direction. The use of a light-emitting device according to the present disclosure can remove such an optical component. The use of a light-emitting device according to the present disclosure allows for a simple design for directional light instead of a complex design for isotropic light. Consequently, lighting fixtures can be reduced in size, or the process of designing lighting fixtures can be simplified.

In the field of illumination, color-enhancing light color illumination and beautifying light color illumination techniques have been developed. Such illumination can finely produce the color of an object to be illuminated. The color-enhancing light color illumination is effective in making foods, such as vegetables, look more delicious. The beautifying light color illumination is effective in ensuring natural-looking skin tones. Such illumination is performed by controlling the light source spectrum (the intensity distribution as a function of light wavelength) depending on the object. Hitherto, the spectrum of illumination light has been controlled by selective transmission of light emitted from a light source using an optical filter. The optical filter absorbs unnecessary light and consequently reduces light-use efficiency. In contrast, a light-emitting device according to the present disclosure can enhance light having a particular wavelength and requires no optical filter, thus improving light-use efficiency.

A light-emitting device according to the present disclosure can emit polarized light (e.g. linearly polarized light). When unpolarized light including two linearly polarized light components intersecting at right angles is emitted from a light source, linearly polarized light has hitherto been produced by absorbing one of the two linearly polarized light components using a polarizing filter (also referred to as a "polarizer"). Thus, the light-use efficiency is 50% or less. The use of a light-emitting device according to the present disclosure as a polarized light source can obviate the need for a polarizing filter and improve light-use efficiency. Polarized illumination is used to reduce reflected light, for example, from windowpanes of shop windows and view restaurants. Polarized illumination is also used as washstand illumination, which utilizes the dependence of the reflection characteristics of the skin surface on polarized light, and is used to facilitate the observation of lesion sites with an endoscope.

It is desirable that a polarized light source be used as a backlight for liquid crystal display units and as a light source for liquid crystal projectors. When a light-emitting device according to the present disclosure is used as a light source for liquid crystal projectors, in combination with the use of the wavelength selectivity, the light-emitting device can constitute a three-primary-color polarized light source. For example, a light-emitting device that emits red linearly polarized light, a light-emitting device that emits green linearly polarized light, and a light-emitting device that emits blue linearly polarized light may be joined together to form a disk. While the disk is irradiated with excitation light, the disk may be rotated to form a light source that successively emits red, green, and blue three-primary-color polarized light beams.

Figure 68:
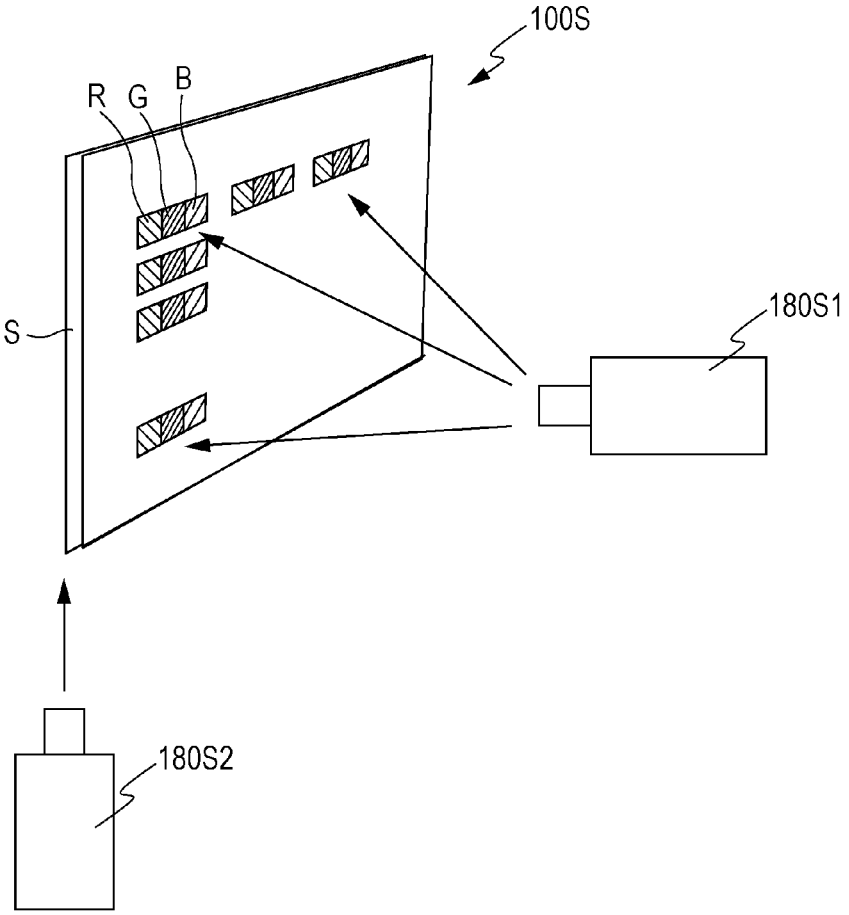

As illustrated in FIG. 68, a light-emitting device according to the present disclosure may also be used as a screen 100S of a transparent display apparatus.

For example, the screen 100S includes pixels arranged in a matrix. Each of the pixels is composed of a light-emitting device that enhances red light (R), a light-emitting device that enhances green light (G), and a light-emitting device that enhances blue light (B). These light-emitting devices can emit light of a predetermined color in response to their respective excitation light (e.g., ultraviolet light) emitted from an excitation light source 180S1, thereby displaying an image. Because the light-emitting devices transmit visible light, observers can observe the background through the screen 100S. When the screen 100S is not irradiated with excitation light, the screen 100S looks like a transparent window. Scanning a laser diode as the excitation light source 180S1 while adjusting its output for image data enables high resolution display. Since a laser beam is coherent light, its excitation efficiency can also be increased by interference with a periodic structure. When light having an undesirable wavelength, such as ultraviolet light, is used as excitation light, a leakage of the undesirable light can be prevented by placing an excitation light source on the opposite side of the screen 100S from the observer and placing a filter for removing the excitation light on the observer side of the screen 100S.

The screen 100S may have high directionality. Thus, only observers in a predetermined direction can observe images.

The excitation light source 180S1 may be replaced with an excitation light source 180S2. A light guide sheet S is placed on the back side of the screen 100S (i.e., opposite the observer) and is irradiated with excitation light from the excitation light source 180S2. The excitation light incident on the light guide sheet S propagates through the screen 100S and is applied to the back side of the screen 100S. In this case, light-emitting devices arranged according to a desired image cannot actively display any image. However, the light guide sheet S can be transparent like a window in the absence of excitation light and can display images, figures, and letters when irradiated with excitation light.

As described above with reference to FIGS. 8 and 9, a change in the refractive index of a periodic structure of a light-emitting device according to the present disclosure results in a different wavelength and output direction of enhanced light. The wavelength and output direction of enhanced light also change with the refractive index of a photoluminescent layer. Thus, a change in the refractive index of a medium around the light-emitting device can be easily detected with high sensitivity.

For example, a sensor for detecting various substances can be provided using a light-emitting device according to the present disclosure, as described below.

A substance (such as an enzyme) that selectively binds to a substance to be measured (such as a protein, odorant molecule, or virus) is placed near a periodic structure of a light-emitting device according to the present disclosure. Bonding to the substance to be measured changes the refractive index of a medium around the light-emitting device. The change in the refractive index can be detected as a change in the wavelength or output direction of enhanced light, as described above. Thus, the presence of various substances can be detected.

Application examples of a light-emitting device according to the present disclosure are not limited to those described above. A light-emitting device according to the present disclosure can be applied to various optical devices.

Light-emitting devices and light-emitting apparatuses according to the present disclosure can be applied to various optical devices, such as lighting fixtures, displays, and projectors.

The contents of all the cited documents are incorporated herein by reference in their entirety.

What is claimed is:

1. A light-emitting apparatus comprising:

a light-emitting device including a photoluminescent layer that receives excitation light and emits light including first light having a wavelength $\lambda_a$ in air, and a light-transmissive layer located on or near the photoluminescent layer; and an optical fiber that receives the light from the photoluminescent layer at one end of the optical fiber and emits the received light from the other end thereof, *wherein*

[wherein] a surface structure is defined on at least one of the photoluminescent layer and the light-transmissive layer, and the surface structure has projections or recesses or both with a shorter period than the wavelength $\lambda_a$ *in air* and limits a directional angle of the first light having the wavelength $\lambda_a$ in air.

2. The light-emitting apparatus according to claim 1, wherein the light-emitting device includes a first emission region that emits light in a green wavelength band in a direction perpendicular to the photoluminescent layer and a second emission region that emits light in a blue wavelength band in a direction perpendicular to the photoluminescent layer.

3. The light-emitting apparatus according to claim 1, wherein the light-emitting device further includes another photoluminescent layer that receives the excitation light and emits light including second light having a wavelength $\lambda_b$ in air, and another light-transmissive layer located on or near the other photoluminescent layer, wherein the photoluminescent layer and the light-transmissive layer constitute a first emission region that emits the light including the first light from the photoluminescent layer in a direction perpendicular to the photoluminescent layer, the wavelength $\lambda_a$ *in air* is in the green wavelength band, the other photoluminescent layer and the other light-transmissive layer constitute a second emission region that emits the light including the second light from the other photoluminescent layer in a direction perpendicular to the other photoluminescent layer, the wavelength $\lambda_b$ *in air* is in a blue wavelength band, another surface structure is defined on at least one of the other photoluminescent layer and the other light-transmissive layer, and the other surface structure has projections or recesses or both and limits a directional angle of the second light having the wavelength $\lambda_b$ in air.

4. The light-emitting apparatus according to claim 2, wherein the first emission region and the second emission region are arranged in a direction perpendicular to the photoluminescent layer.

5. The light-emitting apparatus according to claim 1, wherein the light-emitting device includes an emission region that emits light in a green wavelength band in a direction perpendicular to the photoluminescent layer, and the excitation light is light in a blue wavelength band, and part of the excitation light passes perpendicularly through the photoluminescent layer.

6. The light-emitting apparatus according to claim 1, wherein the photoluminescent layer and the light-transmissive layer constitute an first emission region that emits the light including the first light from the photoluminescent layer in a direction perpendicular to the photoluminescent layer, and the wavelength $\lambda_a$ *in air* is in the green wavelength band.

7. The light-emitting apparatus according to claim 2, wherein the blue wavelength band ranges from 430 to 470 nm, and the green wavelength band ranges from 500 to 570 nm.

8. The light-emitting apparatus according to claim 1, wherein the photoluminescent layer is in contact with the light-transmissive layer.

9. The light-emitting apparatus according to claim 1, wherein a center-to-center distance $D_{int}$ between two adjacent projections or two adjacent recesses in the surface structure and a refractive index $n_{wav\text{-}a}$ of the photoluminescent layer for the first light satisfy $\lambda_a/n_{wav\text{-}a}<D_{int}<\lambda_a$.

10. The light-emitting apparatus according to claim 1, wherein the surface structure includes at least one periodic structure, and a period $p_a$ of the at least one periodic structure and a refractive index $n_{wav\text{-}a}$ of the photoluminescent layer for the first light satisfy [$\lambda_a/n_{wav\text{-}a}<_{Pa}<\lambda_a$] $\lambda_a/n_{wav\text{-}a}<p_a<\lambda_a$.

11. An endoscope comprising:

the light-emitting apparatus according to claim 1; and an imaging device that receives the light emitted by the optical fiber and reflected by an object, and outputs an electric signal depending on the amount of the received light.

12. The endoscope according to claim 11, further comprising an insert, wherein the light-emitting device and the imaging device are provided in the insert.

13. The endoscope according to claim 11, further comprising an optical system that faces an imaging plane of the imaging device and converge the light emitted by the optical fiber and reflected by an object onto the imaging plane.

14. An endoscope system comprising:

the endoscope according to claim 11;

a processor that is electrically connected to the imaging device in the endoscope and outputs an image signal based on the electric signal; and a display unit that is electrically connected to the processor and displays an image based on the image signal.

15. The light-emitting apparatus according to claim 1, wherein the surface structure includes at least one periodic structure having a period that allows an electric field to be formed in the photoluminescent layer, in which a period of maximum amplitude of the electric field is the same as the period of the at least one periodic structure.

16. The light-emitting apparatus according to claim 1, wherein the photoluminescent layer has a thickness that allows a quasi-guided mode to be formed within the photoluminescent layer.

17. The light-emitting apparatus according to claim 1, wherein a distance between the light-transmissive layer and the photoluminescent layer is equal to or less than $\lambda_a/2$.

18. A light-emitting apparatus comprising:

an excitation light source that outputs excitation light;

an optical fiber that receives the excitation light from the excitation light source at one end of the optical fiber and emits the received excitation light from the other end thereof; and a light emitting device including a photoluminescent layer that receives the excitation light emitted from the optical fiber and emits light including first light having a wavelength $\lambda_a$ in air, and a light-transmissive layer located on or near the photoluminescent layer, *wherein*

[wherein] a surface structure is defined on at least one of the photoluminescent layer and the light-transmissive layer, and the surface structure has projections or recesses or both with a shorter period than the wavelength $\lambda_a$ *in air* and limits a directional angle of the first light having the wavelength $\lambda_a$ in air.

19. The light-emitting apparatus according to claim 18, wherein the surface structure includes at least one periodic structure having a period that allows an electric field to be formed in the photoluminescent layer, in which a period of maximum amplitude of the electric field is the same as the period of the at least one periodic structure.

20. The light-emitting apparatus according to claim 18, wherein the photoluminescent layer has a thickness that allows a quasi-guided mode to be formed within the photoluminescent layer.

21. The light-emitting apparatus according to claim 18, wherein a distance between the light-transmissive layer and the photoluminescent layer is equal to or less than $\lambda_a/2$.

22. A light-emitting apparatus comprising:

a light-emitting device including a light-transmissive layer and a photoluminescent layer that receives excitation light and emits light including first light having a wavelength $\lambda_a$ in air; and at least one of (a) a first optical fiber that receives the light from the photoluminescent layer at one end of the first optical fiber and emits the received light from the other end thereof [and] *or* (b) a second optical fiber that receives the excitation light from an excitation light source at one end of the second optical fiber and emits the received excitation light from the other end thereof toward the light-emitting device, *wherein*

[wherein] a surface structure is defined on the light-transmissive layer, the photoluminescent layer is located on or near the surface structure, and the surface structure has projections or recesses or both with a shorter period than the wavelength $\lambda_a$ *in air* and limits a directional angle of the first light having the wavelength $\lambda_a$ in air.

23. The light-emitting apparatus according to claim 22, wherein the surface structure includes at least one periodic structure having a period that allows an electric field to be formed in the photoluminescent layer, in which a period of maximum amplitude of the electric field is the same as the period of the at least one periodic structure.

24. The light-emitting apparatus according to claim 22, wherein a distance between the surface structure and the photoluminescent layer is equal to or less than $\lambda_a/2$.

25. The light-emitting apparatus according to claim 22, wherein the photoluminescent layer has a thickness that allows a quasi-guided mode to be formed within the photoluminescent layer.

26. A light-emitting apparatus comprising:

a light-emitting device including a photoluminescent layer that receives excitation light and emits light including first light having a wavelength $\lambda_a$ in air, and a light-transmissive layer having a higher refractive index for the first light than the photoluminescent layer; and at least one of (a) a first optical fiber that receives the light from the photoluminescent layer at one end of the first optical fiber and emits the received light from the other end thereof [and] *or* (b) a second optical fiber that receives the excitation light from an excitation light source at one end of the second optical fiber and emits the received excitation light from the other end thereof toward the light-emitting device, *wherein*

[wherein] a surface structure is defined on the light-transmissive layer, and the surface structure has projections or recesses or both with a shorter period than the wavelength $\lambda_a$ *in air* and limits a directional angle of the first light having the wavelength $\lambda_a$ in air.

27. The light-emitting apparatus according to claim 26, wherein the surface structure includes at least one periodic structure having a period that allows an electric field to be formed in the photoluminescent layer, in which a period of maximum amplitude of the electric field is the same as the period of the at least one periodic structure.

28. A light-emitting apparatus comprising:

a light-emitting device including a photoluminescent layer that receives excitation light and emits light including first light having a wavelength $\lambda_a$ in air; and at least one of (a) a first optical fiber that receives the light from the photo luminescent layer at one end of the first optical fiber and emits the received light from the other end thereof [and] *or* (b) a second optical fiber that receives the excitation light from an excitation light source at one end of the second optical fiber and emits the received excitation light from the other end thereof toward the light-emitting device, *wherein*

[wherein] a surface structure is defined on the photoluminescent layer, and the surface structure has projections or recesses or both with a shorter period than the wavelength $\lambda_a$ *in air* and limits a directional angle of the first light having the wavelength $\lambda_a$ in air.

29. The light-emitting apparatus according to claim 26, wherein the photoluminescent layer has a thickness that allows a quasi-guided mode to be formed within the photoluminescent layer.

30. The light-emitting apparatus according to claim 28, wherein the surface structure includes at least one periodic structure having a period that allows an electric field to be formed in the photoluminescent layer, in which a period of maximum amplitude of the electric field is the same as the period of the at least one periodic structure.

31. The light-emitting apparatus according to claim 28, wherein the photoluminescent layer has a thickness that allows a quasi-guided mode to be formed within the photoluminescent layer.

*32. A light-emitting apparatus comprising:*

*an excitation light source that outputs excitation light; and*

*a light emitting device located on an optical path of the excitation light and the light emitting device including:*

*a photoluminescent layer receives the excitation light and emits light including first light having a wavelength $\lambda_a$ in air; and*

*a light-transmissive layer located on or near the photoluminescent layer, wherein:*

*a surface structure is defined on at least one of the photoluminescent layer and the light-transmissive layer, and the surface structure has projections or recesses or both, and*

*the surface structure includes at least one periodic structure with a period $p_a$ for limiting a directional angle of the first light having the wavelength $\lambda_a$ in air, and the period $p_a$ is shorter than the wavelength $\lambda_a$ in air.*

*33. The light-emitting apparatus according to claim 32, further comprising:*

*a first light guide located on an optical path of the excitation light for receiving the excitation light at a first end of the first light guide and outputting the received excitation light from a second end of the first light guide.*

*34. The light-emitting apparatus according to claim 33, wherein the first light guide includes an optical fiber or a light guide sheet.*

*35. The light-emitting apparatus according to claim 32, the light-emitting device is adapted to a vehicle, an automobile, an airplane or an aircraft.*

*36. The light-emitting apparatus according to claim 32, the light-emitting device is adapted to a projector.*

*37. The light-emitting apparatus according to claim 36, wherein the projector includes a phosphor wheel having the light-emitting device.*

*38. A navigation image display, comprising:*

*the light-emitting apparatus according to claim 35; and*

*a second light guide for directing light from the light-emitting device to a projection plane.*

*39. The navigation image display according to claim 38, wherein the second light guide includes a lens, a prism, a reflector, or combination thereof.*

*40. An optical sensor, comprising:*

*the light-emitting apparatus according to claim 32;*

*an optical shutter disposed on the optical path of light emitted from the light-emitting device and is used to switch the light from the light-emitting device into a pulsed light for emitting to a body; and*

*a photoreceptor for receiving a reflected light of the pulsed light from the body and output an electric signal to a processor for detecting a deformation of the body or a displacement of the body.*

*41. The optical sensor according to claim 40, wherein the optical sensor is adapted to an automobile or an airplane.*

*42. A light-emitting apparatus comprising:*

*an excitation light source that outputs excitation light; and*

*a light emitting device located on an optical path of the excitation light and the light emitting device including:*

*a photoluminescent layer receives the excitation light and emits light including first light having a wavelength $\lambda_a$ in air; and*

*a light-transmissive layer located on or near the photoluminescent layer, wherein:*

*a surface structure is defined on at least one of the photoluminescent layer and the light-transmissive layer, and the surface structure has projections or recesses or both, and*

*the surface structure includes at least one periodic structure with a period $p_a$ for limiting a directional angle of the first light having the wavelength $\lambda_a$ in air, and the period $p_a$ satisfies $m \times \lambda_a / n_{wav\text{-}a} < p_a < m \times \lambda_a$, wherein $n_{wav\text{-}a}$ is a refractive index of the photoluminescent layer or the light-transmissive layer, and m is an integer of 1 or more.*

*43. The light-emitting apparatus according to claim 42, further comprising:*

*a first light guide located on an optical path of the excitation light for receiving the excitation light at a first end of the first light guide and outputting the received excitation light from a second end of the first light guide.*

*44. The light-emitting apparatus according to claim 43, wherein the first light guide includes an optical fiber or a light guide sheet.*

*45. The light-emitting apparatus according to claim 42, the light-emitting device is adapted to a vehicle, an automobile, an airplane or an aircraft.*

*46. The light-emitting apparatus according to claim 42, the light-emitting device is adapted to a projector.*

*47. The light-emitting apparatus according to claim 45, wherein the projector includes a phosphor wheel having the light-emitting device.*

*48. A navigation image display, comprising:*

*the light-emitting apparatus according to claim 45; and*

*a second light guide for directing light from the light-emitting device to a projection plane.*

*49. The navigation image display according to claim 48, wherein the second light guide includes a lens, a prism, a reflector, or combination thereof.*

*50. An optical sensor, comprising:*

*the light-emitting apparatus according to claim 42;*

*an optical shutter disposed on the optical path of light emitted from the light-emitting device and is used to switch the light from the light-emitting device into a pulsed light for emitting to a body; and*

*a photoreceptor for receiving a reflected light of the pulsed light from the body and output an electric signal to a processor for detecting a deformation of the body or a displacement of the body.*

*51. The optical sensor according to claim 50, wherein the optical sensor is adapted to an automobile or an airplane.*

* * * * *